United States Patent
Zeisberg et al.

(10) Patent No.: US 11,331,333 B2
(45) Date of Patent: May 17, 2022

(54) TREATMENT OF ABERRANT FIBROBLAST PROLIFERATION

(71) Applicants: Georg August Universitaet Goettingen Stiftung Oeffentlichen Rechts, Universitaetsmedizin, Goettingen (DE); The University of Texas MD Anderson Cancer Center, Houston, TX (US)

(72) Inventors: Michael Zeisberg, Goettingen (DE); Elisabeth Zeisberg, Goettingen (DE); Bjoern Tampe, Goettingen (DE); Gerhard Anton Mueller, Goettingen (DE); Xu Xingbo, Goettingen (DE); Desiree Tampe, Goettingen (DE); Raghu Kalluri, Houston, TX (US)

(73) Assignees: Georg-August-Universität Göttingen Stiftung Öffentichen Rechts, Universitätsmadizin, Göttingen (DE); Board of Regents, The University of Texas System, Houston, TX (US)

( * ) Notice: Subject to any disclaimer, the term of this patent is extended or adjusted under 35 U.S.C. 154(b) by 0 days.

(21) Appl. No.: 16/678,398

(22) Filed: Nov. 8, 2019

(65) Prior Publication Data

US 2021/0137963 A1 May 13, 2021

(51) Int. Cl.
| | | |
|---|---|---|
| C07H 21/02 | (2006.01) |
| A61K 31/713 | (2006.01) |
| C12Q 1/6869 | (2018.01) |
| C07K 14/47 | (2006.01) |
| C12N 15/113 | (2010.01) |

(52) U.S. Cl.
CPC ........ *A61K 31/713* (2013.01); *C07K 14/4702* (2013.01); *C12N 15/113* (2013.01); *C12Q 1/6869* (2013.01); *C12N 2310/11* (2013.01); *C12Q 2600/154* (2013.01)

(58) Field of Classification Search
CPC .......................... C12N 15/113; C12N 2310/11
See application file for complete search history.

(56) References Cited

U.S. PATENT DOCUMENTS

| | | |
|---|---|---|
| 9,725,430 B2 | 8/2017 | Hegde |
| 9,962,362 B2 | 5/2018 | Hegde |
| 2005/0009771 A1 | 1/2005 | Levanon |
| 2011/0038791 A1 | 2/2011 | Ford |

FOREIGN PATENT DOCUMENTS

| | | |
|---|---|---|
| WO | WO 2004/112565 A | 12/2004 |
| WO | WO 2008/045498 A | 4/2008 |
| WO | WO 2016/046130 A | 3/2016 |
| WO | WO 2016/085981 A | 6/2016 |
| WO | WO 2017/132746 A | 8/2017 |
| WO | WO 2019/067011 A | 4/2019 |

OTHER PUBLICATIONS

Bamberg et al. (American Journal of Respiratory and Critical Care Medicine, 198, 7, 2018, 914-926).*
Mao et al., "Comparison of nonhomologous end joining and homologous recombination in human cells" DNA Repair, 2008;7(10):1765-1771.
McAvoy et al., "Serine/Threonine Protein Phosphatase Assays" Curr. Protoc. Mol. Biol., 2010;unit 18.18.
Millhouse et al., "The C-Trerminal Domain of RNA Polymerase II Functions as a Phosphorylation-Dependent Splicing. . . " Mol. Cell Biol., 2005;25(2):533-544.
Ostrowski et al., "Nuclear shift of hnRNP K protein in neoplasms and other states of enhanced cell proliferation" British J. Cancer, 2003;89:1493-1501.
Pandey et al., "The Eyes Absent phosphatase-transactivator proteins promote proliferation, transformation, migration, and invasion of tumor cells" Oncogene, 2010;29:3715-3722.
Paz et al., "SFmap: a web server for motif analysis and prediction of splicing factor binding sites" Nuc. Acids. Res., 2010;38:W281-285.
Pierce et al., "XRCC3 promotes homology-directed repair of DNA damage in mammalian cells" Genes Dev, 1999;13:2633-2638.
Rebay et al., "Multiple Functions of the Eya Phosphotyrosine Phosphatase" Mol. Cell. Biol, 2016;36(5):668-677.
Rockey et al., "Fibrosis—A Common Pathway to Organ Injury and Failure" N. Engl. J. Med., 2015;372(12):1138-1149.
Rodemann et al., "Abnormal Growth and Clonal Proliferation of Fibroblasts Derived from Kidneys with Interstitial Fibrosis" Proc. Soc. Exp. Biol. Med., 1990;195:57-63.
Rogakou et al., "DNA Double-stranded Breaks Induce Histone H2AX Phosphorylation on Serine 139*" J. Biol. Chem., 1998;273(10):5858-5868.
Seluanov et al., "DNA end joining becomes less efficient and more error-prone during cellular senescence" PNAS, 2004;101(20):7624-7629.
Srivastava et al., "An Inhibitor of Nonhomologous End-Joining Abrogates Double-Strand. . . " Cell, 2012;151:1474-1487.
Stewart et al., "MDC1 is a mediator of the mammalian DNA damage checkpoint" Nature, 2003;421:961-966.
Stockley et al., "A Recurrent EYA1 Mutation Causing Alternative RNA Splicing in Branchio-Oto-Renal SYndrome:. . . " Am. J. Med. Genet. Part A, 2009;149A:322-327.
Sturmlechner et al., "Cellular senescence in renal ageing and disease" Nature Rev. Nephrol., 2017;13:77-89.
Svegliati et al., "Oxidative DNA damage induces the ATM-mediated transcriptional suppression of Wnt inhibitor. . . " Sci. Signal., 2014;7(341).
Tampe et al., "Induction of Tet3-dependent Epigenetic Regulation by Low-dose Hydralazine Attenuates Progression. . . " EBioMedicine, 2015;2:19-36.

(Continued)

*Primary Examiner* — Amy H Bowman

(57) ABSTRACT

Provided is a method of preventing, treating or delaying progression of a disease involving aberrant fibroblast proliferation. The method involves using a compound that reduces the level of tyrosine phosphatase activity effected by the protein EYA1A in the parenchymal organ, a nucleic acid ligase IV inhibitor, or an antisense oligonucleotide against the p53-binding protein 1 (53BP1).

10 Claims, 36 Drawing Sheets

Specification includes a Sequence Listing.

(56) References Cited

OTHER PUBLICATIONS

Tampe et al., "Potential approaches to reverse or repair renal fibrosis" Nat. Rev. Nephrol., 2014;10:226-237.
Tampe et al., "Evidence for the involvement of epigenetics in the progression of renal fibrogenesis" Nephrol. Dial. Transplant, 2014;29:i1-i8.
Abdelhak et al., "A human homologue of the Drosophila eyes absent gene underlies. . . " Nat. Genet., 1997;15:157-164.
Aken et al. "The Ensembl gene annotation system" Databse (Oxford), 2016.
Akerman et al., "A computational approach for genome-wide mapping of splicing factor binding sites" Genome Biol., 2009;10:R30.
Barone et al., "Inhibition of Induced Endochondral Bone Development in Caffeine-Treated Rats" J. Cell Biochem., 1993;52:171-182.
Bechtel et al., "Methylation determines fibroblast activation and fibrogenesis in the kidney" Nat. Med., 2010;16(5):544-550.
Bonner et al., "yH2AX and cancer" Nat. Rev. Cancer, 2008;8(12):957-967.
Bunting et al., "53BP1 inhibits homologous recombination in Brca1-deficient cells by blocking resection of DNA breaks" Cell, 2010;141(2):243-254.
The 1000 Genomes Project Consortium, "An integrated map of genetic variation from 1,092 human genomes" Nature, 2012;491:56-65.
Cook et al., "Tyrosine Dephosphorylation of H2AX Modulates Apoptosis and Survival Decisions" Nature, 2009;458(7238):591-596.
Elledge, "Cell Cycle Checkpoints: Preventing an Identity Crisis" Science, 1996;274:1664-1672.
Ju et al., "Tissue transcriptome-driven identification of epidermal growth factor as a chronic kidney disease biomarker" Sci. Transl. Med., 2015;7(316).
Kottgen et al., "Genome-wide association study for renal traits in the Framingham Heart and Atherosclerosis Risk in Communities Studies" BMC Med. Genet., 2008;9(49).
Krishnan et al., "Dephosphorylation of the C-terminal Tyrosul Residue of the DNA Damage-related Histone H2A.X. . . " J. Biol. Chem, 2009;284(24):16066-16070.
Krizhanovsky et al., "Senescence of Activated Stellate Cells Limits Liver Fibrosis" Cell, 2008;134:657-667.
Lebleu et al., "Origina and Function of Myofibroblasts in Kidney Fibrosis" Nat. Med., 2013;19(8):1047-1053.
Li et al., "Eya protein phosphatase activity regulates Six1-Dach-Eya. . . " Nature, 2003;426:247-254.
Li et al., "Inactivation of the SR Protein Splicing Factor ASF/SF2 Results in Genomic Instability" Cell, 2005;122:365-378.
Ling et al., "Conserved expression of natural antisense transcripts in mammals" BMC Genomics, 2013;14(243).
Liu et al., "Editing DNA methylation in the mammalian genome" Cell, 2016;167 (1):233-247.
Lovci et al., "Rbfox proteins regulate alternative mRNA splicing through evolutionarily conserved RNA bridges" Nat. Struct. Mol. Biol., 2013;20:1434-1442.
Vaidya et al., "Knock-In Reporter Mice Demonstrate that DNA Repair by Non-homologous End Joining Declines with Age" PLOS Genet., 2014;10(7).
Xu et al., "High-fidelity CRISPR/Cas9- based gene-specific hydroxymethylation rescues gene. . ." Nature Comm., 2018;9(1).
Zhou et al., "FAN1 mutations cause karyomegalic interstitial nephritis, linking chronic kidney. . ." Nat. Genet., 2013;44(8):910-915.
Zimmermann et al., "53BP1 regulates DSB repair using Rif1 to control 5' end resection" Science, 2013;339:700-704.

\* cited by examiner

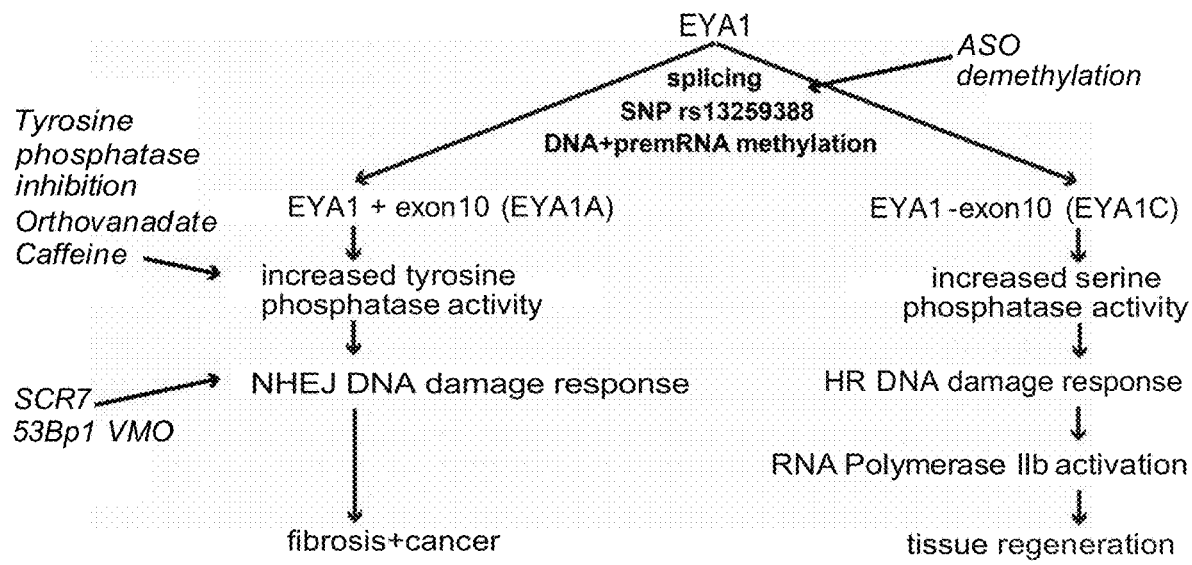
Fig. 1
Fig. 2A
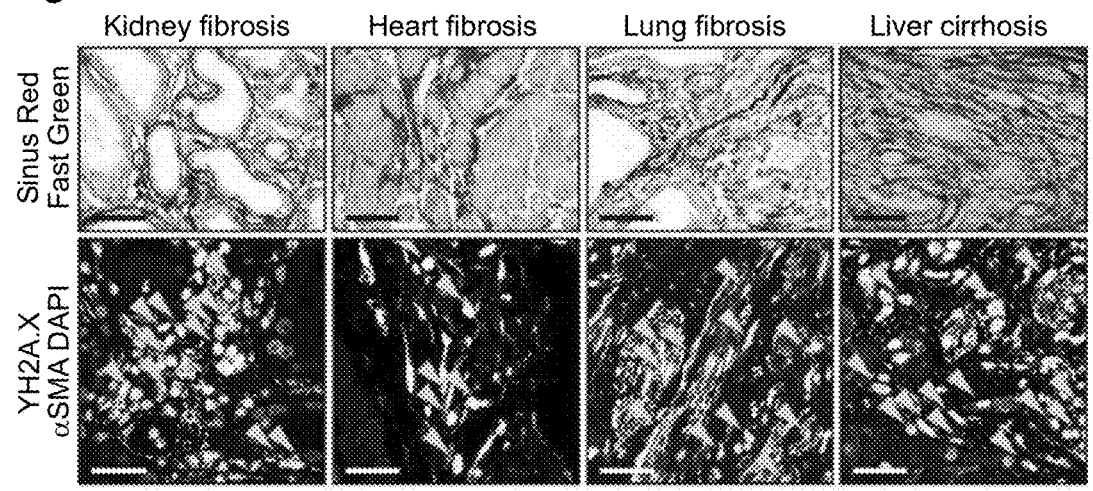
Fig. 2B
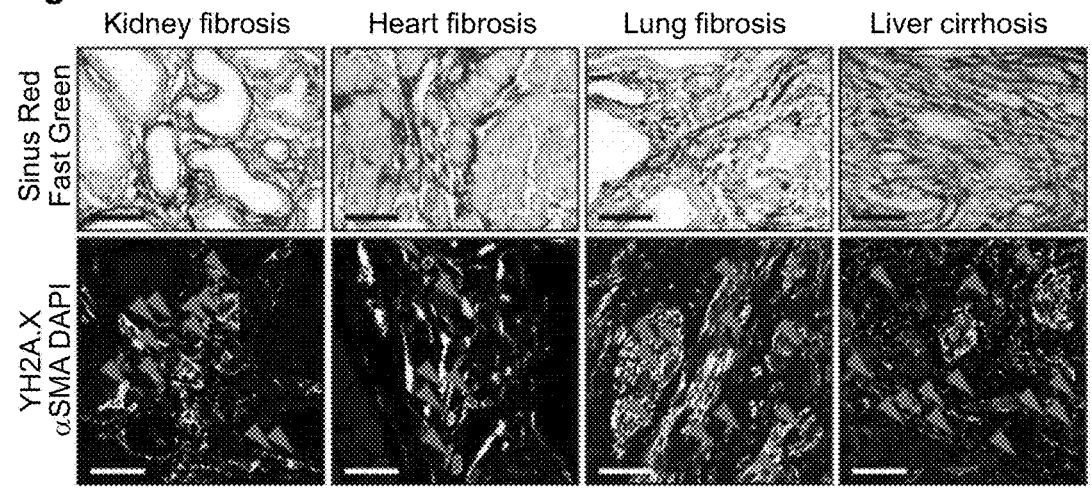

Fig. 2C
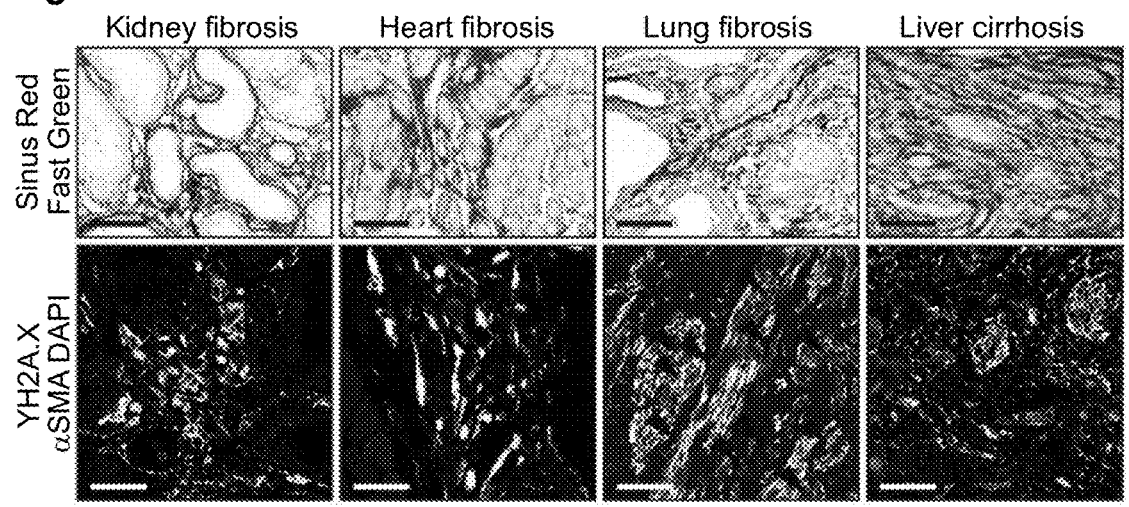
Fig. 2D
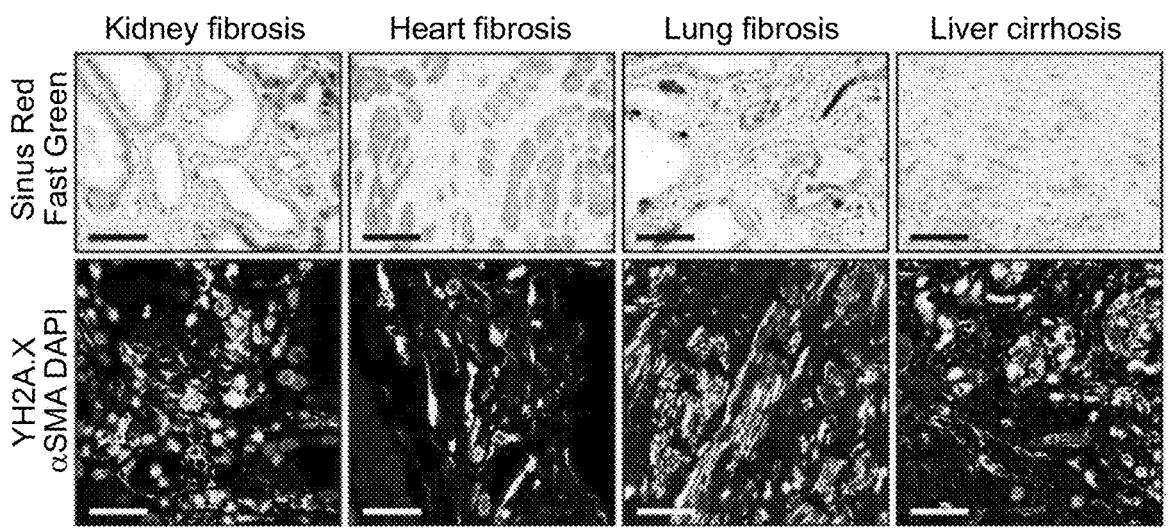
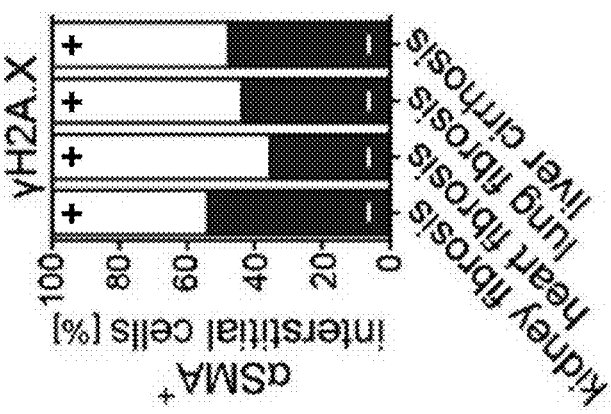

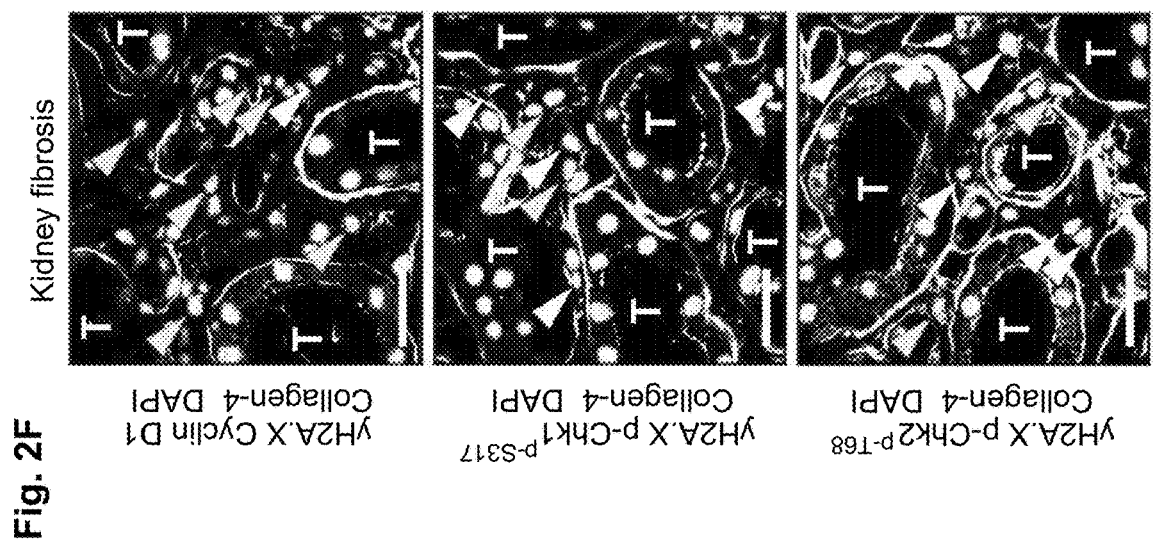
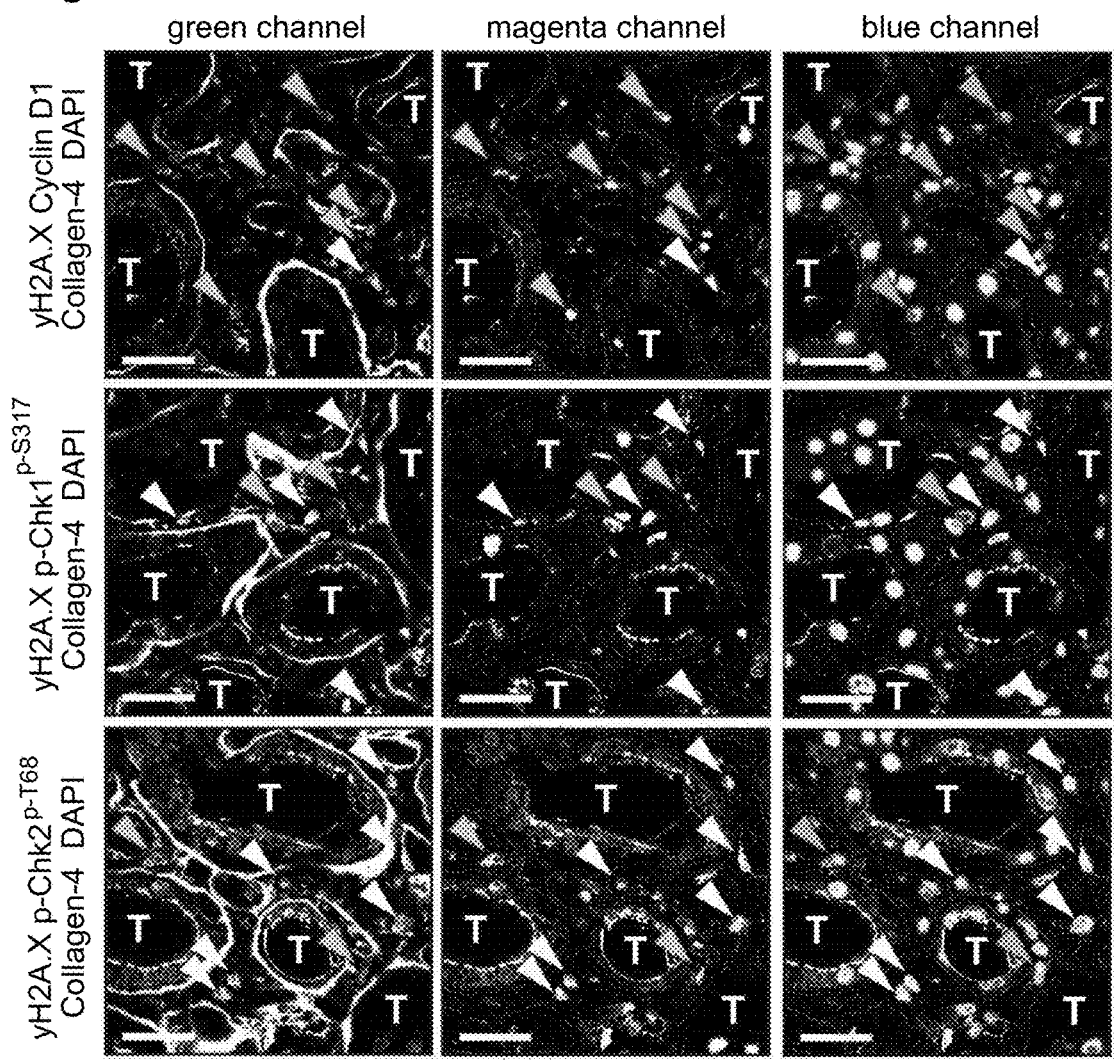

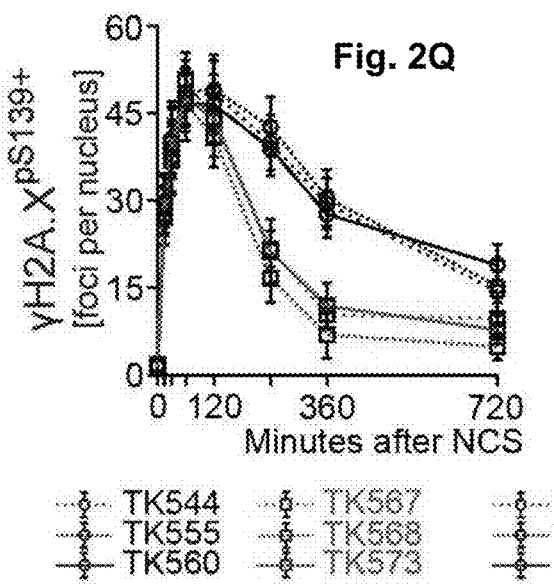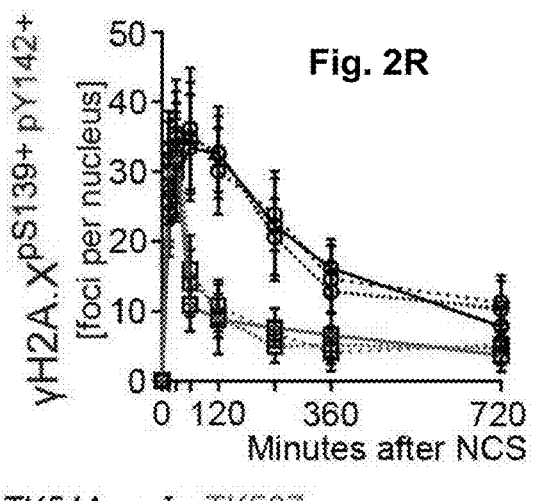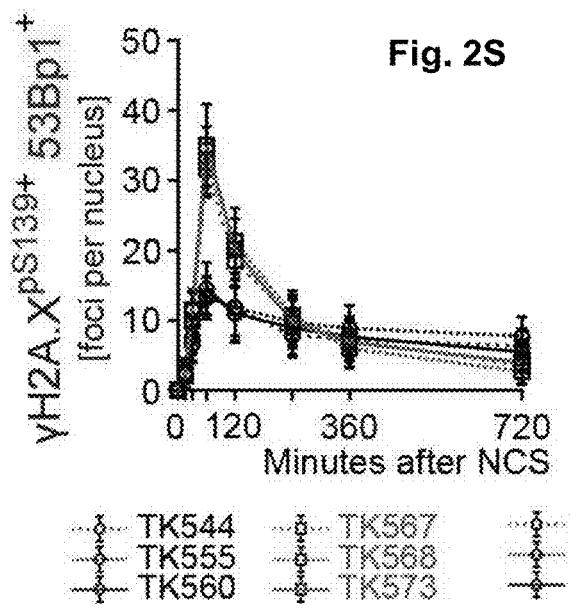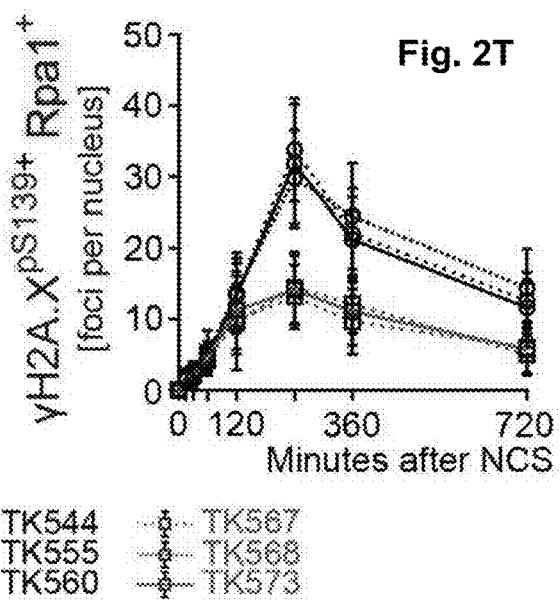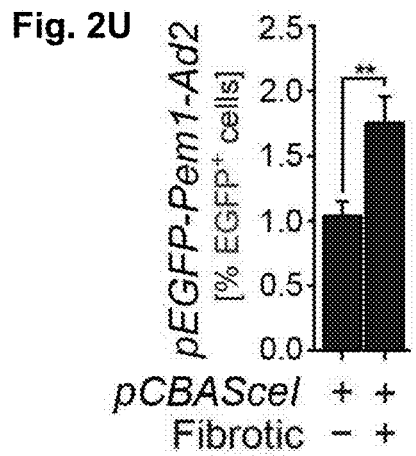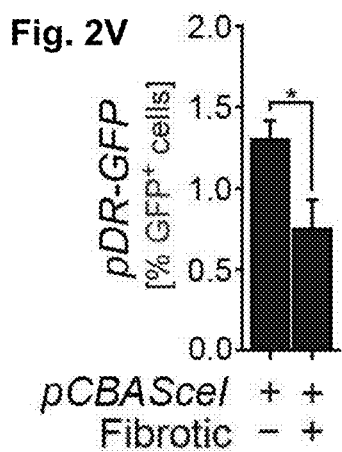

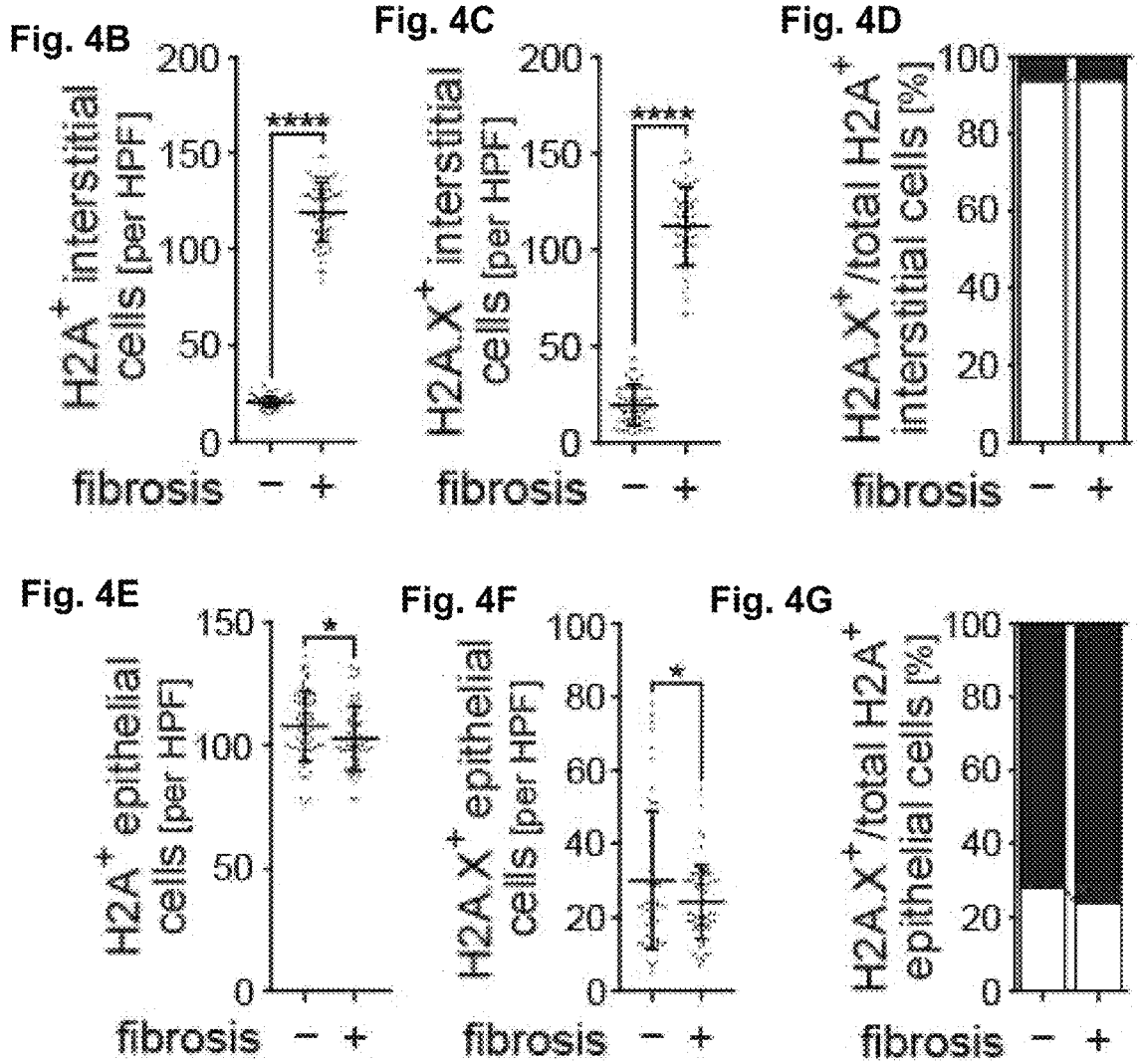
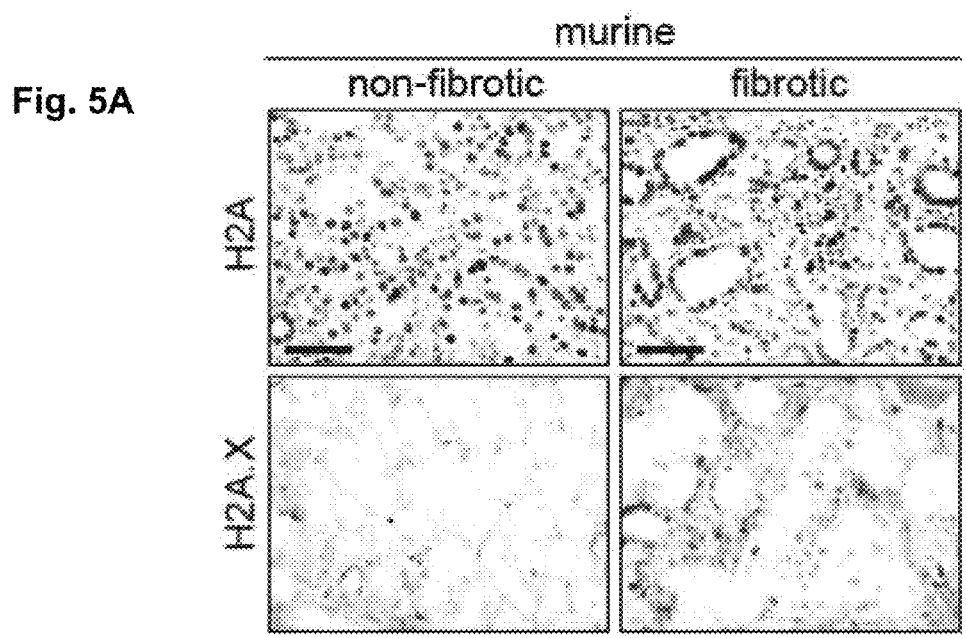

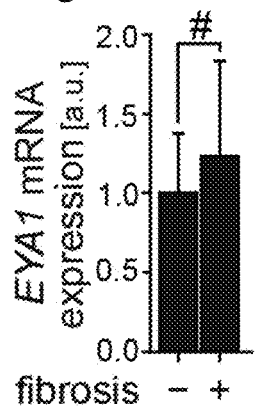
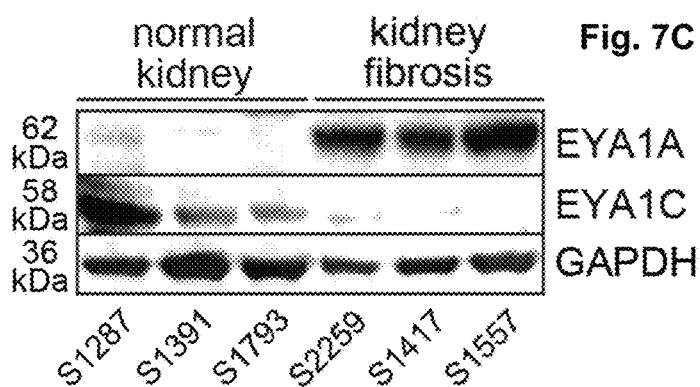
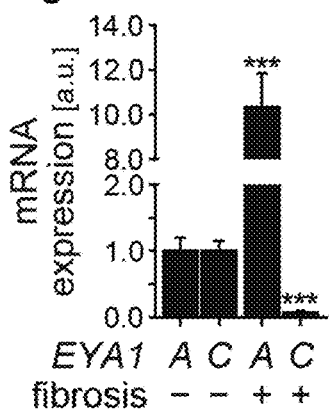
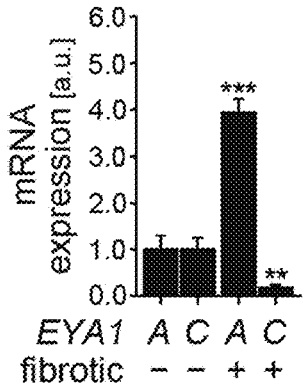
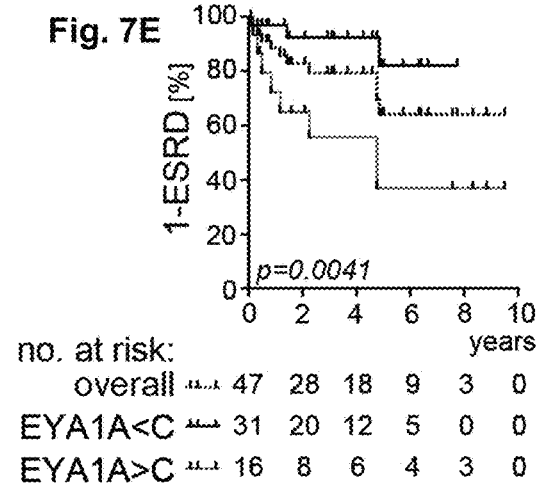
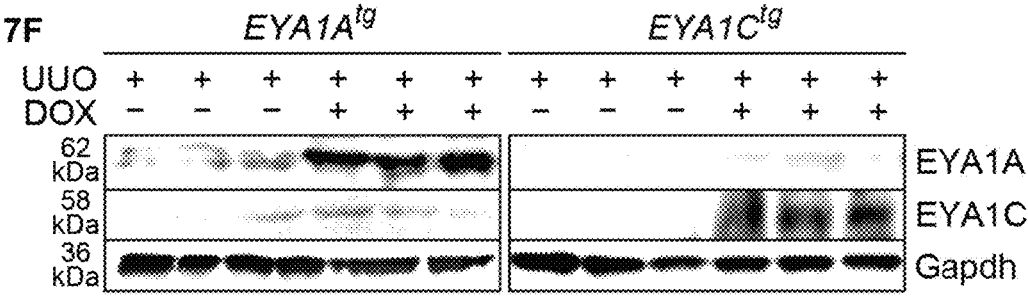
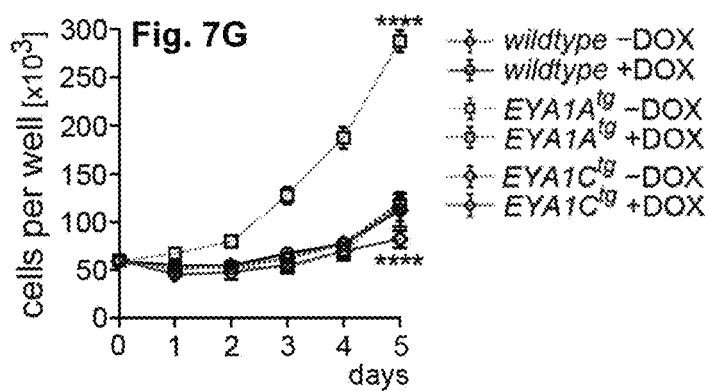
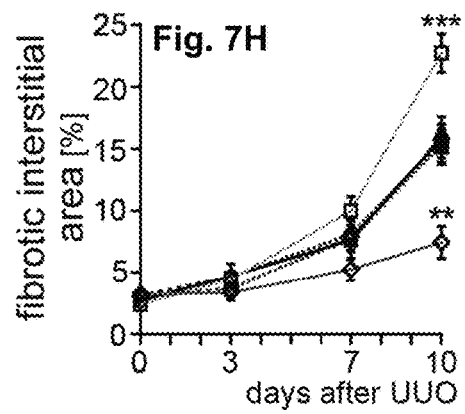

|  | EYA1A[tg] | | | |
|---|---|---|---|---|
| UUO | + | + | + | + |
| DOX | − | − | + | + |
| SCR7 | − | + | − | + |

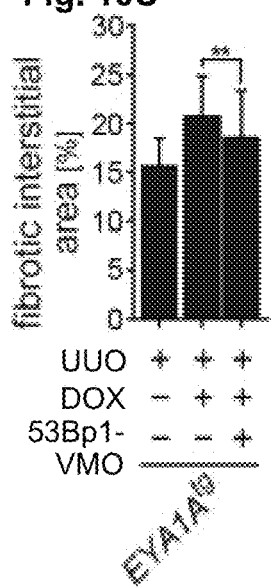
Fig. 10U
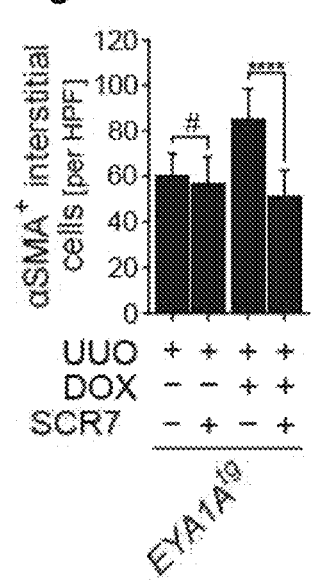
Fig. 10V
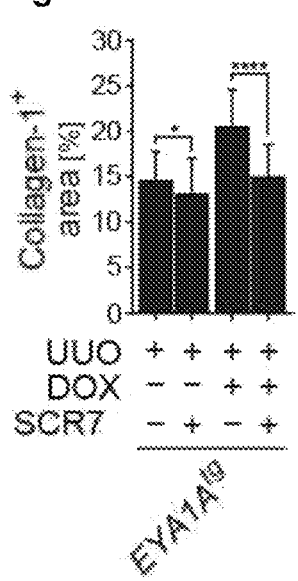
Fig. 10W
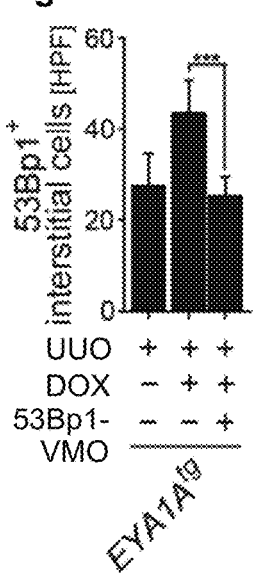
Fig. 10X
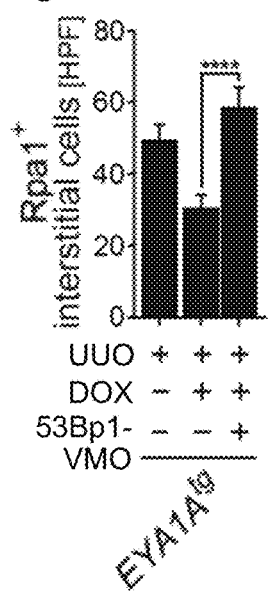
Fig. 10Y
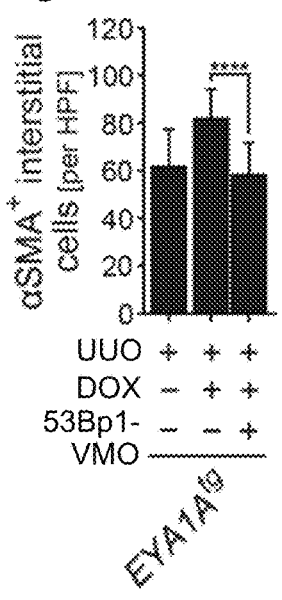
Fig. 10Z
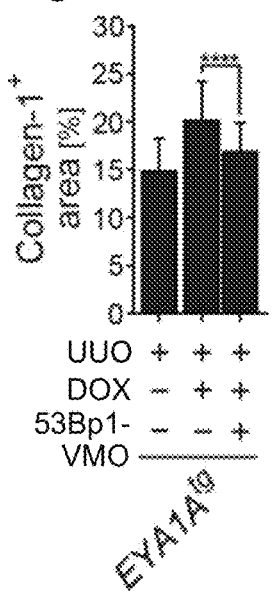
Fig. 10Z1
Fig. 11A
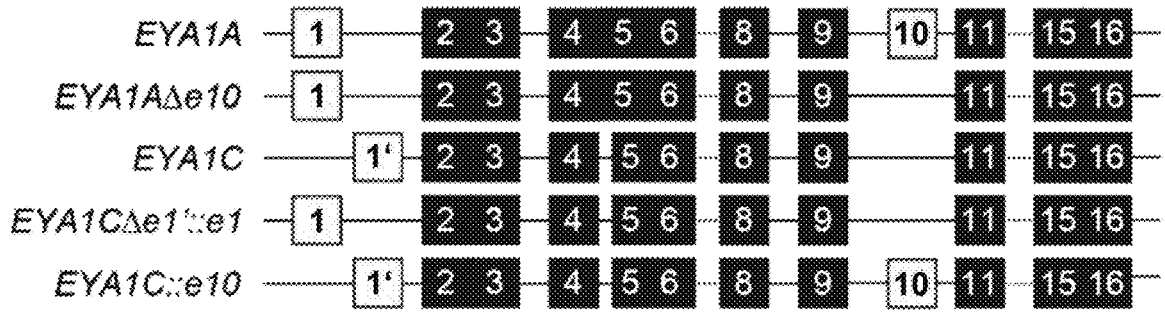

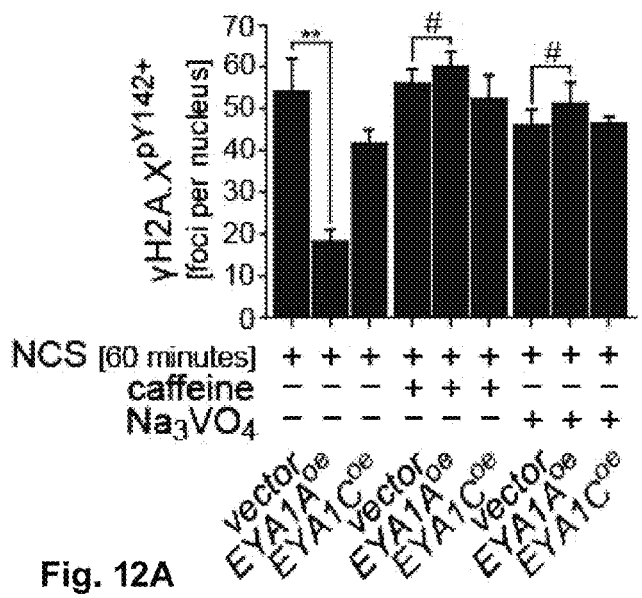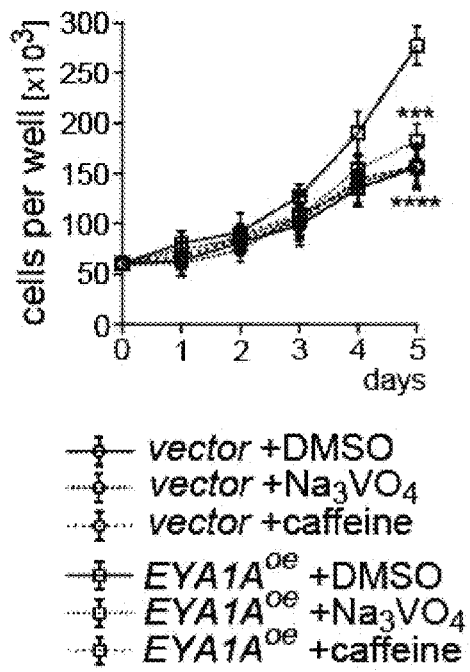
Fig. 12A
Fig. 12B
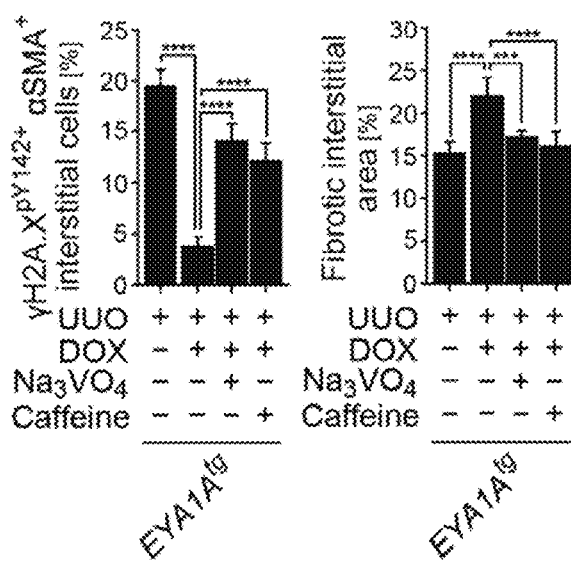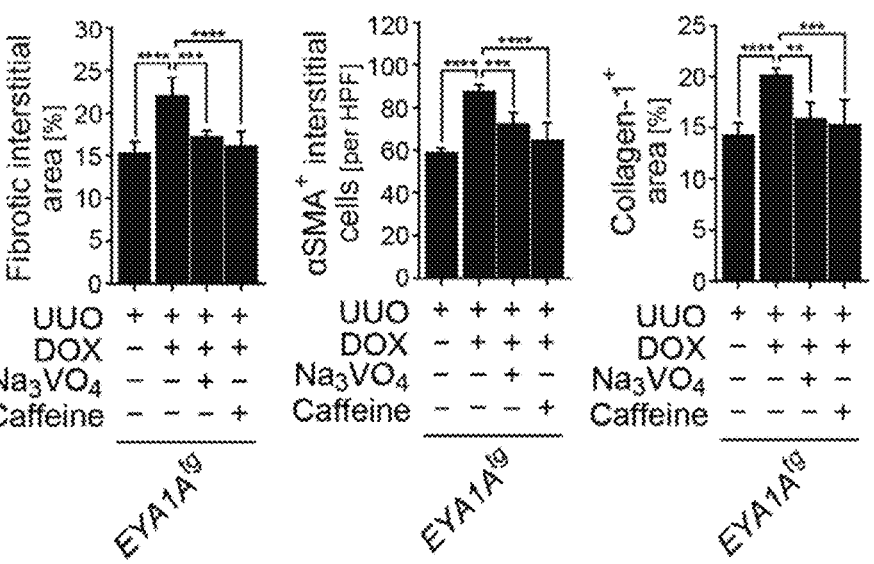
Fig. 13A  Fig. 13B  Fig. 13C  Fig. 13D

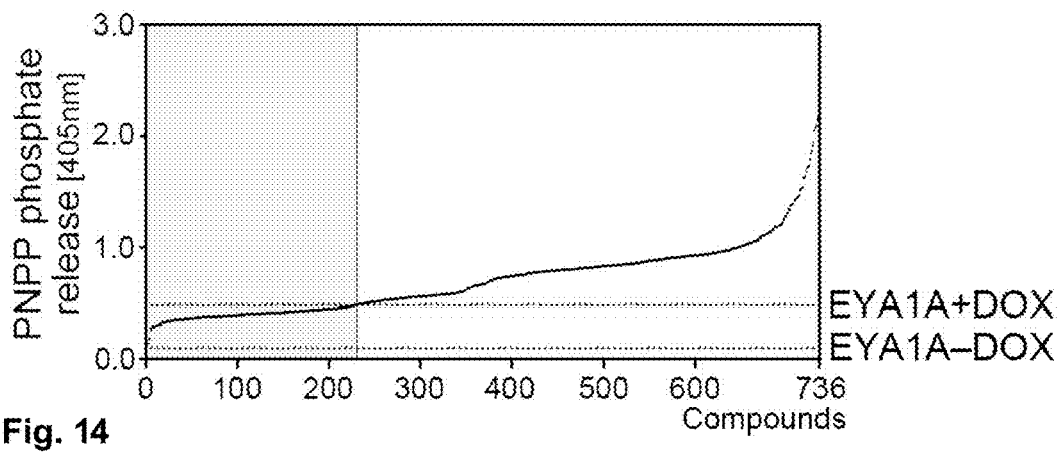
Fig. 14
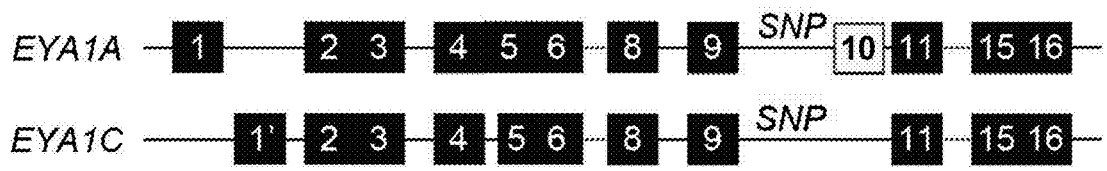
Fig. 15A
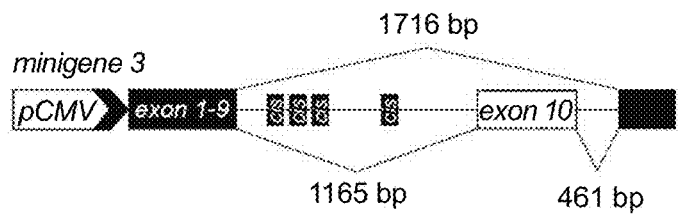
Fig. 15B
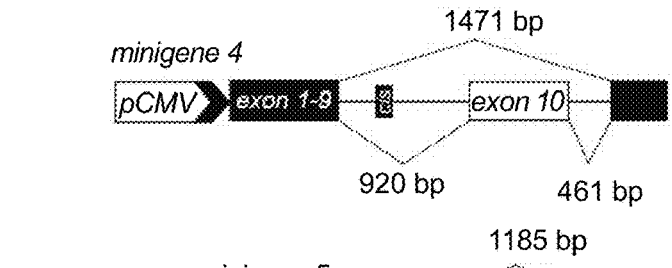
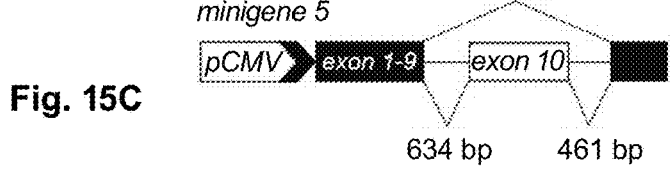
Fig. 15C
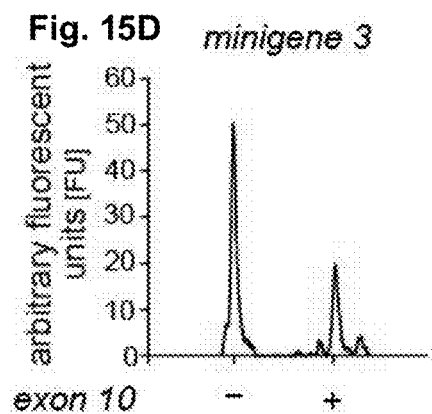
Fig. 15D *minigene 3*
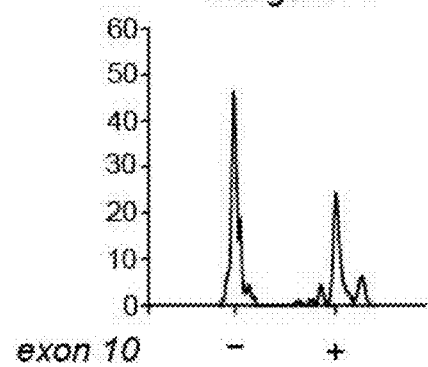
Fig. 15E *minigene 4*

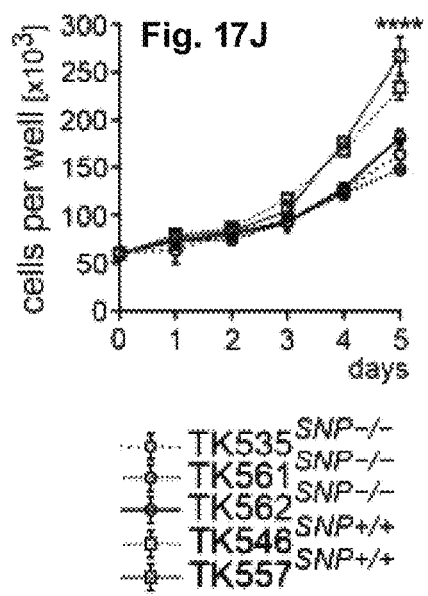
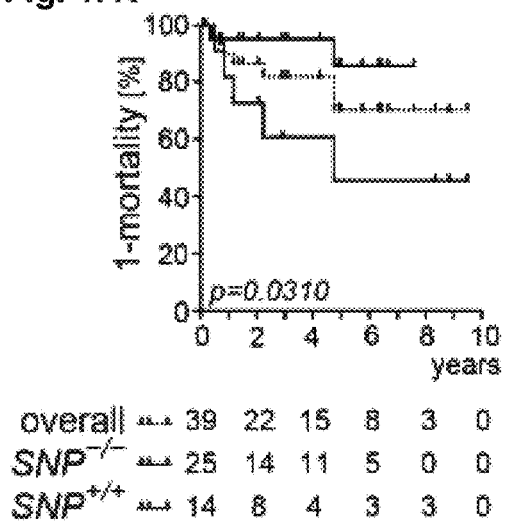
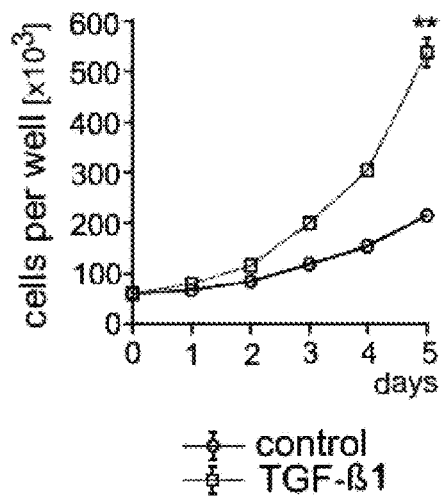
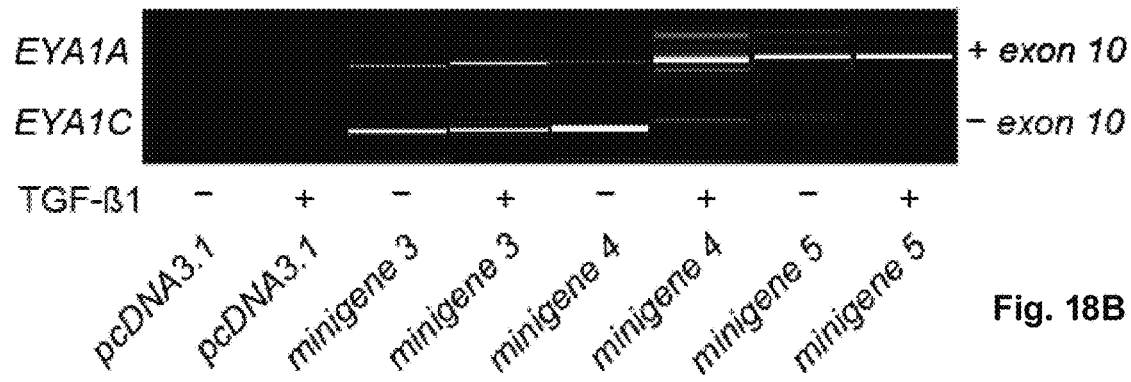

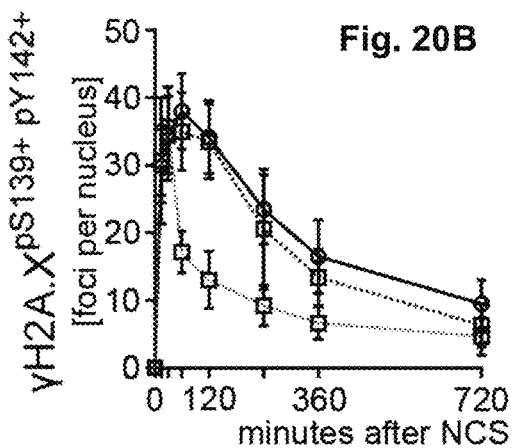
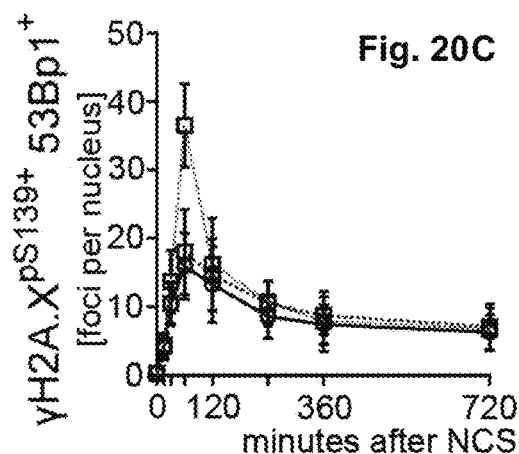
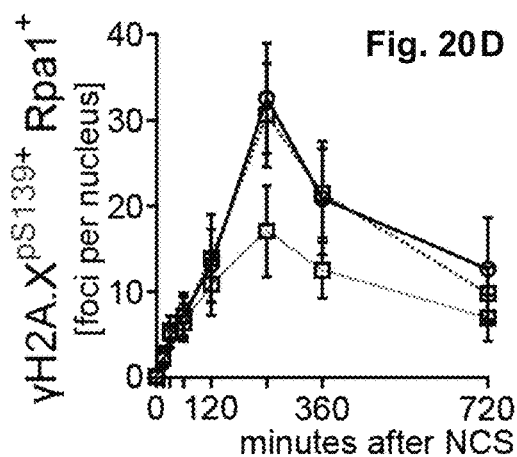
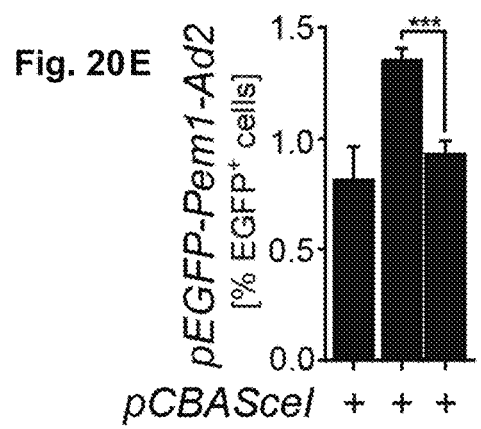
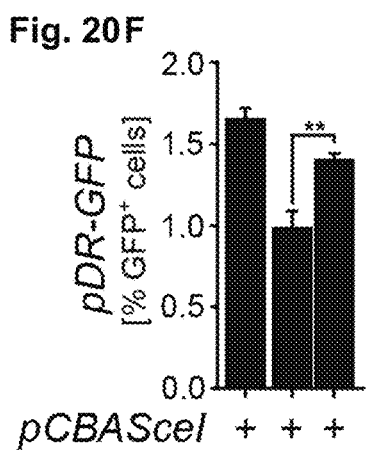
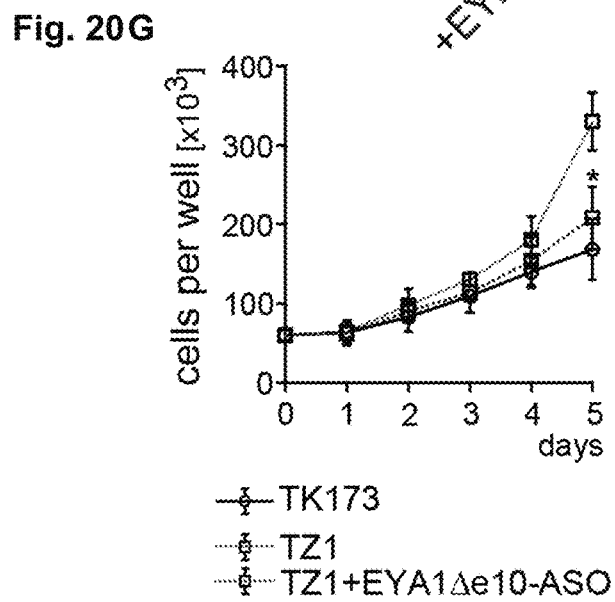

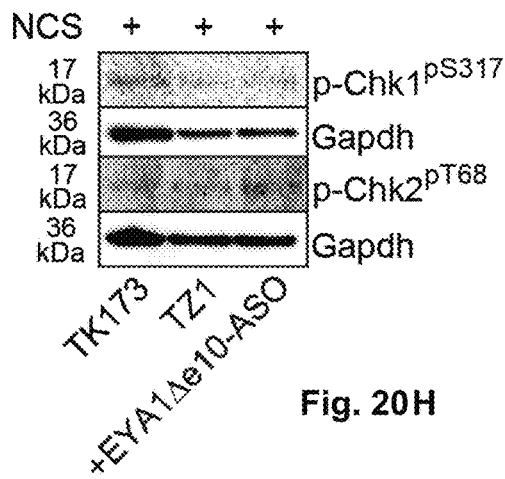
Fig. 20H
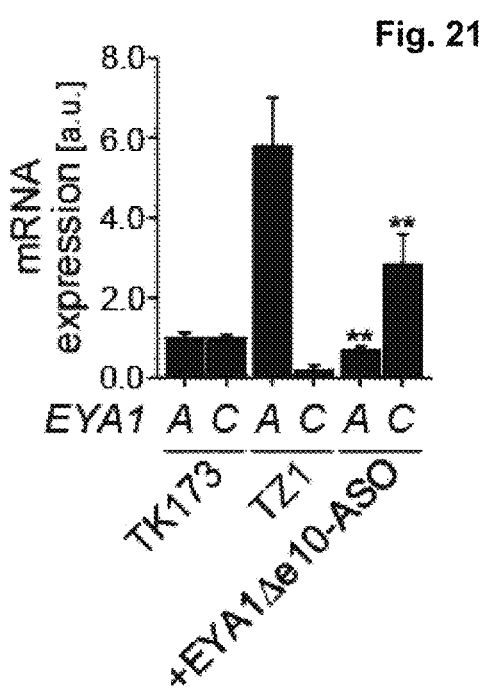
Fig. 21
Fig. 22
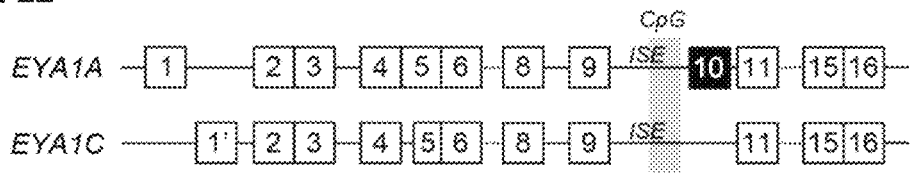
Fig. 23A
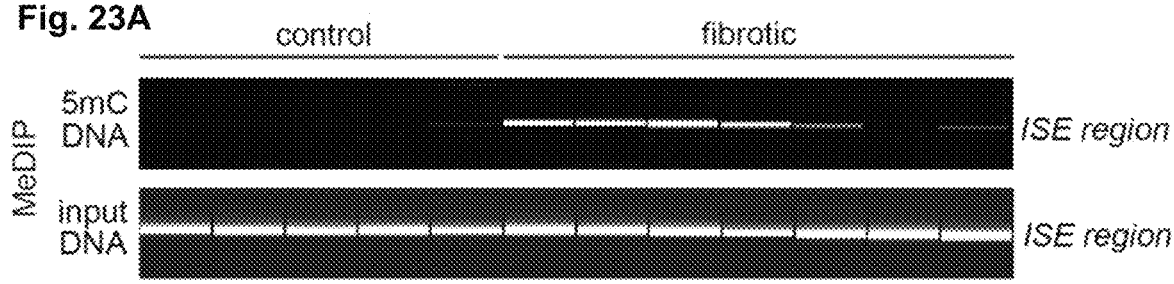
Fig. 23B
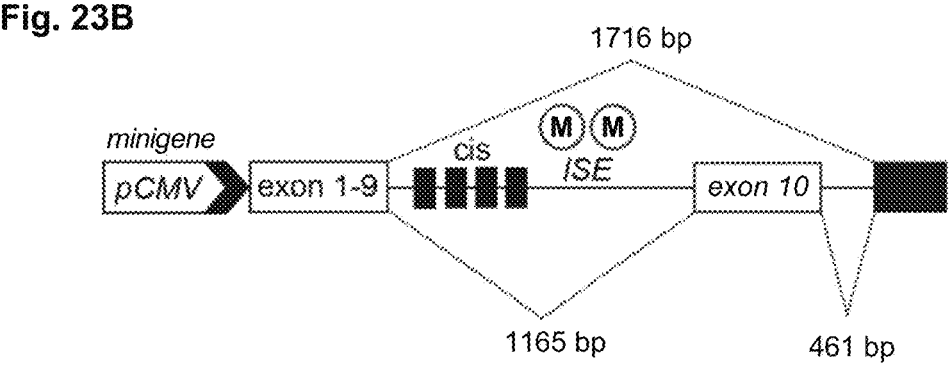

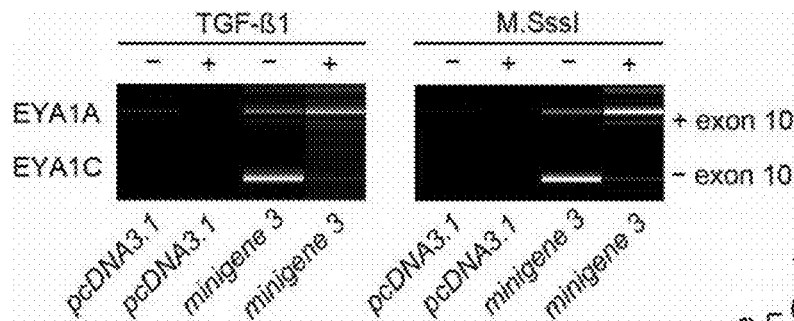

Fig. 23C

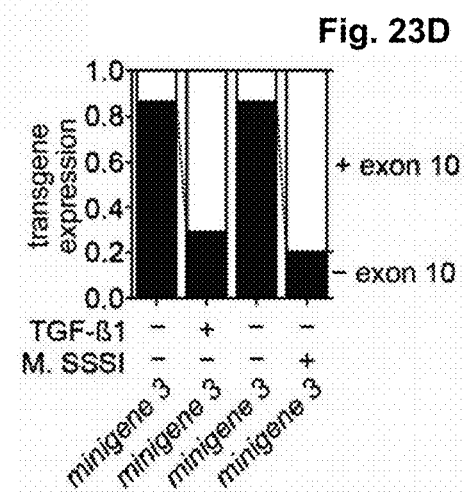

Fig. 23D

Fig. 24 (SEQ ID NO: 1)

```
MLLFPQVA VK  TEPMSSSETA  STTADGSLNN  FSGSAIGSSS  FSPRPTHQFS
PPQIYPSNRP  YPHILPTPSS   QTMAAYGQTQ  FTTGMQQATA  YATYPQPGQP
YGISSYG ALW AG IKTEGGLS  QSQSPGQTGF  LSYGTSFSTP  QPGQAPYSYQ
MQGSSFTTSS  GIYTGNNSLT   NSSGFNSSQQ  DYPSYPSFGQ  GQYAQYYNSS
PYPAHYMTSS  NTSPTTPSTN   ATYQLQEPPS  GITSQAVTDP  TAEYSTIHSP
STPIKDSDSD  RLRRGSDGKS   RGRGRRNNNP  SPPPDSDLER  VFIWDLDETI
IVFHSLLTGS  YANRYGR DPP  TSVSLGLRME  EMIFNLADTH  LFFNDLEE CD
QVHIDDVSSD  DNGQDLSTYN   FGTDGFPAAA  TSANLCLATG  VRGGVDWMRK
LAFRYRRVKE  IYNTYKNNVG   GLLGPAKREA  WLQLRAEIEA  LTDSWLTLAL
KALSLIHSRT  NCVNILVTTT   QLIPALAKVL  LYGLGIVFPI  ENIYSATKIG
KESCFERIIQ  RFGRKVVYVV   IGDGVEEEQG  AKKHAMPFWR  ISSHSDLMAL
HHALELEYL
```

```
MEMQDLTSPH  SRLSGSSESP   SGPKLGNSHI  NSNSMTPNGT  E VKTEPMSSS
ETASTTADGS  LNNFSGSAIG   SSSFSPRPTH  QFSPPQIYPS  NRPYPHILPT
PSSQTMAAYG  QTQFTTGMQQ   ATAYATYPQP  GQPYGISSYG  IKTEGGLSQS
QSPGQTGFLS  YGTSFSTPQP   GQAPYSYQMQ  GSSFTTSSGI  YTGNNSLTNS
SGFNSSQQDY  PSYPSFGQGQ   YAQYYNSSPY  PAHYMTSSNT  SPTTPSTNAT
YQLQEPPSGI  TSQAVTDPTA   EYSTIHSPST  PIKDSDSDRL  RRGSDGKSRG
RGRRNNNPSP  PPDSDLERVF   IWDLDETIIV  FHSLLTGSYA  NRYGRECDQV
HIDDVSSDDN  GQDLSTYNFG   TDGFPAAATS  ANLCLATGVR  GGVDWMRKLA
FRYRRVKEIY  NTYKNNVGGL   LGPAKREAWL  QLRAEIEALT  DSWLTLALKA
LSLIHSRTNC  VNILVTTTQL   IPALAKVLLY  GLGIVFPIEN  IYSATKIGKE
SCFERIIQRF  GRKVVYVIG    DGVEEEQGAK  KHAMPFWRIS  SHSDLMALHH
ALELEYL
```

Fig. 25 (SEQ ID NO: 50)

Fig. 26   IIVFHSLLTG SYANRYGR

Fig. 27   SSFTTSSGI YTGNNSLTNS SGFNSS

Fig. 28

IKTEGGLSQS QSPGQTGFLS YGTSFSTPQP GQAPYSYQMQ GSSFTTSSGI YTGNNSLTNS
SGFNSSQQDY PSYPSFGQGQ YAQYYNSSPY PAHYMTSSNT SPTTPSTNAT YQLQEPPSGI
TSQAVTDPTA EYSTIHSPST PIKDSDSDRL RRGSDGKSRG RGRRNNNPSP PPDSDLERVF
IWDLDETIIV FHSLLTGSYA NRYGR

Fig. 29   QVHIDDVSSD DNGQDLSTYN FGTDGFPAAA TSANLCLATG VRX$_1$GVX$_2$WMRK
LAFRYRX$_3$VKE IYNTYKNNVG GLLGPAKREA WLQLRAEIEA LTDSWLTLAL
KALX$_4$LIHSRT NCVNILVTTT QX$_5$IPALAKVL

Fig. 30   GATCCACCCA CTTCAGTTTC CCTTGGACTG CGAATGGAAG AAATGATTTT
CAACTTGGCA GACACACATT TATTTTTTAA TGACTTAGAA

Fig. 31   AAAAAAAAAA TCATCACTTA GGCCGGGCGC AGTGGCTCAT GCCTGTAATC
CCAGCACTTT GGGAGGCTGA GGCAGGCGGA TCATGAGGTC AGATCAAGAC
CATCCTGGCC AACATGGTGA AACTCCGTCT CTACTAAAAA TACAAAAAAA
AATTAGCTGG TCGTGTTGGT GCGCGCCTGT AGTCCCAGCT ACTCGGGAGG CTGA

Fig. 32   TTTTTTTTTT AGTAGTGAAT CCGGCCCGCG TCACCGAGTA CGGACATTAG
GGTCGTGAAA CCCTCCGACT CCGTCCGCCT AGTACTCCAG TCTAGTTCTG
GTAGGACCGG TTGTACCACT TTGAGGCAGA GATGATTTTT ATGTTTTTT
TTAATCGACC AGCACAACCA CGCGCGGACA TCAGGGTCGA TGAGCCCTCC GACT

|  |  | SEQ ID NO: |
|---|---|---|
| Homo sapiens | GTGTATTTTACGTGTGGCCTC | 42 |
| rs13259388 | GTGTATTTTATGTGTGGCCTC | 43 |
| Chimpanzee | GTGTATTTTATGTGTGGCCTC | 43 |
| Gorilla | GTGTACTTTATGTGTGGCCTC | 44 |
| Orangutan | GTGTATTTTATGTGTGGCCTC | 43 |
| Vervet | GTGTATTTTATGTGTTGCCTC | 45 |

Fig. 33A

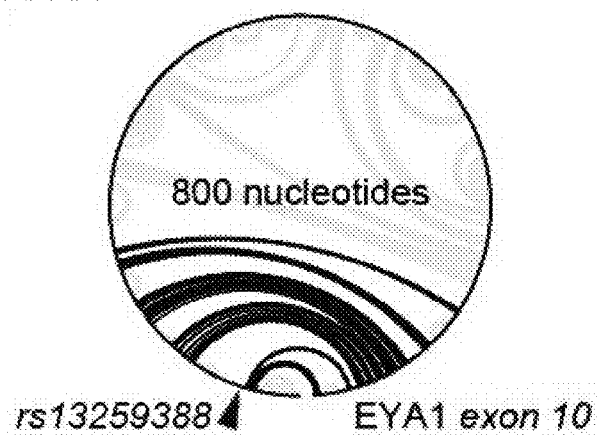

Fig. 33B

Fig. 33C  AGTGTTAGTGTATTTTA[C]GTGTGGCCTCAAACAAT

Fig. 35

| oligonucleotide | sequence | supplier | reference |
|---|---|---|---|
| mmActa2-F | SEQ ID NO: 23 | PrimerDesign | |
| mmActa2-R | SEQ ID NO: 24 | PrimerDesign | |
| mmCol1a1-F | SEQ ID NO: 25 | Eurofins | Bechtel et al., 2010 |
| mmCol1a1-R | SEQ ID NO: 26 | Eurofins | Bechtel et al., 2010 |
| mmGapdh | undislosed | PrimerDesign | |
| mmGapdh | undislosed | PrimerDesign | |
| hsEYA1 | undislosed | Applied Biosystems | |
| hsEYA1A | undislosed | Applied Biosystems | |
| hsEYA1C | undislosed | Applied Biosystems | |
| 18S | undislosed | Applied Biosystems | |

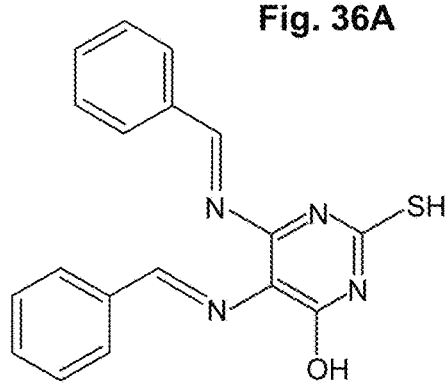

Fig. 36A

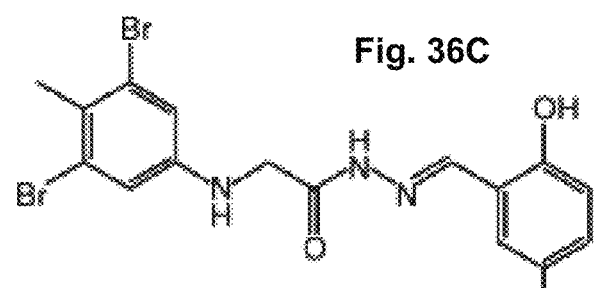

Fig. 36C

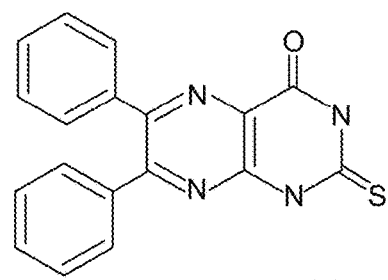

Fig. 36B

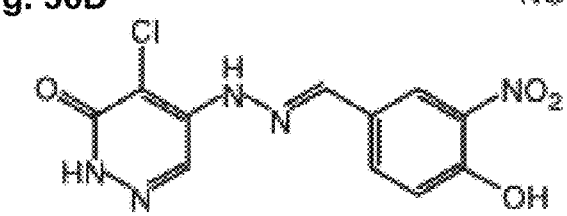

Fig. 36D

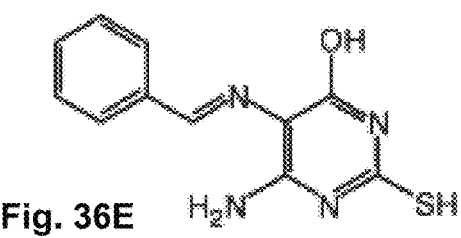

| in vivo morpholino | sequence | SEQ ID NO |
|---|---|---|
| control-VMO | 5'-CCTCTTACCTCAGTTACAATTTATA-3' | 16 |
| EYA1A-VMO | 5'-CTGCAACTTGAGGAAACAGCAACAT-3' | 9 |
| 53Bp1-VMO | 5'-TCCATCTGCTCCCCTGGCATCC-3' | 10 |

Fig. 38

| morpholino | sequence | SEQ ID NO |
|---|---|---|
| ASmotif-893WT | 5'-TTTTACGTGTGGCCTCAAACAATTC-3' | 33 |
| ASmotif-893SNP | 5'-GTGTATTTTATGTGTGGCCTCAAAC-3' | 29 |
| EYA1Δe10-5'ASO | 5'-[2OMeC]*C*C*T*T*G*G*A*C*T*G*C*G*A*A*T*G*[2OMeG-Q]-3' | 27 |
| EYA1Δe10-3'ASO | 5'-[2OMeU]*T*T*T*C*A*A*C*T*T*G*G*C*A*G*T*A*[2OMeA-Q]-3' | 14 |

Fig. 39 (SEQ ID NO: 51)

```
GATCCACCCA CTTCAGTTTC CCTTGGACTG CGAATGGAAG AAATGATTTT
CAACTTGGCA GACACACATT TATTTTTTAA TGACTTAGAA
```

TREATMENT OF ABERRANT FIBROBLAST PROLIFERATION

FIELD OF THE DISCLOSURE

Provided are means for preventing, treating and/or delaying progression of aberrant fibroblast proliferation such as fibrosis in a subject. Disclosed are in particular a method based on the use of a nucleic acid molecule and an antisense oligonucleotide, and a method based on the use of a nucleic acid ligase IV inhibitor, as well as the use of a phosphotyrosine phosphatase inhibitor. Disclosed is also a method based on the use of a nucleic acid molecule that includes an endonuclease 9 encoding sequence, a TET domain, and a sequence encoding an sgRNA molecule. Provided are furthermore methods of identifying a candidate compound suitable for treating fibrosis in a subject.

REFERENCE TO A SEQUENCE LISTING

This application includes a sequence listing.

BACKGROUND

The following discussion of the background is merely provided to aid the reader in understanding the invention and is not admitted to describe or constitute prior art to the present invention.

Fibroblasts are mesenchymal cells and the most common cell type of the connective tissues found throughout the body. They are the primary source of components of the extracellular matrix such as collagens, fibres, glycosaminoglycans and glycoproteins. Fibroblasts are also primarily responsible for remodeling in wound healing, and serve pivotal roles in inflammation, angiogenesis, cancer progression, and in physiological as well as pathological tissue fibrosis.

Excessive proliferation of fibroblasts is involved in numerous premalignant and malignant tumours, and cancer has been found to be associated with fibroblasts at all stages of disease progression, including metastasis. Fibroblasts are also regarded a considerable component of the general host response to tissue damage caused by cancer cells. Fibroblasts are furthermore involved in creating extracellular matrix structure and metabolic and immune reprogramming of the tumour microenvironment with an impact on adaptive resistance to chemotherapy.

40% of deaths worldwide are linked to fibrosis. Fibrosis typically follows inflammation or physical tissue injury, and is characterized by the formation of excessive fibrous connective tissue in an organ or tissue in a reparative or reactive process. In response to injury, for instance myocardial infarction, the process is called scarring. Fibrosis can impair tissue function and cause chronic diseases in a large variety of vital organs and tissues, including bone marrow. In skeletal muscle, fibrosis is typically associated with the muscular dystrophies. Fibrosis leads to destruction of organ architecture (Rockey, D. C., et al., N Engl J Med (2015) 372, 1138-1149; Tampe, D. & Zeisberg, M., Nat Rev Nephrol (2014) 10, 226-237).

Irreversible damage of parenchymal tissues going hand in hand with highly differentiated cells being replaced by scarring connective tissue leads to chronic failure of parenchymal organs such as the liver, kidney or the lungs. While a sufficient reserve of cells as well as mechanisms for repairing damaged areas are generally in place, in case of fibrosis tissue restoration is based on fibroblasts and functionally inappropriate connective tissue and thus loss of functional parenchyma. Fibroblasts are principal mediators of fibrosis. Fibrosis involves stimulated fibroblasts laying down connective tissue, and fibrogenesis is unequivocally associated with excessive fibroblast proliferation (Tampe & Zeisberg, 2014, supra; Bechtel, W, et al., Nat Med (2010) 16, 544-550; LeBleu, V. S., et al., Nat Med (2013) 19, 1047-1053; Rodemann, H. P & Muller, G. A., Proc Soc Exp Biol Med (1990) 195, 57-63).

The enhanced replicative stress and constant exposure to potentially genotoxic cellular metabolites can cause DNA damage, and DNA double-strand breaks (DSBs) are abundant within proliferating fibroblasts in chronic injury and fibrosis (Svegliati, S., et al., Sci Signal (2014) 7, ra84; Krizhanovsky, V, et al., Cell (2008) 134, 657-667; Zhou, W, et al., Nat Genet (2012) 44, 910-915). Abundant DNA damage, however, typically triggers cell cycle checkpoint activation, effectively pausing proliferation (Elledge, S. J., Science (1996) 274, 1664-1672). While parenchymal cells within chronically injured organs undergo permanent cell cycle arrest and senescence (Sturmlechner, I., et al., Nat Rev Nephrol (2017) 13, 77-89), it is not yet understood how fibroblasts can evade cell cycle arrest and sustain proliferative activity instead.

WO 2016/085981 suggests the use of isoprenoid compounds, in particular geranyl-geranylacetone, for inhibiting, reducing, or treating fibrosis. WO 2016/046130 suggests the use of a monoacylglycerol lipase (MGL) inhibitor. WO/2004/112565 teaches that the HNOEL-iso protein, which is localized in the ER, is a modulator in fibrosis. The document suggests the use of an inhibitor of the HNOEL-iso protein to reduce the proliferation of fibroblasts and to reduce or limit the formation of fibrotic regions in a tissue.

SUMMARY

The present disclosure provides methods that allow diagnosing and treating a disease involving aberrant fibroblast proliferation such as fibrosis or a tumor. These methods are based on the inventors' findings on the effect of the removal, vs. the lack thereof, of exon 10 of the gene encoding the protein EYA1. Provided are in particular means of controlling the formation of the EYA1 protein in such a way that it does not include exon 10. Provided are also screening methods for an agent suitable for treating a disease involving aberrant fibroblast proliferation. A respective screening method may be a method of screening for an agent suitable for controlling the formation of the EYA1 protein in such a way that it does not include exon 10.

The present disclosure provides methods that allow diagnosing and treating a disease involving aberrant fibroblast proliferation These methods are based on the inventors' findings on the effect of the removal, vs. the lack thereof, of exon 10 of the gene encoding the protein EYA1. Provided are in particular means of controlling the formation of the EYA1 protein in such a way that it does not include exon 10. Provided are also screening methods for an agent suitable for treating a disease involving aberrant fibroblast proliferation, e.g. fibrosis. A respective screening method may be a method of screening for an agent suitable for controlling the formation of the EYA1 protein in such a way that it does not include exon 10.

Provided is a method of preventing, treating or delaying onset or progression of a disease that involves aberrant fibroblast proliferation in a parenchymal organ. The method includes administering one or more of (i) a compound that reduces the level of tyrosine phosphatase activity effected by the protein EYA1A in the parenchymal organ, (ii) a nucleic acid ligase IV inhibitor, or (iii) an antisense oligonucleotide against the p53-binding protein 1 (53BP1).

In some embodiments a method as disclosed herein includes administering a compound that reduces the level of the protein EYA1A. Put differently, compared to a state without the method being carried out, on the protein level less EYA1A is detectable. In some embodiments less EYA1A is detectable in a parenchymal organ of a subject. In some embodiments a method as disclosed herein includes administering a compound that effects the removal of exon 10 during splicing of a transcript of the Eya1 gene. Thereby the ratio between EYA1A and EYA1C is shifted toward EYA1C. In some embodiments the ratio between EYA1A and EYA1C is shifted toward EYA1C in a parenchymal organ of a subject. In some embodiments a method as disclosed herein includes administering an inhibitor of the phosphotyrosine phosphatase activity of EYA1A.

In some embodiments the aberrant fibroblast proliferation includes desmoplasia and/or fibrosis.

According to a first aspect, there is provided a method of prevention, treatment or delaying onset or delaying progression of a disease that involves aberrant fibroblast proliferation. The method involves using one or more compounds of (i) an antisense oligonucleotide against a splice junction in the gene encoding the protein EYA1, (ii) a nucleic acid ligase IV inhibitor, (iii) an antisense oligonucleotide against the p53-binding protein 1, (iv) an inhibitor of the phosphotyrosine phosphatase activity of the protein EYA1A, or (v) a nucleic acid molecule that includes an endonuclease 9 encoding sequence, a TET domain, and a sequence encoding an sgRNA specific for a portion of a CpG island of the gene encoding EYA1.

The antisense oligonucleotide against a splice junction in the gene encoding the protein EYA1 may be directed against a portion of at least 12 consecutive bases within the sequence of SEQ ID NO: 34 or a complement thereof. The antisense oligonucleotide may also be directed against a portion of at least 14 consecutive bases within the sequence of SEQ ID NO: 34 or a complement thereof. In some embodiments the antisense oligonucleotide against a splice junction in the gene encoding the protein EYA1 may be directed against at least 16 consecutive bases within the sequence of SEQ ID NO: 34.

The antisense oligonucleotide against a splice junction in the gene encoding the protein EYA1 may be directed against a portion of at least 12 consecutive bases within the sequence of SEQ ID NO: 35 or a complement thereof. The antisense oligonucleotide may also be directed against a portion of at least 14 consecutive bases within the sequence of SEQ ID NO: 35 or a complement thereof. In some embodiments the antisense oligonucleotide against a splice junction in the gene encoding the protein EYA1 may be directed against at least 16 consecutive bases within the sequence of SEQ ID NO: 35.

The nucleic acid ligase IV inhibitor may in some embodiments be SCR 5 or SCR 6. In some embodiments the nucleic acid ligase IV inhibitor may be SCR7. In some embodiments the nucleic acid ligase IV inhibitor may be SCR7 pyrazine or SCR 8. In some embodiments the nucleic acid ligase IV inhibitor may be SCR 9 or SCR 10. In some embodiments the nucleic acid ligase IV inhibitor may be SCR 11 or SCR 12. In some embodiments the nucleic acid ligase IV inhibitor may be SCR 13 or SCR14.

The antisense oligonucleotide against the p53-binding protein 1 may in some embodiments be directed against a portion of the sequence of SEQ ID NO: 31 or a complement thereof or against a portion of the sequence of SEQ ID NO: 32 or a complement thereof.

The inhibitor of the phosphotyrosine phosphatase activity of the protein EYA1A may in some embodiments be benzbromarone or a polyoxomolybdate phosphate complex, hexapotassium hexatriaconta-µ-oxooctadecaoxobis [µ9-[phosphato(3-)-κO:κO:κO:κO':κO':κO":κO":κO''':κO''']]octadeca-molybdate(6-). In some embodiments the inhibitor of the phosphotyrosine phosphatase activity of the protein EYA1A may be a salt having a cation of the formula

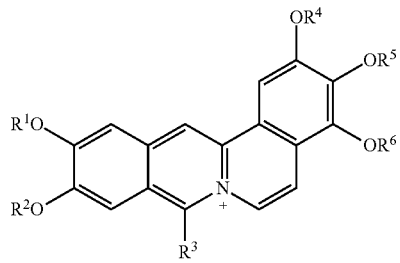

In this formula $R^1$ and $R^2$ are independently selected $C_1$-$C_6$ alkyl. $R^3$ is methyl or H. $R^4$, $R^5$ and $R^6$ are independently selected from H, methyl and ethyl.

In some embodiments the inhibitor of the phosphotyrosine phosphatase activity of the protein EYA1A may be a compound of the formula

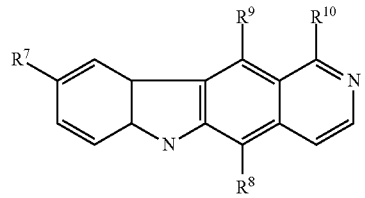

In this formula $R^7$ is H, OH, $C_1$-$C_6$ alkoxy or phenoxy. $R^8$ and $R^9$ are independently selected from H and methyl. $R^{10}$ is H, methyl, ethyl or (1-methyl-4-nitropyrazol-5-yl).

The sgRNA included in the nucleic acid molecule that includes an endonuclease 9 encoding sequence, a TET domain, and a sequence encoding an sgRNA specific for a portion of a CpG island of the gene encoding EYA1 may be specific for a sequence encoding an sgRNA specific for a portion of the sequence of one of SEQ ID NO: 6, 13, 21 or 33. Each of the endonuclease 9 encoding sequence and the TET domain included in the nucleic acid molecule are operably linked to a promoter. The promoters are independently selected from one another.

In some embodiments aberrant fibroblast proliferation occurs in an organ. Typically, the organ is a parenchymal organ. The parenchymal organ is in some embodiments a kidney or a liver. In some embodiments the parenchymal organ is a heart or a lung. In some embodiments the parenchymal organ is a spleen or a pancreas.

In some embodiments aberrant fibroblast proliferation occurs in a desmoplasia, such as a cancer. The desmoplasia is in some embodiments a prostate cancer or a breast cancer. In some embodiments the desmoplasia is a desmoplastic malignant melanoma or a desmoplastic squamous cell carcinoma. In some embodiments the desmoplasia is a morpheaform basal cell carcinoma or a microcystic adnexal carcinoma. In some embodiments the desmoplasia is a cutaneous leiomyosarcoma or a cutaneous metastasis.

In some embodiments the compound used is capable of preventing or stopping impairment of organ function or histopathological patterns of chronified injury before, during, or after injury. Histopathological patterns of chronified injury include in some embodiments at least one of fibrosis and cirrhosis. In some embodiments, histopathological patterns of chronified injury include at least one of loss of functional parenchyma and atrophy.

In some embodiments the disease involving aberrant fibroblast proliferation is fibrosis. In some embodiments, the compound used is capable of at least one of preventing, treating or delaying progression to fibrosis. In some embodiments the fibrosis is cystic fibrosis or idiopathic pulmonary fibrosis. In some embodiments the fibrosis is liver cirrhosis or artrial fibrosis of the heart. In some embodiments the fibrosis is endomyocardial fibrosis or glial scar of the brain. In some embodiments the fibrosis is keloid of the skin or Crohn's disease.

The compound of the present disclosure may also be advantageously applied in the prevention, treatment, and/or in delaying progression of chronic cardiac injury. In some embodiments, the compound is for use in the treatment of prevention of diabetes mellitus, in particular diabetic end-organ damage, including diabetic nephropathy.

In some embodiments, the compound used is capable of at least one of preventing, treating delaying onset or delaying progression of chronic kidney disease. In some embodiments, the compound used is capable of at least one of preventing, treating or delaying progression of chronic cardiac injury. In some embodiments, the compound used is capable of at least one of preventing, treating or delaying progression to end-stage renal disease. In some embodiments, the compound used is capable of at least one of preventing, treating or delaying progression to progression of pulmonary fibrosis. In some embodiments, the compound used is capable of at least one of preventing, treating or delaying progression to diabetes mellitus, including diabetic end-organ damage. In some embodiments, the compound used is capable of at least one of preventing, treating or delaying progression to diabetic nephropathy.

According to a second aspect, there is provided a method of preventing, treating, delaying onset or delaying progression of a disease involving aberrant fibroblast proliferation. The method includes administering to the subject an antisense oligonucleotide against a portion of at least 16 consecutive bases within the sequence of SEQ ID NO: 34, or a complement thereof, and/or an antisense oligonucleotide against a portion of at least 16 consecutive bases within the sequence of SEQ ID NO: 35, or a complement thereof. The antisense oligonucleotide against SEQ ID NO: 34 is directed against the splice junction of intron 9-10/exon 10 of the sequence encoding the protein EYA1. The antisense oligonucleotide against SEQ ID NO: 35 is directed against the splice junction of exon 10/intron 10-11 of the sequence encoding the protein EYA1. The sequence encoding the protein EYA1 can be found under GenBank accession number NG_011735.3. The exon termed exon 10 herein, is the twelfth exon listed in GenBank accession number NG_011735.3. The sequence of the reverse strand encoding the protein EYA1 can be found under Ensembl accession number ENSG00000104313 (Ensembl release 98 of September 2019), being the region 71,197,433-71,592,025 on human chromosome 8.

In some embodiments of the method according to the second aspect the antisense oligonucleotide against a portion of at least 16 consecutive bases within the sequence of SEQ ID NO: 34 is an antisense oligonucleotide against a sequence that includes the sequence of SEQ ID NO: 39 or a complement thereof. In some embodiments the antisense oligonucleotide against a portion of at least 16 consecutive bases within the sequence of SEQ ID NO: 34 is an antisense oligonucleotide against the sequence of SEQ ID NO: 39 or a complement thereof.

In some embodiments of the method according to the second aspect the antisense oligonucleotide against a portion of at least 16 consecutive bases within the sequence of SEQ ID NO: 34 is an antisense oligonucleotide against a sequence that includes the sequence of SEQ ID NO: 5 or a complement thereof. In some embodiments the antisense oligonucleotide against a portion of at least 16 consecutive bases within the sequence of SEQ ID NO: 34 is an antisense oligonucleotide against the sequence of SEQ ID NO: 5 or a complement thereof.

In some embodiments of the method according to the second aspect the antisense oligonucleotide against a portion of at least 16 consecutive bases within the sequence of SEQ ID NO: 35 is an antisense oligonucleotide against a sequence that includes one of the sequence of SEQ ID NO: 40, a complement thereof, a portion of the sequence SEQ ID NO: 40 or a complement of this portion. In some embodiments the antisense oligonucleotide against a portion of at least 16 consecutive bases within the sequence of SEQ ID NO: 35 is an antisense oligonucleotide against one of the sequence of SEQ ID NO: 40, a complement thereof, a portion of the sequence SEQ ID NO: 40 or a complement of this portion.

In some embodiments the antisense oligonucleotide against a portion against a sequence that includes one of the sequence of SEQ ID NO: 35, a complement thereof, a portion of the sequence SEQ ID NO: 35 or a complement of this portion is an antisense oligonucleotide against a sequence that includes the sequence of SEQ ID NO: 4, or a complement thereof. In some embodiments the antisense oligonucleotide against a portion against a sequence that includes one of the sequence of SEQ ID NO: 40, a complement thereof, a portion of the sequence SEQ ID NO: 40 or a complement of this portion is an antisense oligonucleotide against a sequence that includes the sequence of SEQ ID NO: 4, or a complement thereof.

In some embodiments of the method according to the second aspect the antisense oligonucleotide is a phosphorodiamidate morpholino oligonucleotide. In some embodiments the antisense oligonucleotide against at least a portion of SEQ ID NO: 39 and/or against at least a portion of SEQ ID NO: 35 furthermore includes a covalently linked octaguanidine dendrimer. In some embodiments the antisense oligonucleotide against SEQ ID NO: 5 and/or against SEQ ID NO: 4 furthermore includes a covalently linked octaguanidine dendrimer.

In some embodiments the subject expresses an EYA1 protein that includes the sequence of SEQ ID NO: 2. In some embodiments the subject expresses an EYA1 protein that includes the sequence of SEQ ID NO: 3. In some embodiments the subject expresses an EYA1 protein that includes the sequence of SEQ ID NO: 11. In some embodiments the subject expresses an EYA1 protein that includes the sequence of SEQ ID NO: 12. In some embodiments the subject expresses a naturally occurring EYA1 protein that includes the sequence of SEQ ID NO: 2. In some embodiments the subject expresses a naturally occurring EYA1 protein that includes the sequence of SEQ ID NO: 3. In some embodiments the subject expresses a naturally occurring EYA1 protein that includes the sequence of SEQ ID NO: 11. In some embodiments the subject expresses a naturally occurring EYA1 protein that includes the sequence of SEQ ID NO: 12. In some embodiments the subject expresses a naturally occurring EYA1 protein that includes the sequence of SEQ ID NO: 3. In some embodiments the subject expresses the human EYA1 protein. In some embodiments the subject is a human. In some embodiments the subject is a mouse or a rat. The mouse or the rat may express the human EYA1 protein that includes the sequence of SEQ ID NO: 2. The mouse or the rat may express the human EYA1 protein that includes the sequence of SEQ ID NO: 3. In some embodiments the mouse or the rat may express the human EYA1 protein that includes the sequence of SEQ ID NO: 11. The mouse or the rat may in some embodiments express the human EYA1 protein that includes the sequence of SEQ ID NO: 12.

According to a third aspect, there is provided a method of treating there is provided a method of preventing, treating, delaying onset or delaying progression of a disease involving aberrant fibroblast proliferation in a subject. The method includes administering to the subject an antisense oligonucleotide against the sequence of SEQ ID NO: 36 or a complement thereof. The antisense oligonucleotide inhibits translation of isoform A of the protein EYA1. Isoform A of the protein EYA1 is defined by the amino acid sequence of SEQ ID NO: 1, depicted in FIG. 24. In some embodiments the antisense oligonucleotide is an antisense oligonucleotide against SEQ ID NO: 9 or a complement thereof.

In some embodiments the method according to the third aspect includes administering to the subject an antisense oligonucleotide antisense oligonucleotide against a portion of at least 16 consecutive bases within the sequence of SEQ ID NO: 34, or a complement thereof, and/or an antisense oligonucleotide against a portion of at least 16 consecutive bases within the sequence of SEQ ID NO: 35, or a complement thereof. In some embodiments the method according to the third aspect includes administering to the subject an antisense oligonucleotide antisense oligonucleotide against a portion of at least 16 consecutive bases within the sequence of SEQ ID NO: 39, or a complement thereof, and/or an antisense oligonucleotide against a portion of at least 16 consecutive bases within the sequence of SEQ ID NO: 40, or a complement thereof. In some embodiments the method according to the third aspect includes administering to the subject an antisense oligonucleotide against SEQ ID NO: 5, or a complement thereof, and/or an antisense oligonucleotide against SEQ ID NO: 4, or a complement thereof.

In some embodiments of the method according to the third aspect the antisense oligonucleotide is a phosphorodiamidate morpholino oligonucleotide. In some embodiments the antisense oligonucleotide against SEQ ID NO: 9 furthermore includes a covalently linked octaguanidine dendrimer.

In some embodiments the subject expresses an EYA1 protein that includes the sequence of SEQ ID NO: 2. In some embodiments the subject expresses an EYA1 protein that includes the sequence of SEQ ID NO: 3. In some embodiments the subject expresses an EYA1 protein that includes the sequence of SEQ ID NO: 11. In some embodiments the subject expresses an EYA1 protein that includes the sequence of SEQ ID NO: 12. In some embodiments the subject expresses a naturally occurring EYA1 protein that includes the sequence of SEQ ID NO: 2. In some embodiments the subject expresses a naturally occurring EYA1 protein that includes the sequence of SEQ ID NO: 3. In some embodiments the subject expresses a naturally occurring EYA1 protein that includes the sequence of SEQ ID NO: 11. In some embodiments the subject expresses a naturally occurring EYA1 protein that includes the sequence of SEQ ID NO: 12. In some embodiments the subject expresses the human EYA1 protein. In some embodiments the subject is a human. In some embodiments the subject is a mouse or a rat. The mouse or the rat may express an EYA1 protein that includes the sequence of SEQ ID NO: 2. The mouse or the rat may express an EYA1 protein that includes the sequence of SEQ ID NO: 3. The mouse or the rat may express an EYA1 protein that includes the sequence of SEQ ID NO: 2. The mouse or the rat may express an EYA1 protein that includes the sequence of SEQ ID NO: 11. The mouse or the rat may express an EYA1 protein that includes the sequence of SEQ ID NO: 12. The EYA1 protein that includes the sequence of at least one of SEQ ID NO: 2, SEQ ID NO: 3, SEQ ID NO: 11 and SEQ ID NO: 12 may be a heterologous protein. The EYA1 protein that includes the sequence of at least one of SEQ ID NO: 2, SEQ ID NO: 3, SEQ ID NO: 11 and SEQ ID NO: 12 may be a recombinant protein.

The mouse or the rat may express a naturally occurring human EYA1 protein that includes the sequence of SEQ ID NO: 2. The mouse or the rat may express a naturally occurring human EYA1 protein that includes the sequence of SEQ ID NO: 3. The mouse or the rat may in some embodiments express the human EYA1 protein that includes the sequence of SEQ ID NO: 11. The mouse or the rat may in some embodiments express the human EYA1 protein that includes the sequence of SEQ ID NO: 12. The respective EYA1 protein may be a heterologous protein. The respective EYA1 protein may in some embodiments be a recombinant protein.

According to a fourth aspect, there is provided a method of preventing, treating, delaying onset or delaying progression of a disease involving aberrant fibroblast proliferation in a subject. The method includes administering to the subject one of the nucleic acid ligase IV inhibitors SCR 5 to SCR14 or SCR7 pyrazine, or an antisense oligonucleotide against the p53-binding protein 1 (53BP1). The method thereby involves inhibiting 53BP1.

In one embodiment the nucleic acid ligase IV inhibitor is SCR7.

In some embodiments of the method according to the fourth aspect the antisense oligonucleotide has the sequence of SEQ ID NO: 10.

In some embodiments of the method according to the fourth aspect the subject carries a nucleic acid sequence encoding the protein EYA1 which contains the amino acid sequence of SEQ ID NO: 3. The nucleic acid sequence encoding this protein furthermore includes the nucleic acid sequence of SEQ ID NO: 7 or the nucleic acid sequence of SEQ ID NO: 8. In some embodiments the subject carries the single nucleotide polymorphism (SNP) rs3259388. This SNP has been identified as a single nucleotide exchange, namely an exchange of G to A at base position 307546 of GenBank accession number NG_011735.3, located upstream of exon 10, the $12^{th}$ exon listed in the entry of GenBank accession number NG_011735.3. This SNP can be found in the Ensembl genome database (http://www.ensembl.org, Ensembl release 98 of September 2019) and in the NCBI database (https://www.ncbi.nlm.nih.gov/snp/rs3259388, build 153 dated 9 Jul. 2019), in both of which it is described as a C/T exchange on the forward strand of human chromosome 8, position 71245585, being a transcript variant within an intron. It has previously also been identified as rs61063790.

In some embodiments the subject carries a nucleic acid sequence encoding an EYA1 protein that includes SEQ ID NO: 2. In some embodiments the subject carries a nucleic acid sequence encoding an EYA1 protein that includes SEQ ID NO: 11. In some embodiments the subject carries a nucleic acid sequence encoding an EYA1 protein that includes SEQ ID NO: 12. In some embodiments the subject carries a nucleic acid sequence encoding a naturally occurring EYA1 protein that includes SEQ ID NO: 2. In some embodiments the subject carries a nucleic acid sequence encoding a naturally occurring EYA1 protein that includes SEQ ID NO: 11. In some embodiments the subject carries a nucleic acid sequence encoding a naturally occurring EYA1 protein that includes SEQ ID NO: 12

In some embodiments the subject carries a nucleic acid sequence encoding the human protein EYA1. In some embodiments the subject is a human. In some embodiments the subject is a mouse or a rat. The mouse or the rat may express the human EYA1 protein that includes the sequence of SEQ ID NO: 2. In some embodiments the mouse or the rat may express the human EYA1 protein that includes the sequence of SEQ ID NO: 3. The mouse or the rat may express the human EYA1 protein that includes the sequence of SEQ ID NO: 11. The mouse or the rat may in some embodiments the express the human EYA1 protein that includes the sequence of SEQ ID NO: 12. The respective EYA1 protein may be a heterologous protein. The respective EYA1 protein may in some embodiments be a recombinant protein.

In some embodiments of the method according to the fourth aspect the antisense oligonucleotide is a phosphorodiamidate morpholino oligonucleotide. In some embodiments the antisense oligonucleotide against SEQ ID NO: 10 furthermore includes a covalently linked octaguanidine dendrimer.

According to a fifth aspect, there is provided a method of preventing, treating, delaying onset or delaying progression of a disease involving aberrant fibroblast proliferation in a subject. The method includes administering to the subject a phosphotyrosine phosphatase inhibitor.

In some embodiments of the method according to the fifth aspect the phosphotyrosine phosphatase inhibitor is bis (maltolato)oxovanadium(IV) or benzbromarone. In some embodiments of the method according to the fifth aspect the phosphotyrosine phosphatase inhibitor is vanadate or caffeine.

In some embodiments the subject expresses a naturally occurring EYA1 protein that includes the sequence of SEQ ID NO: 2. In some embodiments the subject expresses a naturally occurring EYA1 protein that includes the sequence of SEQ ID NO: 3. In some embodiments the subject expresses a naturally occurring EYA1 protein that includes the sequence of SEQ ID NO: 11. In some embodiments the subject expresses a naturally occurring EYA1 protein that includes the sequence of SEQ ID NO: 12. In some embodiments the subject expresses a naturally occurring human EYA1 protein. In some embodiments the subject is a human. In some embodiments the subject is a mouse or a rat. The mouse or the rat may express a human EYA1 protein, including a naturally occurring human EYA1 protein, that includes the sequence of SEQ ID NO: 2. The mouse or the rat may express a human EYA1 protein, including a naturally occurring human EYA1 protein, that includes the sequence of SEQ ID NO: 3. In some embodiments the mouse or the rat may express the human EYA1 protein that includes the sequence of SEQ ID NO: 11. The mouse or the rat may in some embodiments the express a human EYA1 protein that includes the sequence of SEQ ID NO: 12. The respective EYA1 protein may be a heterologous protein. The respective EYA1 protein may in some embodiments be a recombinant protein.

In some embodiments of the method according to the fifth aspect the subject carries a nucleic acid sequence that encodes the protein EYA1, which contains SEQ ID NO: 3. In some embodiments of the method according to the fifth aspect the subject carries a nucleic acid sequence that encodes the protein EYA1, which contains SEQ ID NO: 2. The nucleic acid sequence encoding this protein furthermore includes the nucleic acid sequence of SEQ ID NO: 7 or the nucleic acid sequence of SEQ ID NO: 8. In some embodiments the subject carries the SNP rs3259388.

According to a sixth aspect, there is provided a method of assessing the risk of occurrence or progression of a disease involving aberrant fibroblast proliferation in a subject. The method involves determining in a sample from the subject the identity of one or more SNPs in the gene encoding the protein EYA1. Determining the one or more SNPs in the gene encoding the protein EYA1 includes determining the SNP at −893 bp upstream EYA1 exon 10 of the sequence encoding the protein EYA1. The base exchange can be found at position 71245585 on human chromosome 8 identified in Ensembl (see also below) by accession number ENSG00000104313. The presence of rs13259388 indicates the subject's increased risk of occurrence or progression of a disease involving aberrant fibroblast proliferation.

An increased risk of occurrence of a disease involving aberrant fibroblast proliferation in a subject may indicate that the subject has or develops a disease involving aberrant fibroblast proliferation. It may also indicate that such a disease progresses.

In some embodiments the subject expresses a naturally occurring EYA1 protein that includes the sequence of SEQ ID NO: 2. In some embodiments the subject expresses a naturally occurring EYA1 protein that includes the sequence of SEQ ID NO: 3. In some embodiments the subject expresses a naturally occurring EYA1 protein that includes the sequence of SEQ ID NO: 11. In some embodiments the subject expresses a naturally occurring EYA1 protein that includes the sequence of SEQ ID NO: 12. In some embodiments the subject expresses the human EYA1 protein. In some embodiments the subject is a human. In some embodiments the subject is a mouse or a rat. The mouse or the rat may express the human EYA1 protein that includes the sequence of SEQ ID NO: 2. The mouse or the rat may express the human EYA1 protein that includes the sequence of SEQ ID NO: 3. In some embodiments the mouse or the rat may express the human EYA1 protein that includes the sequence of SEQ ID NO: 11, see also above. The mouse or the rat may in some embodiments the express the human EYA1 protein that includes the sequence of SEQ ID NO: 12.

In some embodiments the disease involving aberrant fibroblast proliferation is a desmoplasia, such as a cancer. The desmoplasia is in some embodiments a prostate cancer or a breast cancer. In some embodiments the desmoplasia is a desmoplastic malignant melanoma or a desmoplastic squamous cell carcinoma. In some embodiments the desmoplasia is a morpheaform basal cell carcinoma or a microcystic adnexal carcinoma. In some embodiments the desmoplasia is a cutaneous leiomyosarcoma or a cutaneous metastasis. In some embodiments the disease involving aberrant fibroblast proliferation is pancreatic cancer or a gastric carcinoma. In some embodiments the disease involving aberrant fibroblast proliferation is lung cancer or a neuroblastoma.

In some embodiments of the method of the sixth aspect the disease involving aberrant fibroblast proliferation is fibrosis. The fibrosis is in some embodiments chronic kidney disease (CKD).

According to a seventh aspect, there is provided a method of assessing the risk of occurrence or progression of a disease involving aberrant fibroblast proliferation in a subject. The method involves determining in a sample from the subject the methylation status of a CpG island upstream exon 10 in the gene encoding the protein EYA1. The CpG island can be found at positions 307586 to 307789 of the NCBI reference sequence of GenBank accession number NG_011735, version 3 of the sequence as of 24 Feb. 2018. The CpG island is located at positions 71245342 to 71245545 of the forward strand of human chromosome 8 (see the Ensembl release 98 of September 2019 at http://www.ensembl.org/Homo_sapiens/Location/View?r=8:71245393-71245496;db=core). Elevated methylation of the CpG island indicates the subject's increased risk of occurrence or progression of a disease involving aberrant fibroblast proliferation such as fibrosis. A reduced or normal methylation of the CpG island indicates that the subject is not at an increased risk of occurrence or progression of a disease involving aberrant fibroblast proliferation.

In some embodiments the method of the seventh aspect includes comparing the methylation status of the CpG island to a reference. In some embodiments the method of the seventh aspect includes determining in a reference sample the methylation status of the CpG island found at the positions corresponding to positions 71245342 to 71245545 of the forward strand of human chromosome 8 (Ensembl release 98, supra) corresponding to positions 307586 to 307789 of GenBank accession number NG_011735, version 3. The reference sample may for instance be from one or more subjects known not to be at an increased risk of occurrence or progression of a disease involving aberrant fibroblast proliferation, e.g. fibrosis.

In some embodiments the subject expresses a naturally occurring EYA1 protein that includes the sequence of SEQ ID NO: 2. In some embodiments the subject expresses a naturally occurring EYA1 protein that includes the sequence of SEQ ID NO: 3. In some embodiments the subject expresses a naturally occurring EYA1 protein that includes the sequence of SEQ ID NO: 11. In some embodiments the subject expresses a naturally occurring EYA1 protein that includes the sequence of SEQ ID NO: 12. In some embodiments the subject expresses the human EYA1 protein. In some embodiments the subject is a human.

The CpG island has in some embodiments a sequence that is essentially identical to the sequence of SEQ ID NO: 6. In some embodiments the CpG island includes a sequence that is essentially identical to the sequence of SEQ ID NO: 6. In some embodiments the CpG island has a sequence that is defined by SEQ ID NO: 6.

In some embodiments the disease involving aberrant fibroblast proliferation is a desmoplasia, such as a cancer. The desmoplasia is in some embodiments a prostate cancer or a breast cancer. In some embodiments the desmoplasia is a desmoplastic malignant melanoma or a desmoplastic squamous cell carcinoma. In some embodiments the desmoplasia is a morpheaform basal cell carcinoma or a microcystic adnexal carcinoma. In some embodiments the desmoplasia is a cutaneous leiomyosarcoma or a cutaneous metastasis. In some embodiments the disease involving aberrant fibroblast proliferation is pancreatic cancer or colon cancer. In some embodiments the disease involving aberrant fibroblast proliferation is a neuroblastoma or lung cancer.

In some embodiments the disease involving aberrant fibroblast proliferation is fibrosis. The fibrosis is in some embodiments CKD.

An increased risk of occurrence of a disease involving aberrant fibroblast proliferation such as fibrosis in a subject may indicate that the subject has or develops a disease involving aberrant fibroblast proliferation.

According to an eight aspect, there is provided a nucleic acid molecule for use in a method of treating a disease involving aberrant fibroblast proliferation in a subject. The nucleic acid molecule includes an endonuclease 9 encoding sequence, a TET domain, and a sequence encoding an sgRNA. The sgRNA is specific for at least a portion of the sequence of SEQ ID NO: 6. Both the endonuclease 9 encoding sequence and the TET domain are operably linked to a promoter. The promoters are independently selected. The use includes administering the nucleic acid molecule to the subject.

In some embodiments the sgRNA specific for at least a portion of the sequence of SEQ ID NO: 6 is specific for a target sequence that has a length of 17 or more bases. In some embodiments the sgRNA is specific for a target sequence that has a length of 18 or more bases. In some embodiments the sgRNA has a length of 20 or more bases. In some embodiments the sgRNA is specific for a target sequence that is at least a portion of the sequence of SEQ ID NO: 46. In some embodiments the sgRNA is specific for a target sequence that is at least a portion of the sequence of SEQ ID NO: 47. In some embodiments the sgRNA is specific for a target sequence that is at least a portion of the sequence of SEQ ID NO: 48.

In some embodiments the disease involving aberrant fibroblast proliferation is a desmoplasia, such as a cancer. In some embodiments the disease involving aberrant fibroblast proliferation is fibrosis. In some embodiments the fibrosis is CKD.

According to a ninth aspect, there is provided a method of identifying a candidate compound for treating a disease involving aberrant fibroblast proliferation in a subject. The method includes contacting a nucleic acid molecule encoding the protein EYA1 with a test compound in a mammalian expression system. The mammalian expression system contains a nucleic acid molecule that includes the sequence encoding the protein EYA1. The sequence encoding the protein EYA1 is operably linked to a promoter. The sequence encoding the protein EYA1 includes the nucleic acid sequence of SEQ ID NO: 6, or the complement thereof. The method furthermore includes determining the methylation status of the sequence of SEQ ID NO: 6, or of the complement thereof, relative to a control. A reduced methylation level of SEQ ID NO: 6, or of the complement thereof, relative to the control indicates that the test compound is a candidate compound for treating a disease involving aberrant fibroblast proliferation in a subject. An increased or unchanged methylation level of SEQ ID NO: 6, or of the complement thereof, relative to the control indicates that the test compound is not a candidate compound for treating a disease involving aberrant fibroblast proliferation in a subject.

In some embodiments the subject expresses an EYA1 protein that includes the sequence of SEQ ID NO: 2. In some embodiments the subject expresses an EYA1 protein that includes the sequence of SEQ ID NO: 3. In some embodiments the subject expresses an EYA1 protein that includes the sequence of SEQ ID NO: 11. In some embodiments the subject expresses an EYA1 protein that includes the sequence of SEQ ID NO: 12. In some embodiments the subject expresses a naturally occurring EYA1 protein that includes the sequence of SEQ ID NO: 2. In some embodiments the subject expresses a naturally occurring EYA1 protein that includes the sequence of SEQ ID NO: 3. In some embodiments the subject expresses the human EYA1 protein. In some embodiments the subject is a human. In some embodiments the subject is a mouse or a rat, cf. above. As indicated above, the mouse or the rat may express the human EYA1 protein that includes the sequence of SEQ ID NO: 2. The mouse or the rat may express the human EYA1 protein that includes the sequence of SEQ ID NO: 3. The mouse or the rat may in some embodiments express the human EYA1 protein that includes the sequence of SEQ ID NO: 11. The mouse or the rat may express the human EYA1 protein that includes the sequence of SEQ ID NO: 12.

In some embodiments the disease involving aberrant fibroblast proliferation is a desmoplasia, such as a cancer. In some embodiments of the method of the ninth aspect the disease involving aberrant fibroblast proliferation is fibrosis. In some embodiments the fibrosis is CKD.

According to a tenth aspect, there is provided an in vitro method of identifying a candidate compound for treating a disease involving aberrant fibroblast proliferation in a subject. The method includes contacting the protein EYA1 with a test compound. The method furthermore includes determining the phosphoserine phosphatase activity, the phosphothreonine phosphatase activity and/or the phosphotyrosine phosphatase activity of EYA1 relative to a control. An increased phosphoserine phosphatase activity, an increased phosphothreonine phosphatase activity and/or a reduced phosphotyrosine phosphatase activity of EYA1 relative to the control indicates that the test compound is a candidate compound for treating disease involving aberrant fibroblast proliferation in a subject.

The control in some embodiments is the absence of a candidate compound. In some embodiments the control is a compound known not to affect the phosphoserine phosphatase activity, the phosphothreonine phosphatase activity and/or the phosphotyrosine phosphatase activity of EYA1.

In some embodiments the protein EYA1 includes the sequence of SEQ ID NO: 2. In some embodiments the protein EYA1 includes the sequence of SEQ ID NO: 3. In some embodiments the protein EYA1 includes the sequence of SEQ ID NO: 11. In some embodiments the protein EYA1 includes the sequence of SEQ ID NO: 12. In some embodiments the protein EYA1 is a naturally occurring protein that includes the sequence of SEQ ID NO: 2. In some embodiments the protein EYA1 is a naturally occurring protein that includes the sequence of SEQ ID NO: 3. In some embodiments the subject expresses the human EYA1 protein. In some embodiments the subject is a human. In some embodiments the subject is a mouse or a rat, see also above. The mouse or the rat may express the human EYA1 protein that includes the sequence of SEQ ID NO: 2. The mouse or the rat may express the human EYA1 protein that includes the sequence of SEQ ID NO: 3. In some embodiments the mouse or the rat may express the human EYA1 protein that includes the sequence of SEQ ID NO: 11. The mouse or the rat may in some embodiments express the human EYA1 protein that includes the sequence of SEQ ID NO: 12.

In some embodiments the disease involving aberrant fibroblast proliferation is a desmoplasia, such as a cancer. The desmoplasia is in some embodiments a prostate cancer or a breast cancer. In some embodiments the desmoplasia is a desmoplastic malignant melanoma or a desmoplastic squamous cell carcinoma. In some embodiments the desmoplasia is a morpheaform basal cell carcinoma or a microcystic adnexal carcinoma. In some embodiments the desmoplasia is a cutaneous leiomyosarcoma or a cutaneous metastasis. In some embodiments the disease involving aberrant fibroblast proliferation is pancreatic cancer or colon cancer. In some embodiments the disease involving aberrant fibroblast proliferation is lung cancer or a neuroblastoma.

In some embodiments of the method of the tenth aspect the disease involving aberrant fibroblast proliferation is fibrosis. In some embodiments the fibrosis is CKD.

BRIEF DESCRIPTION OF THE DRAWINGS

FIG. 1 is a schematic illustration on effects thought to be underlying a method disclosed herein. Alternative splicing of EYA1 leads to the formation of isoform EAY1A or EAY1C. The formation of isoform EAY1A is to be avoided, or the consequences thereof to be alleviated or reduced. Administering antisense-oligonucleotides (ASO) and/or demethylation of a site at intron 9-10 of an EAY1 precursor nucleic acid molecule can lead to the formation of isoform EAY1C instead of isoform EAY1A. Identifying the presence of SNP rs1325938 can be used for the prediction of the risk of occurrence of fibrosis and cancer. Inhibiting unfavourable tyrosine phosphatase activity of EYA1A, for instance by administering orthovanadate, reduces the occurrence of fibrosis. NHEJ, caused by EYA1A abundance, can be inhibited by using the ligase IV inhibitor SCR7 or by administering morpholinos targeting 53Bp1.

FIGS. 2A-2V illustrate that fibrotic fibroblasts resist genotoxic stress by accelerated recruitment of high-fidelity NHEJ DNA damage response. FIG. 2A shows representative photomicrographs of kidney, heart, lung and liver sections labelled for Sirius Red/Fast green (scale bars: 50 µm) and γH2A.X/alpha-smooth muscle actin (αSMA) (red/magenta, scale bars: 25 µm), as well as DAPI nucleic acid stain (blue). FIG. 2B shows the same photomicrographs as FIG. 2A with signals in blue colour and magenta colour reduced to 0, thereby effectively leaving signals not resulting from stain, green and red colour. FIG. 2C shows the same photomicrographs as FIG. 2A with signals in green colour and blue colour reduced to 0, thereby effectively leaving signals not resulting from stain, green and magenta colour. FIG. 2D shows the same photomicrographs as FIG. 2A with signals in blue colour and magenta colour reduced to 0, thereby effectively leaving signals not resulting from stain, green and red colour. The graph in FIG. 2E summarizes relative αSMA+ cells positive for γH2A.X (n=3 in each group). FIG. 2F shows representative photomicrographs of kidney sections labelled for γH2A.X/Cyclin D1/Collagen-4 (red/magenta, scale bars: 25 µm), γH2A.X/p-Chk1$^{pS317}$/Collagen-4 (red/magenta/green, scale bars: 25 µm) and γH2A.X/p-Chk2$^{pT68}$/Collagen-4 (red/magenta/green, scale bars: 25 µm), as well as DAPI nucleic acid stain (blue). FIG. 2G shows the same photomicrographs as FIG. 2F with all colour signals other than green colour (left), magenta colour (center), and blue colour (right) reduced to 0. The graphs in FIGS. 2H to 2K summarize average and relative γH2A.X+ interstitial cells positive for p-Chk1$^{pS317}$ or p-Chk2$^{pT68}$ (T=tubules, n=3 in each group). FIG. 2M, n=3 in each group, data are presented as means±s.d., p<0.01, values of p were calculated using Student's t test comparing indicated groups). FIGS. 2Q to 2T are graphs summarizing average foci per nucleus of primary human fibroblast cultures, of which FIGS. 2O and 2P show representative images (n=100 nuclei each, data are presented as means±s.d.). FIGS. 2U and 2V depict an analysis of NHEJ and HR events upon DNA damage using pEGFP-Pem1-Ad2 (NHEJ) and pDR-GFP (HR) reporter plasmids (n=3 independent replicates, data are presented as means±s.d., *p<0.05, **p<0.01, values of p were calculated using Student's t test comparing indicated groups). Significantly increased NHEJ pEGFP-Pem1-Ad2 and reduced HR pDR-GFP reporter activities can be seen in fibrotic fibroblasts.

FIGS. 7A-7H illustrate that EYA1 isoforms determine DDR cell fate decisions and CKD progression. FIGS. 7A and 7B depict results of qRT-PCR analysis. The graphs reflect relative mRNA expression levels of total EYA1 and EYA1 isoforms EYA1A and EYA1C (n=3 in each group, data are presented as means±s.d., *p<0.001, # no significance, values of p were calculated using Student's t test comparing fibrosis with no fibrosis). FIG. 7C depicts results of gelectrophoretic analysis, where (EYA1A and EYA1C were exposed to SDS-PAGE and subsequent immunoblotting in normal (S1287, S1391 and S1793) and fibrotic kidneys (S2259, S1417 and 51557). FIG. 7D shows an analysis by qRT-PCR of EYA1 isoform expression in primary fibroblast cultures isolated from non-fibrotic and fibrotic kidneys (n=3 in each group, data are presented as means±s.d., p<0.01, *p<0.001, values of p were calculated using Student's t test comparing fibrotic with non-fibrotic fibroblasts). FIG. 7E depicts kidney disease progression in patients with predominant EYA1A (EYA1A>EYA1C) or EYA1C (EYA1A<EYA1C) abundance within renal fibroblasts (n=47, values of p were calculated using log-rank/Mantel-Cox test comparing EYA1A>EYA1C and EYA1A<EYA1C). FIG. 7F depicts a gelectrophoretic analysis of overexpression by SDS-PAGE and immunoblotting, after wildtype mice and mice harbouring DOX-inducible transgenes for EYA1A (rtTAhCMV, hEYA1A-pTreTight, referred as EYA1A$^{tg}$) or EYA1C (rt-TAhCMV;hEYA1C-pTreTight, referred as EYA1C$^{tg}$) were challenged with unilateral ureteral obstruction (UUO), EYA1A and EYA1C. FIG. 7G depicts the proliferative activity of primary murine fibroblasts from wildtype, EYA1A$^{tg}$ or EYA1C$^{tg}$ mice, seeded at a density of 60,000 per well, at indicated time points (n=3 independent replicates, data are presented as means±s.d., p<0.0001, values of p were calculated using Student's t test comparing DOX-treated EYA1Atg or EYA1C$^{tg}$ cultures with corresponding uninduced fibroblasts). FIG. 7H depicts the relative fibrotic interstitial area at indicated time points after ureteral obstruction of fibroblasts from wildtype, EYA1A$^{tg}$ or EYA1C$^{tg}$ mice (p<0.01, ***p<0.001, values of p were calculated using Student's t test comparing DOX-treated wildtype, EYA1A$^{tg}$ or EYA1 C$^{tg}$ mice with corresponding uninduced littermates).

FIGS. 10A-10Z1 illustrate that high-fidelity NHEJ causally contributes to fibrosis and fibroblast accumulation. FIG. 10A depicts average foci per nucleus (n=100 nuclei, data are presented as means±s.d.) of primary murine EYA1A^tg or EYA1C^tg fibroblast cultures labelled for γH2A.X$^{pS139}$ at indicated time points after NCS exposure. FIGS. 10T and 10U summarize the relative fibrotic interstitial area of the kidney sections of which images are depicted in FIGS. 10L to 10O, and FIG. 10P to 10S, respectively (n=6 in each group, data are presented as means±s.d., *p<0.05, p<0.01, **p<0.0001, values of p were calculated using Student's t test comparing indicated groups). FIGS. 10V and 10W show data of mice harbouring DOX-inducible transgenes for EYA1A (EYA1A^tg), challenged with UUO and treated with DNA ligase IV inhibitor SCR7 (20 mg/kg i.p. every alternate day), representative photomicrographs of kidney sections labelled for alpha-smooth muscle actin (αSMA) (FIG. 10W, scale bars: 25 µm) or Collagen-1 (FIG. 10X, scale bars: 25 µm) 10 days after ureteral obstruction. The graphs summarize average interstitial cells positive for αSMA and relative means of area positive for Collagen-1 (n=6 in each group, data are presented as means±s.d., *p<0.05, **p<0.0001, # no significance, values of p were calculated using Student's t test comparing indicated groups). FIGS. 10X, 10Y, 10Z and 10Z1 show data of kidney sections of transgenic EYA1A^tg mice challenged with UUO and treated with in vivo morpholinos blocking 53Bp1 translation (53Bp1-VMO), labelled for 53Bp1 (FIG. 10X), Rpa1 (FIG. 10Y), alpha-smooth muscle actin (αSMA, FIG. 10Z) and Collagen-1 (FIG. 10Z1) 10 days after ureteral obstruction. The figures summarize average interstitial cells of the kidney sections positive for the respective protein (n=6 in each group, data are presented as means±s.d., *p<0.001, ****p<0.0001, values of p were calculated using Student's t test comparing indicated groups).

FIG. 1E depicts qRT-PCR for Bmp7 (n=3 independent replicates, data are presented as means±s.d., *p<0.05, p<0.01, **p<0.0001, values of p were calculated using one-way ANOVA with Bonferroni post-hoc analysis comparing indicated groups).

FIGS. 12A-12B show the effect of the established EYA1 $\gamma H2A.X^{pY142}$ tyrosine phosphatase inhibitors $Na_3VO_4$ (blocking tyrosine phosphatase activity) and caffeine (blocking ATM-dependent recruitment of EYA1 towards γH2A.X) on $\gamma H2A.X^{pY142}$ dephosphorylation and fibroblast accumulation. FIG. 12A depicts results of an analysis of photomicrographs of primary murine fibroblast cultures transfected with control plasmids (vector) and plasmids overexpressing EYA1A (EYA1A$^{oe}$) or EYA1C (EYA1C$^{oe}$). Cells were exposed to either $Na_3VO_4$ or caffeine and labelled for $7H2A.X^{pY142}$ 60 minutes after NCS exposure (n=100 nuclei each, data are presented as means±s.d., p<0.01, # no significance, values of p were calculated using Student's t test comparing indicated groups). FIG. 12B depicts results of an analysis of proliferative activity of primary murine fibroblasts transfected with indicated constructs, seeded at a density of 60,000 per well. Proliferative activity was determined at indicated time points after exposure to $Na_3VO_4$ or caffeine (n=3 independent replicates, data are presented as means±s.d., *p<0.001, ****p<0.0001, values of p were calculated using one-way ANOVA with Bonferroni post-hoc analysis comparing control and $Na_3VO_4^-$ or caffeine-treated cultures overexpressing EYA1A).

FIG. 13A shows relative αSMA+ cells positive for $\gamma H2A.X^{pY142}$, and FIG. 13B shows the fibrotic interstitial area 10 days after ureteral obstruction. FIG. 13C shows αSMA positive cells, and FIG. 13D collagen-1 positive cells (n=6 in each group, data are presented as means±s.d., ****p<0.0001, # no significance, values of p were calculated using one-way ANOVA with Bonferroni post-hoc analysis comparing indicated groups). FIG. 13E shows respective representative photomicrographs of kidney sections labelled for αSMA, as well as DAPI nucleic acid stain (scale bars: 25 μm). FIG. 13F shows representative photomicrographs of kidney sections labelled for collagen-1, as well as DAPI nucleic acid stain (scale bars: 25 μm). FIG. 13G shows the same photomicrographs as FIG. 13C with all colour signals other than red colour (αSMA) reduced to 0. FIG. 13H shows the same photomicrographs as FIG. 13D with all colour signals other than green colour (collagen-1) reduced to 0. FIG. 13I shows representative photomicrographs of kidney sections labelled for MTS (scale bars: 50 μm), also 10 days after ureteral obstruction.

FIG. 14 illustrates results of a screen for additional compounds for selective modulation of EYA1A phosphatase activity. The EYA1A phosphatase activity was estimated using p-nitrophenyl phosphate (pNPP) substrate. Briefly, phosphatase activity was determined in transgenic fibroblasts and pNP production was determined in comparison to control cultures. Among 736 compounds contained in the NCI mechanistic set (NCI Mechanistic Set II), 228 inhibitors of EYA1A phosphatase activity were identified.

FIG. 15A illustrates different EYA1 splicing, differing in the presence or absence of exon 10. FIG. 15B illustrates that an intronic single nucleotide polymorphism (SNP rs13259388 C>T: ccggtgtgC/Tattttatg, the reverse being gtattttaT/Cgtgtggcc) is located −893 bp upstream exon 10 and disrupts an intronic splicing cis regulatory motif. The sequence of the SNP can be found at positions 307554 to 307538 of GenBank accession number NG_011735.3, version 3 as of 24 Feb. 2018. The position of the T/C exchange can be found at position chr8:71245585 in the Ensembl database. FIG. 15C is a schematic illustration of minigene 3 harbouring exons 1-11 and intronic fragments flanking exon 10 containing cis regulatory elements (−1165 bp relative to intron 9-10/exon 10 junction), minigene 4 missing cis regulatory elements (lacking −1165 bp to −920 bp) and minigene 5 (lacking −1165 bp to −634 bp). FIG. 15D depicts Bioanalyzer fluorescent units for an analysis of PCR products using minigene 3-specific oligonucleotides. FIG. 15E depicts Bioanalyzer fluorescent units for an analysis of PCR products using minigene 3-specific oligonucleotides.

allele (TZ1).

FIGS. 17A-17K show that intronic SNP rs13259388 affects EYA1 exon 10 splicing and disease progression in humans. FIGS. 17A to 17I depict the analysis of wildtype "C" allele (SNP$^{-/-}$) and homozygous SNP rs13259388 "T" allele (SNP+i+) carriers kidney sections labelled for EYA1A/αSMA (FIG. 17A), EYA1C/SMA (FIG. 17B), γH2A.X$^{pY142}$ (FIG. 17D), γH2A.X$^{pS139}$ (FIG. 17E), 53BP1/αSMA (FIG. 17F), XRCC4/αSMA (FIG. 17G), RPA1/αSMA (FIG. 17H) and RAD51 (FIG. 17I) (n=3 in each group, measurements were done in 10 visual fields, data are presented as means±s.d., **p<0.0001, values of p were calculated using Student's t test comparing indicated groups). FIG. 17C graphically shows the results depicted in FIGS. 17A and 17B with regard to the identified levels of EYA1 isoforms. FIG. 17J depicts a graph summarizing average proliferation of corresponding fibroblast cultures (n=3 independent replicates, data are presented as means±s.d., p<0.0001, values of p were calculated using Student's t test comparing SNP$^{-/-}$ and SNP$^{+/+}$ fibroblast cultures). FIG. 17K** shows the kidney disease progression in negative patients (SNP$^{-/-}$) and homozygous carriers of SNP rs13259388 (SNP$^{+/+}$) towards ESRD (n=39, values of p were calculated using log-rank/Mantel-Cox test comparing SNP-/- and SNP+/+ carriers).

FIG. 18A depicts the effect of TGF-β1 exposure on the proliferative activity of human kidney fibroblasts (TK173), seeded at a density of 60,000 per well and determined at indicated time points (n=3 independent replicates, data are presented as means±s.d., p<0.01, values of p were calculated using Student's t test comparing control and TGF-β1-treated fibroblasts). FIG. 18B depicts a virtual Bioanalyzer gel image of PCR products using minigene-specific oligonucleotides.

FIGS. 20A to D depict average foci per nucleus detected in human TK173 and TZ1 cultures transfected with EYA1Δe10-ASO and labelled for γH2A.X$^{pS139}$ (FIG. 20A), γH2A.X$^{pS139}$/γH2A.X$^{py142}$ (FIG. 20B), γH2A.X$^{pS139}$/53Bp1 (FIG. 20C), and γH2A.X$^{pS139}$/Rpa1 (FIG. 20D) at indicated time points after NCS exposure (n=100 nuclei each, data are presented as means±s.d.). FIGS. 20E and F depict data on the analysis of NHEJ and HR events upon DNA damage using pEGFP-Pem1-Ad2 upon DNA damage using pEGFP-Pem1-Ad2 (NHEJ, FIG. 20E) and pDR-GFP (HR, FIG. 20F) reporter plasmids (n=3 independent replicates, data are presented as means±s.d., p<0.01, *p<0.001, values of p were calculated using Student's t test comparing indicated groups). FIG. 20G depicts proliferative activity of human kidney fibroblasts at indicated time points after seeding at a density of 60,000 per well (n=3 independent replicates, data are presented as means s.d., and *p<0.05, values of p were calculated using Student's t test comparing EYA1Δe10-ASO-transfected TZ1 with untreated TZ1 cultures). FIG. 20H depicts an analysis of p-Chk1$^{pS317}$ and p-Chk2$^{PT68}$ by SDS-PAGE and subsequent immunoblotting 24 hours after NCS exposure.

FIG. 21 depicts relative mRNA expression levels of isoforms EYA1A and EYA1C in human TK173, TZ1 and TZ1 after transfection of EYA1Δe10-ASO, analyzed by qRT-PCR (n=3 independent replicates, data are presented as means±s.d., **p<0.01, values of p were calculated using Student's t test comparing EYA1Δe10-ASO-transfected TZ1 with untreated TZ1 cultures).

FIG. 22 schematically illustrates intronic EYA1 methylation upstream exon 10, where a CpG island is present, which affects EYA1 exon 10 splicing.

FIG. 23A depicts a virtual Bioanalyzer gel image of methylated DNA immunoprecipitation (MeDIP), showing that the CpG island is commonly methylated in fibrotic kidneys. Briefly, genomic DNA was extracted from kidney biopsies and methylated gDNA was immunoprecipitated by using 5'-methylcytosine-specific antibodies. The PCR reaction was specific for the CpG island upstream EYA1 exon 10 and gel analysis is shown in comparison to total input DNA. FIG. 23B schematically illustrates the use of methylated minigene constructs to test whether methylation of the CpG island had an effect on exon 10 splicing. FIG. 23C depicts a virtual Bioanalyzer gel image of PCR products using minigene-specific oligonucleotides, and FIG. 23D is a graphic representation, both reflecting relative mRNA levels of EYA1A and EYA1C in response to TGF-β1 and in the absence and presence of CpG Methyltransferase (M.SssI). Methylation of the identified regions was associated with increased EYA1 exon 10 inclusion and generation of pro-fibrotic EYA1A.

FIG. 24 shows the sequence of EYA1 isoform A (SEQ ID NO: 1), as found in the SwissProt/Uniprot database under the accession number Q99502, version 2 of the sequence of 15 Jul. 1998, where it has the identifier Q99502-2 (termed isoform B in SwissProt/Uniprot).

FIG. 25 shows the sequence of EYA1 isoform C, as found in the SwissProt/Uniprot database under the accession number Q99502, having the identifier Q99502-2 and termed isoform D in SwissProt/Uniprot.

FIG. 26 depicts the sequence defined by SEQ ID NO: 2.
FIG. 27 depicts the sequence defined by SEQ ID NO: 3.
FIG. 28 depicts the sequence defined by SEQ ID NO: 11.
FIG. 29 depicts the sequence defined by SEQ ID NO: 12. In SEQ ID NO: 12, $X_1$ may be G or S or $X_2$ may be D or G, $X_3$ may be R or Q, $X_4$ may be S or P, and $X_5$ may be L or R.

FIG. 30 depicts the sequence defined by SEQ ID NO: 20, corresponding to exon 10.

FIG. 31 depicts the sequence defined by SEQ ID NO: 11.
FIG. 32 depicts the sequence defined by SEQ ID NO: 6.
FIG. 33A depicts results of a phylogenetic analysis. As can be taken from the figure, there is a conserved genomic region within EYA1 corresponding to the identified intronic splicing cis regulatory motif among primate species including chimpanzee, gorilla, orangutan and vervet monkeys.
FIG. 33B depicts the results of an analysis of the intronic region upstream EYA1 exon 10 with regard to predicted RNA bridge formation.
FIG. 33C illustrates the location of rs13259388 in the surrounding human sequence.

FIG. 35 depicts the source of oligonucleotides used in the Working Examples for qRT-PCR. "Undisclosed": these oligonucleotides are available from the indicated source (PrimerDesign, Chandler's Ford, UK; Applied Biosystems, part of Thermo Fisher Scientific, Dublin, Ireland), the supplier does, however, not disclose the corresponding sequences. SEQ ID NO: 23: 5'-CTCTTCCA GCCATCTTTCATTG-3'; SEQ ID NO: 24: 5'-GTTGTTAGCAT-AGAGATCCTTTCCT-3'; SEQ ID NO: 25: 5'-ATGGAT-TCCCGTTCGAGTA CG-3'; SEQ ID NO: 26: 5'-TCAGCTGGATAGCGACAT CG-3'.

FIGS. 36A-36E depict examples of nucleic acid ligase IV inhibitors: SCR7 (FIG. 36A), SCR7 pyrazine (FIG. 36B), L67 (FIG. 36C), L82 (also called SCR5, FIG. 36D), and L189 (also called SCR6, FIG. 36E).

FIG. 37 depicts in vivo morpholino sequences used in the Working Examples. All three oligonucleotides were obtained from Gene Tools (Philomath, USA).

FIG. 38 depicts morpholino sequences used in the Working Examples. The oligonucleotides of SEQ ID NOs: 33 and 29 were obtained from Gene Tools (Philomath, USA).

FIG. 39 depicts the sequence of the exon of human Eya1 that is termed exon 10 herein. A variant exists where at the underlined position instead of G the sequence contains A. This variant falls within the term "exon 10" as used herein.

DETAILED DESCRIPTION

Definitions

Figure 2H:
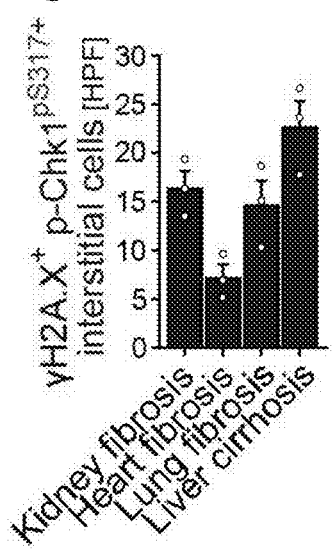
Figure 2I:
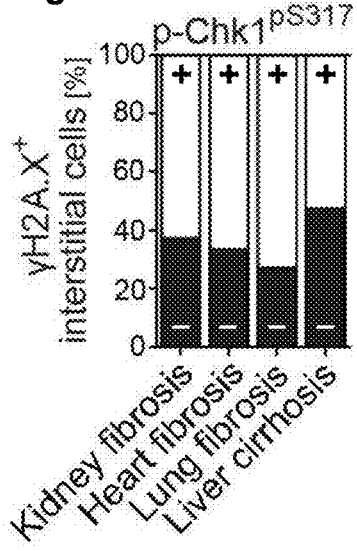
Figure 2J:
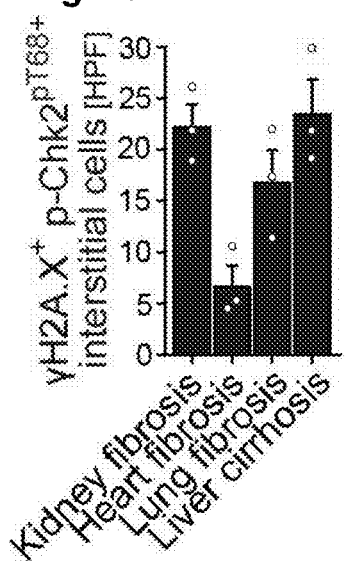
Figure 2K:
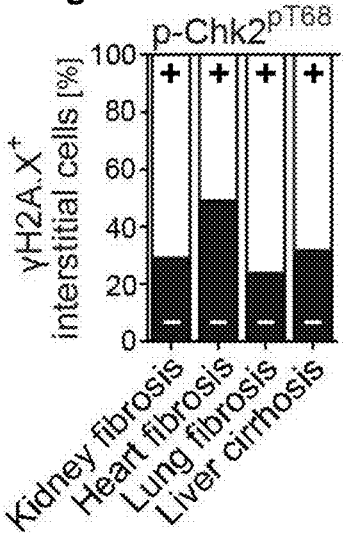

Unless otherwise defined, all other scientific and technical terms used in the description, figures and claims have their ordinary meaning as commonly understood by one of ordinary skill in the art. Although similar or equivalent methods and materials to those described herein can be used in the practice or testing of the binding members, nucleic acids, vectors, host cells, compositions, methods and uses disclosed herein, suitable methods and materials are described below. All publications, patent applications, patents, and other references mentioned herein are incorporated by reference in their entirety. In case of conflict, the present specification, including definitions, will prevail. If two or more documents incorporated by reference include conflicting and/or inconsistent disclosure with respect to each other, then the document having the later effective date shall control. The materials, methods, and examples are illustrative only and not intended to be limiting.

Unless otherwise defined, all other scientific and technical terms used in the description, figures and claims have their ordinary meaning as commonly understood by one of ordinary skill in the art. Although similar or equivalent methods and materials to those described herein can be used in the practice or testing of the binding members, nucleic acids, vectors, host cells, compositions, methods and uses disclosed herein, suitable methods and materials are described below. All publications, patent applications, patents, and other references mentioned herein are incorporated by reference in their entirety. In case of conflict, the present specification, including definitions, will prevail. If two or more documents incorporated by reference include conflicting and/or inconsistent disclosure with respect to each other, then the document having the later effective date shall control. The materials, methods, and examples are illustrative only and not intended to be limiting.

Unless otherwise stated, the following terms used in this document, including the description and claims, have the definitions given below.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects as described herein. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The term "administering", as used herein, refers to any mode of transferring, delivering, introducing, or transporting matter such as a compound, e.g. a pharmaceutical compound, or other agent such as an antigen, to a subject. Modes of administration include oral administration, topical contact, intravenous, intraperitoneal, intramuscular, intranasal, or subcutaneous administration (cf. below). Administration "in combination with" further matter such as one or more therapeutic agents includes simultaneous (concurrent) and consecutive administration in any order.

An "agent", as used herein, refers to any compound or combination of compounds. Typically an agent is a single compound. A respective compound may be a low-molecular weight organic compound or a polymeric compound. An example of a polymeric compound is a protein such as EYA1 or a nucleic acid molecule such as a vector.

The term "antisense activity" means any detectable or measurable activity attributable to the hybridization of an antisense compound to a target nucleic acid molecule. In some embodiments, antisense activity is a decrease in the amount or expression of a target nucleic acid or protein encoded by such target nucleic acid.

In this regard, antisense technology is an effective means for modulating the expression of a specific gene product and is useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. In one aspect, an antisense compound provided herein modulates splicing of a target gene. Such modulation includes promoting or inhibiting exon inclusion.

The terms "antisense oligonucleotide," "antisense oligomer," and "antisense compound" are used interchangeably and refer to a compound having a sequence of nucleotide bases and a subunit-to-subunit backbone that allow the antisense oligomer to hybridize to a target nucleic acid molecule through hydrogen bonding. An antisense compound is typically a single-stranded nucleic acid molecule of a length of 6 to 30, such as 15 to 30 nucleobases. An antisense compound may in some embodiments be an siRNA. In some embodiments, an antisense compound has a nucleobase sequence that, when written in the 5' to 3' direction, includes the reverse complement of the target segment of a target nucleic acid molecule to which it is targeted.

The term "detect" or "detecting", as well as the term "determine" or "determining" when used in the context of a signal such as a current, refers to any method that can be used to detect the flow of ions. Detection can be done both on a qualitative and a quantitative level. When used herein in combination with the words "level", "amount" or "value", the words "detect", "detecting", "determine" or "determining" are understood to generally refer to a quantitative rather than a qualitative level. Accordingly, a method as described herein may include a quantification of a current.

A "protein coding sequence" or a sequence that encodes a particular protein or polypeptide, is a nucleic acid sequence that gives rise to the formation of that particular protein or polypeptide. In the case of DNA it is transcribed into mRNA and is translated (in the case of mRNA) into a polypeptide in vitro or in vivo when placed under the control of a suitable regulatory sequence. The boundaries of the coding sequence are determined by a start codon at the 5' terminus (N-terminus) and a translation stop nonsense codon at the 3' terminus (C-terminus). A coding sequence may include cDNA from prokaryotic or eukaryotic mRNA, genomic DNA sequences from prokaryotic or eukaryotic DNA, or any synthetic nucleic acid. A transcription termination sequence will usually be located 3' to the coding sequence.

The term "essentially consists of" is understood to allow the presence of additional components in a sample or a composition that do not affect the properties of the sample or a composition. As an illustrative example, a pharmaceutical composition may include excipients if it essentially consists of an active ingredient.

The terms "expressing" and "expression" in reference to a polypeptide are intended to be understood in the ordinary meaning as used in the art. A polypeptide is expressed by a cell via transcription of a nucleic acid into mRNA, followed by translation into an initial polypeptide, which is folded and possibly further processed to a mature polypeptide. Hence, the statement that a cell or an organism is expressing such a polypeptide indicates that the polypeptide is found in or on the cell, and cells of the organism, respectively, and implies that the polypeptide has been synthesized by the expression machinery of the respective cell. EYA1 is usually located inside a cell, in the cytoplasm or in the nucleus.

With regard to the respective biological process itself, the terms "expression", "gene expression" or "expressing" refer to the entirety of regulatory pathways converting the information encoded in the nucleic acid sequence of a gene first into messenger RNA (mRNA) and then to a polypeptide. Accordingly, the expression of a gene includes its transcription into a primary hnRNA, the processing of this hnRNA into a mature RNA and the translation of the mRNA sequence into the corresponding amino acid sequence of the polypeptide. In this context, it is also noted that the term "gene product" refers not only to a polypeptide, including e.g. a mature polypeptide (including a splice variant thereof) encoded by that gene and a respective precursor protein where applicable, but also to the respective mRNA, which may be regarded as the "first gene product" during the course of gene expression.

By "fragment" in reference to a polypeptide such as receptor molecule is meant any amino acid sequence present in a corresponding polypeptide, as long as it is shorter than the full length sequence and as long as it is capable of performing the function of interest of the protein—in the case of EYA1 generally its tyrosinephosphate phosphatase activity, its transcriptional coactivator activity, and/or its serinephosphate and threoninephosphate phosphatase activity.

As used herein, a "heterologous" nucleic acid molecule or a "heterologous" nucleic acid sequence is a nucleic acid molecule and sequence, respectively, that does not occur naturally as part of the genome of the cell in which it is present, or a nucleic acid sequence which is found in a location or locations in the genome that differ from that in which it occurs in nature. Typically, a heterologous nucleic acid molecule and/or sequence carries or is a sequence that is not endogenous to the host cell and has been artificially introduced into the cell. The cell that expresses a heterologous nucleic acid sequence may contain DNA encoding the same or different expression products. A heterologous nucleic acid sequence need not be expressed and may be integrated into the host cell genome or maintained episomally.

As used herein, "hybridization" means the pairing of a complementary strand of an antisense compound to its target sequence. While not limited to a particular mechanism, the most common mechanism of pairing involves hydrogen bonding, which may be Watson-Crick, Hoogsteen or reversed Hoogsteen hydrogen bonding, between complementary nucleobases. For example, the natural base adenine is complementary to the natural nucleobases thymidine and uracil which pair through the formation of hydrogen bonds.

The natural base guanine is complementary to the natural bases cytosine and 5-methyl cytosine. Hybridization can occur under varying circumstances.

An antisense compound as disclosed herein is specifically hybridizable to the target sequence indicated. A compound such as an antisense compound as disclosed herein is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays. In this regard, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

"Identical" as used herein is the extent of sequence identity (homology), which may be determined using any computer program and associated parameters known in the art, such as BLAST 2.2.2 or FASTA version 3.0t78, for instance with the default parameters. Protein and/or nucleic acid sequence identities (homologies) may be evaluated using any of the variety of sequence comparison algorithms and programs known in the art. The term "essentially identical" or "substantially identical" refers to a sequence that has at least 85% sequence identity with the sequence referred to. For example, the sequence of a nucleic acid molecule is substantially identical to a given nucleic acid sequence if it has 90% or more sequence identity with the same. As a further example, the sequence of a peptide or protein is substantially identical to a given amino acid sequence if it has 90% or more sequence identity with the same. A sequence essentially identical or substantially identical with another sequence may also be a sequence that has at least 92% sequence identity or 94% sequence identity with the sequence referred to. In some embodiments a sequence essentially identical or substantially identical with another sequence is a sequence that has at least 95% sequence identity or 96% sequence identity with the sequence referred to. In some embodiments a sequence essentially identical or substantially identical with another sequence is a sequence that has 97% sequence identity or more, or 98% sequence identity or more with the sequence referred to. In some embodiments a sequence essentially identical or substantially identical with another sequence is a sequence that has 99% sequence identity or more, or 99.5% sequence identity or more with the sequence referred to.

The term "isolated" indicates that the cell or cells, or the peptide(s) or nucleic acid molecule(s) has/have been removed from its/their normal physiological environment, e.g. a natural source, or that a peptide or nucleic acid is synthesized. Use of the term "isolated" indicates that a naturally occurring sequence has been removed from its normal cellular (i.e., chromosomal) environment. Thus, the sequence may be in a cell-free solution or placed in a different cellular environment. An isolated cell or isolated cells may for instance be included in a different medium such as an aqueous solution than provided originally, or placed in a different physiological environment. Typically isolated cells, peptides or nucleic acid molecule(s) constitute a higher fraction of the total cells, peptides or nucleic acid molecule(s) present in their environment, e.g. solution/suspension as applicable, than in the environment from which they were taken. An isolated polypeptide or nucleic acid molecule is an oligomer or a polymer of amino acids (2 or more amino acids) or nucleotides coupled to each other, including a polypeptide or nucleic acid molecule that is isolated from a natural source or that is synthesized. The term "isolated" does not imply that the sequence is the only amino acid chain or nucleotide chain present, but that it is essentially free, e.g. about 90-95% pure or more, of e.g. non-amino acid material and/or non-nucleic acid material, respectively, naturally associated with it.

As used herein, "modulation of splicing" refers to altering the processing of a pre-mRNA transcript such that the spliced mRNA molecule contains either a different combination of exons as a result of exon skipping or exon inclusion, a deletion in one or more exons, or additional sequence not normally found in the spliced mRNA (e.g., intron sequence). In the context of the present disclosure, modulation of splicing refers to altering splicing of EYA1 pre-mRNA to achieve exon skipping or exon inclusion. In one embodiment, exon skipping results in an EYA1 mRNA transcript lacking exon 10 and exon inclusion results in an EYA1 mRNA transcript containing exon 10. In one embodiment modulation of splicing includes promoting or effecting the removal of exon 10.

The terms "Morpholino oligomer", "Morpholino" and "phosphorodiamidate Morpholino oligomer", the latter abbreviated "PMO", are used interchangeably herein and refer to a single-stranded nucleic acid analog of 15 to 30 bases, typically about 25 bases. In a Morpholino oligomer the bases are covalently linked to a backbone of methylenemorpholine rings linked through phosphorus-containing groups, typically phosphorodiamidate groups. A monomeric unit of a Morpholino oligomer typically has the following structure:

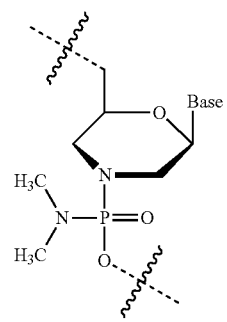

A "nucleobase" means a heterocyclic moiety capable of pairing with a base of another nucleic acid molecule. The term "contiguous nucleobases" refers to nucleobases immediately adjacent to each other.

The term "nucleic acid molecule" as used herein refers to any nucleic acid in any possible configuration, such as single stranded, double stranded or a combination thereof. Examples of nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA), alkylphosphonate and alkylphosphotriester nucleic acid molecules and tecto-RNA molecules (e.g. Liu, B., et al., J. Am. Chem. Soc. (2004) 126, 4076-4077). LNA has a modified RNA backbone with a methylene bridge between C4' and O2', providing the respective molecule with a higher duplex stability and nuclease resistance. Alkylphosphonate and alkylphosphotriester nucleic acid molecules can be viewed as a DNA or an RNA molecule, in which phosphate groups of the nucleic acid backbone are neutralized by exchanging the P—OH groups of the phosphate groups in the nucleic acid backbone to an alkyl and to an alkoxy group, respectively. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used for nucleic acids that are used in the methods described herein. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. A variety of modifications at the sugar moiety are known in the art. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C(R)(R') for the ring oxygen at the 4'-position. Modified sugar moieties are well known and can be used to alter, typically increase, the affinity of a molecule such as an antisense compound for its target and/or increase nuclease resistance. Illustrative examples of modified sugars include but are not limited to a bicyclic modified sugar (BNA), including LNA and ENA (4'-$(CH_2)_2$—O-2' bridge); and a substituted sugar, especially a 2'-substituted sugar having a 2'-F, 2'-OCH 2 or a 2'-O$(CH2)_2$—$OCH_3$ substituent group. A sugar can also be replaced with a sugar mimetic group among others. Methods for the preparations of modified sugars are well known to those skilled in the art. Modifications at the base moiety may be a natural or a synthetic modification of A, C, G, and T/U, a different purine or pyrimidine base, such as uracil-5-yl, hypoxanthin-9-yl, and 2-aminoadenin-9-yl, as well as a non-purine or a non-pyrimidine nucleotide base. Other nucleotide analogues serve as universal bases. Examples of universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

As used in this document, the expression "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The terms "polypeptide" and "protein" are used interchangeably and refer to a polymer of amino acid residues and are not limited to a certain minimum length of the product. Where both terms are used concurrently, this two-fold naming accounts for the use of both terms side by side in the art.

The term "predicting the risk" as used in the disclosure refers to assessing the probability that a subject will suffer from PAH in the future. As will be understood by those skilled in the art, such an assessment is usually not intended to be correct for 100% of the subjects to be investigated. The term, however, requires that a prediction can be made for a statistically significant portion of subjects in a proper and correct manner. Whether a portion is statistically significant can be determined by those skilled in the art using various well known statistic evaluation tools, e.g., determination of confidence intervals, p-value determination, Student's t-test, and Mann-Whitney test. Suitable confidence intervals are generally at least 90%, at least 95%, at least 97%, at least 98%, or at least 99%. Suitable p-values are generally 0.1, 0.05, 0.01, 0.005, or 0.0001. In one embodiment of the disclosed methods, the probability envisaged by the present disclosure allows that the prediction of an increased, normal, or decreased risk will be correct for at least 60%, at least 70%, at least 80%, or at least 90% of the subjects of a given cohort or population. Predictions of risk in a disclosed method relates to predicting whether or not there is an increased risk for PAH compared to the average risk for developing PAH in a population of subjects rather than giving a precise probability for the risk.

In this regard the term "prognosis", commonplace and well-understood in medical and clinical practice, refers to a forecast, a prediction, an advance declaration, or foretelling of the probability of occurrence of a disease state or condition in a subject not (yet) having the respective disease state or condition. In the context of the present invention prognosis refers to the forecast or prediction of the probability as to whether a subject will or will not suffer from PAH.

The term "preventing" in the medical/physiological context, i.e. in the context of a physiological state, refers to decreasing the probability that an organism contracts or develops an abnormal condition.

The word "recombinant" is used in this document to describe a nucleic acid molecule that, by virtue of its origin, manipulation, or both is not associated with all or a portion of the nucleic acid molecule with which it is associated in nature. Generally a recombinant nucleic acid molecule includes a sequence which does not naturally occur in the respective wildtype organism or cell. Typically a recombinant nucleic acid molecule is obtained by genetic engineering, usually constructed outside of a cell. Generally a recombinant nucleic acid molecule is substantially identical and/or substantial complementary to at least a portion of the corresponding nucleic acid molecule occurring in nature. A recombinant nucleic acid molecule may be of any origin, such as genomic, cDNA, mammalian, bacterial, viral, semi-synthetic or synthetic origin. The term "recombinant" as used with respect to a protein/polypeptide means a polypeptide produced by expression of a recombinant polynucleotide.

The term "reducing the risk", as used in this document, means to lower the likelihood or probability of a disease state or condition, e.g., fibrosis, from occurring in a subject, especially when the subject is predisposed to such or at risk of contracting a disease state or condition, e.g., fibrosis.

As used herein, a sgRNA (Single guide RNA) is a RNA molecule, typically a synthetic RNA molecule, that includes or is composed of a targeting sequence and scaffold sequence derived from bacterial crRNA and tracrRNA. An sgRNA may also include one or more aptameric accessory RNA domains. An sgRNA molecule encodes gene editing information in the form of complementary sequences. It contains one or more crRNAs and one tracrRNA. The sgRNA, once formed, is used to target an endonuclease 9, once formed, to a specific genomic locus in genome editing.

The term "subject" as used herein, also addressed as an individual, refers to an animal, generally a mammal, that expresses the protein EYA1. A subject may be a rodent or a livestock animal. A subject may also be a companion animal or a zoological animal. In some embodiments the subject may be a mammalian species such as a cattle or a goat. The subject may also be a sheep. In some embodiments the subject is a horse. The subject may also be a dog or a cat. In some embodiments the subject is a ferret or a chinchilla. In some embodiments the subject is a pig. The subject may also be a monkey or an ape. In some embodiments the subject may be a rabbit or a mouse. The subject may also be a rat or a Guinea pig. The subject may also be a hamster. In one embodiment the subject is a human.

The terms "treatment" and "treating" as used herein, refer to a prophylactic or preventative measure having a therapeutic effect and preventing, slowing down (lessen), or at least partially alleviating or abrogating an abnormal, including pathologic, condition in the organism of a subject. Those in need of treatment include those already with the disorder as well as those prone to having the disorder or those in whom the disorder is to be prevented (prophylaxis). Generally a treatment reduces, stabilizes, or inhibits progression of a symptom that is associated with the presence and/or progression of a disease or pathological condition. The term "therapeutic effect" refers to the inhibition or activation of factors causing or contributing to the abnormal condition. A therapeutic effect relieves to some extent one or more of the symptoms of an abnormal condition or disease. The term "abnormal condition" refers to a function in the cells or tissues of an organism that deviates from their normal functions in that organism. An abnormal condition can inter alia relate to cell proliferation, cell differentiation, or cell survival.

The term "variant" as used herein can refer to a nucleotide sequence in which the sequence differs from the sequence most prevalent in a population, for example by one nucleotide, in the case of the point mutations described herein. For example, some variations or substitutions in the nucleotide sequence encoding a EYA1 protein can alter a codon so that a different amino acid is encoded resulting in a variant polypeptide. The term "variant" can also refer to a polypeptide in which the sequence differs from a given sequence as explained further below. A variant may for example be a polypeptide in which the sequence differs from the sequence most prevalent in a population. A polypeptide sequence can for instance differ at a position that does not change the amino acid sequence of the encoded polypeptide, i.e. a conserved change. Variant polypeptides can be encoded by a mutated EYA1 sequence.

The terms "comprising", "including," containing", "having" etc. shall be read expansively or open-ended and without limitation. Singular forms such as "a", "an" or "the" include plural references unless the context clearly indicates otherwise. Thus, for example, reference to a "vector" includes a single vector as well as a plurality of vectors, either the same—e.g. the same operon—or different. Likewise reference to "cell" includes a single cell as well as a plurality of cells. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The scope and meaning of any use of a term will be apparent from the specific context in which the term is used. Certain further definitions for selected terms used throughout this document are given in the appropriate context of the detailed description, as applicable. Unless otherwise defined, all other scientific and technical terms used in the description, figures and claims have their ordinary meaning as commonly understood by one of ordinary skill in the art.

Tissues Concerned

Aberrant fibroblast proliferation can occur in many tissues. Progression of many cancer types has been found to involve fibroblast proliferation, and the presence of excessive fibroblasts has been suggested as a marker in diagnosis and therapy of premalignant and malignant tumours. Studies on targeting so called "carcinoma-associated fibroblasts" or "cancer-associated fibroblasts", a heterogeneous population of cells defining a major component of tumour stroma, releasing inter alia TGF, are ongoing. Collagen, synthesized by fibroblasts (supra), has been found to be involved in inter alia cancer cell behaviour as well as cancer initiation and progression via interactions with other extracellular matrix proteins (Xu et al., J. Transl. Med. (2019) 17, 309, doi: 10.1186/s2967-019-2058-1). An example of a disease associated with aberrant fibroblast proliferation is a melanoma. Two further examples of a disease associated with aberrant fibroblast proliferation are breast cancer and gastric cancer. Pancreatic adenocarcinoma, in particular pancreatic ductal adenocarcinoma, and ovarian cancer are two further examples of a disease associated with aberrant fibroblast proliferation. Aberrant fibroblast proliferation has also been found to occur in liver cirrhosis and hepatocellular carcinoma. Dermatofibroma, such as atrophic dermatofibroma, as well as a plexiform fibrohistiocytic tumour are further examples of a disease associated with aberrant fibroblast proliferation. As yet a further example, the activation and proliferation of fibroblasts that are resistant to apoptosis has been identified to be involved in remodelling of the myocardium that can progress to heart failure with preserved ejection fraction (Oatmen, K E, Nat Rev Cardiol. (2019), doi: 10.1038/s41569-019-0286-y).

Desmoplasia, a term typically only used to define desmoplastic small round cell tumours, is on a general basis the growth of fibrous and/or connective tissue or stroma. Fibroblasts are the major contributor to desmoplasia. Typically, the stromal reaction in a cancerous tumour is similar to the stromal reaction induced by injury or wound repair, namely increased ECM and growth factor production and secretion, which consequently cause growth of the tissue. In some embodiments, a disease associated with aberrant fibroblast proliferation can therefore be defined as involving desmoplasia.

EYA1 has been found to be overexpressed in various types of cancer, such as Wilms' tumours, breast cancer, gastric carcinoma, hepatocellular carcinoma and a subset of leukemia patients. The phosphatase activity of EYA1 has been found to enhance breast cancer cellular proliferation (Wu, K, et al., Cancer Res. (2013) 73(14), 4488-4499). In stages 1, 2, 3 and 4S of neuroblastoma, overexpression of EYA1 has been observed, and EYA1 has been suggested as a prognostic marker in neuroblastoma (Hansen, J. N., et al., J Cancer Res Ther (Manch) (2016) 4(2), 11-18.).

EYA1 has furthermore been found to contribute to the Epithelial-Mesenchymal Transition (EMT)-like phenotype change occurring in hepatocellular carcinoma (Kong, D., et al., Am. J. Transl. Res. (2019) 11(4), 2328-2338). The authors suggest EYA1 as a prognostic factor for hepatocellular carcinoma patients. Against this background, the methods developed by the present inventors are a promising approach in preventing, treating or delaying progression of a cancerous tumour.

As explained above, aberrant fibroblast proliferation furthermore occurs in fibrosis. Fibrosis can also occur in many tissues within the human or animal body, typically as a result of inflammation or damage. Two illustrative examples are the lungs and the liver. In the lungs, pulmonary fibrosis and radiation-induced lung injury following treatment for cancer can occur. Pulmonary fibrosis may be in the form of cystic fibrosis or idiopathic pulmonary fibrosis. In the liver cirrhosis can occur. Two further illustrative examples are the kidney and the heart. In the kidney fibrosis is a characteristic feature of all forms of chronic renal disease. In chronic kidney disease progressive decline of renal function and continuous accumulation of extracellular matrix occurs, which leads to a diffuse fibrosis in the form of non reversible scarring. The common process is interstitial fibrosis, the deposition of pathological fibrillar matrix in the potential space between tubules and peritubular capillaries. It is generally accepted that the underlying process is a wound-healing response to tissue injury that does not resolve. In the heart, in typical cases an excess deposition of extracellular matrix occurs in the cardiac muscle, a process called cardiac fibrosis. Cardiac fibroblasts are an essential cell type in the heart, responsible for the homeostasis of the extracellular matrix. Upon chronic insult, these cells transform to a myofibroblast phenotype and contribute to cardiac fibrosis. In some cases fibrosis in the heart occurs in the form of an abnormal thickening of the heart valves due to inappropriate proliferation of cardiac fibroblasts.

In embodiments where the disease is renal fibrosis, it is a non reversible connective tissue development leading inevitably to chronic progressive renal disease, the common final pathway in the majority of primary renal disease. Chronic kidney disease (CKD) may have various different initial causes such as diabetes mellitus, hypertension/vascular disease or direct injury, with a subsequent fibrotic response. CKD involves the retention and subsequent accumulation of solutes such as indoxyl sulfate and p-cresyl sulfate that would be cleared by a healthy kidney. Chronic kidney disease generally leads to a progressive decline in kidney function. The effect of the destruction of nephrons is compensated by hypertrophy and a supranormal glomerular filtration rate of remaining nephrons, while the scarring process already progresses. In addition, compensatory hyperfiltraion causes overwork injury in the remaining nephrons, causing further fibrosis. Accordingly, renal fibrosis not only occurs in the end stage of CKD with reduced glomerular filtration rate, but already at early stages with a glomerular filtration rate of 90 mL/min/1.73 $m^2$ or higher.

EYA1

EYA1 (synonym EYA transcriptional coactivator and phosphatase 1) encodes for a member of the evolutionary conserved eyes absent family. The parent eyes absent gene was originally identified in eyeless *drosophila* mutants.

In humans, unlike in any other species, alternative splicing generates EYA1 transcript variants, raising the possibility that humans gained alternative splicing as a means to differentially regulate EYA1 substrate specificities, cf. also below. Alternative splicing of EYA1 has previously been associated with mutations leading to skipping of exon 8, involved in Branchio-Oto-Renal Syndrome, an inherited disease characterized by branchial closure defects leading to cysts or periauricular pits/tags, hearing loss, and renal abnormalities.

The human protein Eyes absent homolog 1, encoded by the gene EYA1, can be found in the SwissProt/Uniprot database under the entry Q99502, version 164 of 12 Sep. 2018, version 2 of the sequence of 15 Jul. 1998. The gene sequence, including the sequence encoded, can be found in the GenBank database under the accession number Y10260.1, version 1 of the sequence as of 8 Feb. 1997, the version of the database entry is of 2 Feb. 2011. The gene sequence on human on chromosome 8 encoding EYA1 that has been curated by NCBI as a reference standard, has GenBank accession number NG_011735.3, version 3 of the sequence dated 24 Feb. 2018, database entry as of 3 Jun. 2019. It is a linear DNA sequence of 357,698 bp, which includes a total 18 exons, which are consecutively numbered in the GenBank entry.

Both the SwissProt/Uniprot database database entry and the GenBank database list three isoforms formed by alternative splicing. The GenBank database names these proteins encoded by the transcript variants isoforms A, B or C, and D. The SwissProt/Uniprot database names these isoforms according to the transcripts isoform EYA1A (SwissProt/Uniprot identifier: Q99502-1), isoform EYA1B (SwissProt/Uniprot identifier: Q99502-2), and isoform EYA1D (SwissProt/Uniprot identifier: Q99502-3). The sequence of GenBank accession number Y10260.1 is termed the EYA1A gene, encoding a protein of 559 amino acids. This protein is termed isoform EYA1B in the SwissProt/Uniprot database.

A further sequence found in the GenBank database under the accession number AJ000097.1 is termed the mRNA for the EYA1B gene. The database entry is the second version (termed "version 1", following a first "sequence 0" of 5 Dec. 1997) of the sequence as of 26 Nov. 1998, the version of the database entry is of 1 Feb. 2011. It encodes a protein of 592 amino acids and differs from variant A in that the first eight amino acids are replaced by a stretch of 41 amino acids. This protein is termed isoform EYA1A in the SwissProt/Uniprot database (SwissProt/Uniprot identifier: Q99502-1), and it has been chosen as the canonical sequence. A GenBank database entry having accession number NM_172058.4, version 4 of the sequence as of 7 May 2019, database entry of 8 Aug. 2019, is termed transcript variant EYA1B. It differs from the sequence of GenBank accession number AJ000097.1 in the exchange of the first base for a sequence of 73 bases as well as a few base exchanges and an additional TTT triplet following base 2845 of the sequence of GenBank accession number AJ000097.1. A similar sequence can be found in the GenBank database as isoform C with accession number NM_000503.6. The database entry is the sixth version of the sequence as of 23 Nov. 2018, the version of the database entry is of 8 Aug. 2019.

The last isoform is found in the GenBank database as transcript D with accession number AF467247.1. The database entry is the first version of the sequence as of 2 Feb. 2002, the version of the database entry is of 11 Mar. 2010. This protein is also termed transcript EYA1D in the SwissProt/Uniprot database (SwissProt/Uniprot identifier: Q99502-3). Isoform EYA1D differs from isoform EYA1C—according to GenBank numbering—in that amino acids 140 to 144 and 351 to 380 of isoform EYA1C are missing. The isoform of transcript EYA1D has a length of 557 amino acids. The GenBank/GenPept accession number of the protein sequence, called EYA1D, is AAL73437, version 1 of 2 Feb. 2002, database entry of 11 Mar. 2010.

In the following the numbering of proteins according to GenBank is essentially followed. Accordingly, the isoform of GenBank accession number Y10260.1, which has SwissProt/Uniprot identifier Q99502-1 as EYA1A according to SwissProt/Uniprot numbering, is called EYA1A. The isoform of GenBank accession number AF467247.1, termed transcript D in GenBank, and having SwissProt/Uniprot identifier Q99502-3 as transcript EYA1D according to SwissProt/Uniprot numbering, is called protein EYA1C.

Eya family members are unique in possessing both phosphoserine/phosphothreonine and phosphotyrosine phophatase activities. Eya family members are primarily known as transcriptional activators through their serine phosphatase activity (Li, X, et al., Nature (2003) 426, 247-254). Three phosphotyrosine phosphatase substrates of EYA1 have been described, namely the atypical protein kinase C zeta, the estrogen receptor beta and the histone H2A variant H2A.X. However, only histone H2A variant H2A.X could be confirmed as a substrate of EYA1. H2A.X is involved in the repair versus apoptosis response to DNA damage, see e.g. Rebay, I, Mol. Cell Biol (2016) 36, 5, 668-677. The protein EYA1 localizes at sites of DNA damage at double-strand breaks. Studies in *drosophila* and mice failed to establish EYA1 as dynamic dual-function phosphatase though (Li et al., 2003, supra; Millhouse, S, Manley, J L, Mol Cell Biol (2005) 25, 533-544).

EYA1 and DNA Damage Repair

Since a single unrepaired DNA double-strand break can lead to genome rearrangements and potentially to cell death, cells have evolved three repair mechanisms to face this threat and maintain genomic integrity: non-homologous end joining (NHEJ), microhomology-mediated end joining (MMEJ), and homologous recombination (HR).

Homologous recombination can be carried out where an identical or essentially identical sequence is present that can be used as a template. The enzymatic machinery involved is nearly identical to the machinery responsible for chromosomal crossover during meiosis. This pathway allows a damaged chromosome to be repaired using a sister chromatid or a homologous chromosome as a template. In NHEJ a particular DNA ligase directly joins the two ends. To guide accurate repair, NHEJ relies on short homologous sequences called microhomologies present on the DNA ends to be joined. If the respective single-stranded overhangs are compatible, repair is usually accurate. However, NHEJ can also introduce mutations and loss of damaged nucleotides at the break site can lead to deletions. MMEJ starts with short-range end resection by a nuclease on either side of a double-strand break to reveal microhomology regions. MMEJ is always accompanied by a deletion, so that MMEJ is a mutagenic pathway for DNA repair.

The global DNA damage response (DDR) system begins with activation of a protein kinase, the protein kinase ATM, which detects the damaged DNA and leads to chromatin relaxation at sites of double-strand breaks. Protein kinase ATM furthermore phosphorylates the chromatin-bound histone variant H2A.X at its serine 139. The phosphorylated H2A.X is γ-H2A.X4, which is required for subsequent interaction with downstream DNA repair proteins as well as chromatin modifying proteins. At the basal level, i.e. without DNA damage induction, H2A.X is furthermore phosphorylated at tyrosine 142 by a transcription factor (Xiao, A, et al., Nature (2009) 457, 57-62). When protein kinase ATM phosphorylates Ser139 of H2A.X upon DNA damage, the phosphotyrosine phosphatase activity of EYA1 removes this phosphate group at tyrosine 142. As a result, H2A.X interacts with the mediator protein MDC1, which promotes signal amplification. MDC1 interacts with γ-H2A.X via the phosphorylated S139 site and facilitates further recruitment of EYA to the DNA lesion.

The present inventors have found that the exclusion/inclusion of EYA1 exon 10 is a critical factor. When exon 10 is excised, then referred to as EYA1C, EYA1 acts predominantly as a serine phosphatase. This is functionally relevant, because EYA1 is shuttled to target genes by co-transcription factors of the Six/Dachs family, where it enhances transcription by dephosphorylation of the RNA polymerase IIb. Targeted genes include BMP7, and ultimately, EYA1C enhances kidney regeneration and is renoprotective.

In contrast, when exon 10 is included, then referred to as EYA1A, the protein acts predominantly as a tyrosine phosphatase on γ-H2A.X, removing tyrosine residue 142. The inventors furthermore found that, as consequence of EYA1A upregulation, accelerated dephosphorylation of tyrosine residue 142 of γ-H2A.X changes the response of fibroblasts to DNA damage from utilizing predominantly the homologous recombination (HR) rather than NHEJ. The consequence of this HR-to-NHEJ switch is that now fibroblasts can continue to proliferate under genotoxic stress, which is highly abundant within injured kidneys, ultimately contributing to progression of chronic kidney disease (cf. FIG. 1).

The present inventors have identified ways of targeting the new pathway, as indicated in FIG. 1. They found that removal of the critical exon 10 can be therapeutically induced by administration of antisense compounds and also through demethylation of the site at intron 9-10. They identified SNP rs1325938 as having high predictive value as a biomarker for the progression of chronic kidney disease. They furthermore found that inhibition of the disadvantageous tyrosine phosphatase activity of EYA1A, for example through orthovanadate, attenuates fibrosis. They also found that inhibition of NHEJ, which results from EYA1A abundance, through the ligase IV inhibitor SCR7 or administration of in vivo morpholinos targeting 53Bp1, attenuates kidney fibrosis. Their data suggests that these findings are not limited to the kidney, but also apply to fibrosis in other organs and cancer.

An antisense compound according to the present disclosure may be directed against the generation of transcript variant EYA1A by splicing. More precisely, the antisense compound may be directed against one or both of the splice junctions flanking exon 10, thereby modulating exon 10 splicing.

An antisense compound according to the present disclosure may also be directed against the splice product termed EYA1A herein. More specifically, an antisense compound may serve in inhibiting translation of EYA1A. Thereby formation of EYA1A is reduced or prevented.

An antisense compound directed against the intron 9-10/exon 10 and/or exon 10/intron 10-11 splice junctions, is able to prevent the inclusion of exon 10 of the sequence that encodes the protein EYA1 into this protein, thereby preventing the formation of splice variant EYA1A. An antisense oligonucleotide directed against the intron 9-10/exon 10 and exon 10/intron 10-11 splice junctions is also abbreviated EYA1Δe10-ASO herein. An antisense oligonucleotide directed against the intron 9-10/exon 10 splice junction is also abbreviated EYA1Δe10-5'ASO herein. An antisense oligonucleotide directed against the exon 10/intron 10-11 splice junction is also abbreviated EYA1Δe10-5'ASO herein.

The exons of the human EYA1 encoding gene can be identified in the Ensembl entry (supra) of human EYA1. Exon 9 has been assigned exon ID ENSE00003547586. It is found at positions 322203 to 322286 of the sequence of EYA1 at positions 71,197,433-71,592,025 on human chromosome 8 identified in Ensembl by accession number ENSG00000104313. Exon 9 can furthermore be found at positions 283308 to 283391 of the NCBI reference sequence NG_011735.3 (supra, version 3 as of 24 Feb. 2018). Exon 10 has been assigned Ensembl exon ID ENSE00003642688, and is found at positions 347334 to 347423 of the sequence of EYA1 at positions 71,197,433-71,592,025 on human chromosome 8 identified in Ensembl by accession number ENSG00000104313 (Ensembl release 98 of September 2019. Exon 11 has been assigned Ensembl exon ID ENSE00003481860, and is found at positions 375003 to 375061 of the sequence of EYA1 identified in Ensembl by accession number ENSG00000104313. Exon 11 can furthermore be found at positions 336,108 to 336,166 of the NCBI reference sequence NG_011735.3.

An antisense compound directed against the intron 9-10/exon 10 splice junction includes a sequence that is at least 90% identical to the sequence of SEQ ID NO: 5, or a complement thereof. In some embodiments the antisense compound directed against the intron 9-10/exon 10 splice junction includes a sequence that is at least 94% identical to the sequence of SEQ ID NO: 5, or a complement thereof. In some embodiments the antisense compound directed against the intron 9-10/exon 10 splice junction includes a sequence that is at least 96% identical to the sequence of SEQ ID NO: 5, or a complement thereof. In some embodiments the antisense compound directed against the intron 9-10/exon 10 splice junction includes a sequence that is at least 98% identical to the sequence of SEQ ID NO: 5, or a complement thereof. In some embodiments the antisense compound directed against the intron 9-10/exon 10 splice junction includes a sequence that is at least 99% identical, or at least 99.5% identical to the sequence of SEQ ID NO: 5, or a complement thereof. In some embodiments the antisense compound directed against the intron 9-10/exon 10 splice junction includes a sequence that is identical to the sequence of SEQ ID NO: 5, or a complement thereof. In some embodiments the antisense compound directed against the intron 9-10/exon 10 splice is the sequence of SEQ ID NO: 5, or a complement thereof.

In some embodiments the antisense compound directed against the exon 10/intron 10-11 splice junction includes a sequence that is at least 90% identical to the sequence of SEQ ID NO: 4, or a complement thereof. In some embodiments the antisense compound directed against the exon 10/intron 10-11 splice junction includes a sequence that is at least 94% identical to the sequence of SEQ ID NO: 4, or a complement thereof. In some embodiments the antisense compound directed against the exon 10/intron 10-11 splice junction includes a sequence that is at least 96% identical to the sequence of SEQ ID NO: 4, or a complement thereof. In some embodiments the antisense compound directed against the exon 10/intron 10-11 splice junction includes a sequence that is at least 98% identical to the sequence of SEQ ID NO: 4, or a complement thereof. In some embodiments the antisense compound directed against the exon 10/intron 10-11 splice junction includes a sequence that is at least 99% identical, or at least 99.5% identical to the sequence of SEQ ID NO: 4, or a complement thereof. In some embodiments the antisense compound directed against the exon 10/intron 10-11 splice junction includes a sequence that is identical to the sequence of SEQ ID NO: 4, or a complement thereof. In some embodiments the antisense compound directed against the exon 10/intron 10-11 splice is the sequence of SEQ ID NO: 4, or a complement thereof.

As already noted above, an antisense compound as disclosed herein may contain one or more nucleosides having modified sugar moieties.

An antisense compound according to the present disclosure can be conveniently and routinely made through the well-known technique of solid phase synthesis. Equipment for such synthesis is commercially available through various sources. Any other means for such synthesis known in the art may additionally or alternatively be employed. It is well known to use similar techniques to prepare oligonucleotides such as a phosphorothioate and an alkylated derivative.

The protein EYA1 is in some embodiments a variant of a naturally occurring EYA1 protein. For example, it may be negligible to exchange certain amino acid residues that are nor critical for allowing the binding to other factors, the metal binding and/or the protein tyrosine phosphatase activity or the protein serine and protein threonine phosphatase activity. It may also be desired modify a EYA1 protein at one or more positions for detection purposes. A respective variant is a protein that contains an amino acid sequence that has at least about 98% sequence identity to a naturally existing EYA1 protein. In some embodiments a respective variant contains an amino acid sequence that has at least about 99% sequence identity to a naturally existing EYA1 protein. A variant of the EYA1 protein is typically functional in that it allows the above described catalytic activity, and/or RNA binding and/or physiological activity.

Typically the difference from a naturally occurring EYA1 protein is a substitution. In some embodiments the difference from a naturally occurring EYA1 protein is a deletion. A variant of a naturally occurring EYA1 protein may be a gene obtained from the expression of a gene sequence altered by site specific mutagenesis.

Variants of a naturally occurring EYA1 protein may be prepared by protein and/or chemical engineering, introducing appropriate modifications into the nucleic acid sequence encoding the polypeptide, or by protein/peptide synthesis. A variant may be obtained by any combination(s) of one or more deletions, substitutions, additions and insertions to nucleic acid and/or the amino acid sequence, provided that the obtained polypeptide defines a functional EYA1 protein. In some embodiments a variant of a polypeptide provided herein differs from a particular sequence of a polypeptide provided herein by up to five substitutions. A substitution in an amino acid sequence of a polypeptide provided herein may be a conservative substitution. Examples of conservative substitutions include:

1. Substituting alanine (A) by valine (V);
2. Substituting arginine (R) by lysine (K);
3. Substituting asparagine (N) by glutamine (Q);
4. Substituting aspartic acid (D) by glutamic acid (E);
5. Substituting cysteine (C) by serine (S);
6. Substituting glutamic acid (E) by aspartic acid (D);
7. Substituting glycine (G) by alanine (A);
8. Substituting histidine (H) by arginine (R) or lysine (K);
9. Substituting isoleucine (I) by leucine (L);
10. Substituting methionine (M) by leucine (L);
11. Substituting phenylalanine (F) by tyrosine (Y);
12. Substituting proline (P) by alanine (A);
13. Substituting serine (S) by threonine (T);
14. Substituting tryptophan (W) by tyrosine (Y);

15. Substituting phenylalanine (F) by tryptophan (W); and/or
16. Substituting valine (V) by leucine (L) and vice versa.

A variant of a naturally occurring EYA1 protein may include one or more, such as two or three of such conservative substitutions. In some embodiments a polypeptide according to this disclosure includes a sequence that has four or more conservative substitutions in comparison to a naturally occurring EYA1 protein. In some embodiments a variant includes a sequence that has five or more, such as six or more conservative substitutions.

Non-conservative substitutions may lead to more substantial changes, e.g., with respect to the charge, dipole moment, size, hydrophilicity, hydrophobicity or conformation of the polypeptide. In some embodiments the polypeptide includes one or more, such as two non-conservative substitutions. In some embodiments a variant of a naturally occurring EYA1 protein includes three or four non-conservative substitutions. The variant may also include five or more, e.g. six, or seven or more of such non-conservative substitutions.

Provided is also the use of the methylation status of a CpG island in the nucleic acid sequence of a subject encoding EYA1 in assessing the risk of the subject of developing or progression of a disease that involves aberrant fibroblast proliferation, e.g. developing fibrosis or of progressing fibrosis in the subject. The CpG island is located at positions corresponding to positions 307586 to 307789 of GenBank accession number NG_011735, version 3 of the sequence, located upstream exon 10. Elevated methylation of the CpG island is associated with splicing that results in inclusion of exon 10 in the transcribed EYA1 protein.

Disclosed is furthermore a method of preventing, treating and/or delaying progression of aberrant fibroblast proliferation by administering to a subject an antisense oligonucleotide against a sequence included in the splice junction of intron 9-10/exon 10, and/or an antisense oligonucleotide against a sequence included in the splice junction of intron 9-10/exon 10 exon 10/intron 10-11 of the sequence encoding the protein EYA1. The sequence included in the splice junction of intron 9-10/exon 10 may include the sequence of SEQ ID NO: 5 or of SEQ ID NO: 27 or consist of the sequence of SEQ ID NO: 5 or of SEQ ID NO: 27. The sequence included in the splice junction of intron 9-10/exon 10 may also include a portion of the sequence of SEQ ID NO: 5 or of SEQ ID NO: 27 or be a portion of the sequence of SEQ ID NO: 5 or of SEQ ID NO: 27. The sequence included in the splice junction of exon 10/intron 10-11 of the sequence encoding the protein EYA1 may include the sequence of SEQ ID NO: 4 or of SEQ ID NO: 14 or consist of the sequence of SEQ ID NO: 4 or of SEQ ID NO: 14. The sequence included in the splice junction of intron 9-10/exon 10 may also include a portion of the sequence of SEQ ID NO: 4 or of SEQ ID NO: 14 or be a portion of the sequence of SEQ ID NO: 4 or of SEQ ID NO: 14.

This method can thus be understood as antisense therapy. Without being bound by theory, the antisense oligonucleotide is thought to bind to the pre-mRNA transcript produced by the EYA1 gene at the respective splice junction. Thereby the particular splice junction is blocked and in effect hidden. As a result the inclusion of exon 10 into the mature mRNA is prevented. Exon skipping is being effected or promoted. Thereby the formation of isoform EYA1C can be thought to in effect be enhanced, and the amount of isoform EYA1A can be thought to be reduced. Put differently, the ratio between isoform EYA1C and EYA1A can be thought to be shifted toward isoform EYA1C.

Disclosed herein is also a method of preventing, treating or delaying onset or progression of a disease that involves aberrant fibroblast proliferation, such as fibrosis, in a subject, which involves reducing the methylation status of the above defined CpG island that is located upstream exon 10 of the sequence encoding the protein EYA1. By reducing the methylation status of the CpG island, exon 10 splicing is controlled to effect an increased removal of exon 10 from the splice products. As a result, the amount of EYA1A is being reduced. Typically, the amount of EYA1C is being increased.

The method involves the use of a nucleic acid molecule that encodes a protein or a catalytically active domain or portion thereof, that is a DNA methyltransferase (DNMT) or a protein of the Ten-Eleven-Translocation (TET) family. These proteins, as well as a catalytically active domain or portion thereof, are capable of modifying the methylation state of DNA. The TET protein may for instance be TET3 or TET1. Details on a suitable embodiment of a respective nucleic acid molecule can be found in e.g. US patent applications US 2016/0010076, US 2018/0208921. Further examples of suitable nucleic acid molecules can be found in Liu et al., Cell (2016) 167, 233-247, and in and in Xu et al., Nature Communications (2018) 9, 3509. The nucleic acid molecule that includes a sequence encoding a DNA methyltransferase or a TET protein may be included in a vector.

In some embodiments the method involves the use of a nucleic acid molecule that includes a sequence encoding an endonuclease 9 and a TET3 catalytic domain. The nucleic acid molecule furthermore includes the sequence of a single guide RNA (sgRNA). The sequence of the sgRNA targets the nucleic acid molecule to the CpG island. The sequence encoding the endonuclease 9 may encode a catalytically inactive Cas9 protein. The sequence encoding the endonuclease 9 may encode a double mutated endonuclease deactivated Cas9 protein, a so called "deactivated high-fidelity Cas9" (dHFCas9), as described in Xu et al. (2018, supra). In this Cas9 protein endonuclease catalytic residues D10A and H840A have been mutated to avoid occurrence of DNA cleavage. The TET3 catalytic domain may be fused to the C-terminal domain of the Cas9 protein, as disclosed in Xu et al.

The protein TET3 may in some embodiments be a human protein of SwissProt/Uniprot accession number O43151, version 3 of the sequence of 10 Jun. 2008, version 137 of the database entry of 18 Sep. 2019. The protein TET3 may for example be isoform 1 of identifier O43151-1 of SwissProt/Uniprot accession number O43151. The TET3 catalytic domain may be the C-terminal double stranded p-helix domain of the TET3 protein that includes the 2-oxoglutarate binding region of positions 1553 to 1555 of the protein, and the substrate binding region of positions 1559 to 1561 of the protein of SwissProt/Uniprot accession number O43151. In one embodiment the TET3 catalytic domain is defined by amino acid positions 851 to 1795 of the protein.

The sequence of the sgRNA may be arranged in an orientation that is C-terminally of the TET3 catalytic domain. As noted above, the sequence of the sgRNA is capable of targeting the respective nucleic acid molecule, e.g. a nucleic acid molecule transcribed from the above vector, to the CpG island. The sequence of the sgRNA may include a portion of SEQ ID NO: 6, for example as a short crRNA sequence. A respective targeting sequence of the sgRNA may have a typical length, such as about 20 bases. In some embodiments the targeting sequence of the sgRNA has a length of about 22 bases or of about 18 bases.

The nucleic acid molecule is in some embodiments included in a lentiviral vector. In some embodiments the nucleic acid molecule is included in an Adeno-associated virus (AAV) vector. A lentiviral system is capable of infection almost any mammalian cell type. Targeted delivery can for example be achieved by local injection as disclosed in Xu et al., Nat. Commun. (2018) 29, 9(1), 3509, doi: 10.1038/s41467-018-05766-5. With regard to an Adeno-associated virus system, different serotypes of AAV exist, which affect the tissue specificity of AAV infection. A suitable fibroblast-specific serotype is for example AAV9-SLRSPPS.

A method disclosed herein that involves administering a nucleic acid molecule that includes an endonuclease 9 encoding sequence, a TET domain, and a sequence encoding an sgRNA specific for a portion of a CpG island of the gene encoding EYA1 can be understood to be a method of gene therapy based on the CRISPR gene editing system. The CRISPR (Clustered Regularly Interspaced Short Palindromic Repeats) gene editing system includes the use of an endonuclease 9 such as the CRISPR-associated protein-9 nuclease (Cas9) from *Streptococcus pyogenes*, cf. above. A respective method may include administering to the subject a therapeutically effective amount of the nucleic acid molecule that includes an endonuclease 9 encoding sequence, a TET domain, and a sequence encoding the sgRNA. Cas9-based gene drive activity can be regulated as disclosed in international patent application WO 2019/067011.

Disclosed is also the use of a nucleic acid ligase IV inhibitor in a method of preventing, treating or delaying progression of a disease involving aberrant fibroblast proliferation. Examples of suitable a nucleic acid ligase IV inhibitors are depicted in FIGS. 36 A to E. Further suitable nucleic acid ligase IV inhibitors have been disclosed in Srivastava, M., et al., Cell (2012) 151(7), 1474-1487. In some embodiments the nucleic acid ligase IV inhibitor is SCR5 or SCR6. In some embodiments the nucleic acid ligase IV inhibitor is SCR7. In some embodiments the nucleic acid ligase IV inhibitor is SCR8 or SCR9. In some embodiments the nucleic acid ligase IV inhibitor is SCR10 or SCR11. In some embodiments the nucleic acid ligase IV inhibitor is SCR12 or SCR13. In some embodiments the nucleic acid ligase IV inhibitor is SCR14 or L67.

Disclosed is furthermore a method of identifying a candidate compound for treating fibrosis in a subject. The identified candidate compound may be further tested for its suitability of being administered to a subject. In the method a test compound is allowed to contact a nucleic acid molecule that includes the sequence encoding the protein EYA1. An illustrative example is a nucleic acid sequence that is substantially identical to or that is defined by the sequence of GenBank accession number NG_011735. On the nucleic acid molecule the sequence encoding the protein EYA1 is operably linked to a promoter.

In some embodiments the method involves providing the test compound. In some embodiments the method involves providing the nucleic acid molecule that includes the sequence encoding the protein EYA1. Allowing contacting of the test compound and the nucleic acid molecule is carried out within a mammalian expression system. The sequence encoding the protein EYA1 includes a sequence that is essentially identical to positions 307586 to 307789 of GenBank accession number NG_011735, version 3 of the sequence, or the complement thereof. In some embodiments the sequence encoding the protein EYA1 includes a sequence that is essentially identical to SEQ ID NO: 6, or the complement thereof.

After allowing the nucleic acid molecule and the test compound to contact each other, the method furthermore includes determining the methylation status of the sequence that is essentially identical to positions 307586 to 307789 of GenBank accession number NG_011735, or the complement thereof. In some embodiments the method furthermore includes determining the methylation status of the sequence that is essentially identical to SEQ ID NO: 6, or the complement thereof. The methylation status is compared to a control. The control may for example be the absence of the test compound. The control may also be the presence of a compound known not to have an effect on the methylation status of the sequence essentially identical to positions 307586 to 307789 of GenBank accession number NG_011735 or to SEQ ID NO: 6, or a respective complement thereof. A decreased methylation status of the sequence essentially identical to positions 307586 to 307789 of GenBank accession number NG_011735 or of the sequence defined by to positions 307586 to 307789 of GenBank accession number NG_011735, or of the respective complement thereof, relative to the control, indicates that the test compound is a candidate compound for treating fibrosis in a subject. Likewise, a decreased methylation status of the sequence essentially identical to SEQ ID NO: 6 or of the sequence defined by SEQ ID NO: 6, or of a respective complement thereof, relative to the control, indicates that the test compound is a candidate compound for treating fibrosis in a subject.

In some embodiments a measurement may be compared to a predetermined threshold value. A predetermined threshold value may in some embodiments be set on the basis of data collected from preceding measurements using compounds known to modulate, e.g. activate or inhibit the methylation status of the sequence of positions 307586 to 307789 of GenBank accession number NG_011735, or the sequence essentially identical thereto, or a respective complement thereof. A predetermined threshold value may also be set on the basis of data collected from preceding measurements using compounds known to modulate, e.g. activate or inhibit the methylation status of the sequence of SEQ ID NO: 6, or the sequence essentially identical thereto, or a respective complement thereof.

In some embodiments a certain percentile of such data may be used as a threshold value. The range of the values of a set of data obtained from available data can be divided into 100 equal parts, i.e. percentages of the range can be determined. A percentile represents the value within the respective range below which a certain percent of the data fall, in other words the percentage of the values that are smaller than that value. For example the 95th percentile is the value below which 95 percent of the data are found. In some embodiments the methylation status of the sequence of positions 307586 to 307789 of GenBank accession number NG_011735 or of the sequence of SEQ ID NO: 6, or of a sequence essentially identical thereto, or a respective complement thereof, may be regarded as decreased or low if it is below the $90^{th}$ percentile, or below the $80^{th}$ percentile. In some embodiments the methylation status may be regarded as decreased or low if it is below the $70^{th}$ percentile.

Disclosed is furthermore a method of identifying a candidate compound for treating fibrosis in a subject. The identified candidate compound may be further tested for its suitability of being administered to a subject. In the method a test compound is allowed to contact the protein EYA1 or a functional fragment thereof. An illustrative example is a nucleic acid sequence that is substantially identical to or that is defined by the sequence of GenBank accession number NG_011735.

In some embodiments the method involves providing the test compound. In some embodiments the method involves providing the EYA1 protein. Allowing contacting of the test compound and the EYA1 protein is generally carried out under conditions where the EYA1 protein is capable of hydrolysing phosphoserine, phosphothreonine and/or phosphotyrosine residues of a target protein, i.e. a substrate. Suitable conditions include the presence of an aqueous medium that contains a buffer compound as well as an inorganic ion such as a magnesium salt dissolved in the aqueous medium.

Buffer compounds are well established in the art. Examples of buffers include, but are not limited to, solutions of salts of phosphate, carbonate, succinate, carbonate, citrate, acetate, formate, barbiturate, oxalate, lactate, phthalate, maleate, cacodylate, borate, N-(2-acetamido)-2-amino-ethanesulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethanesulfonic acid) (also called PIPES), (2-[tris(hydroxymethyl)-methylamino]-1-ethansulfonic acid (also called TES), 2-cyclohexyl-amino-ethansulfonic acid (also called CHES) and N-(2-acetamido)-iminodiacetate (also called ADA). Any counter ion may be used in these salts; ammonium, sodium, and potassium may serve as illustrative examples. Further examples of buffers include, but are not limited to, triethanolamine, diethanolamine, ethylamine, triethylamine, glycine, glycylglycine, histidine, tris(hydroxymethyl)aminomethane (also called TRIS), bis-(2-hydroxyethyl)-imino-tris(hydroxymethyl) methane (also called BIS-TRIS), and N-[Tris(hydroxymethyl)-methyl]-glycine (also called TRICINE), to name a few. A respective buffer may be an aqueous solution of such buffer compound or a solution in a suitable polar organic solvent.

The method furthermore includes allowing the EYA1 protein to hydrolyse phosphoserine, phosphothreonine and/or phosphotyrosine residues on a suitable substrate such as histone H2A variant H2A.X. In some embodiments the sequence encoding the protein EYA1 includes a sequence that is essentially identical to SEQ ID NO: 6, or the complement thereof. In some embodiments the method involves providing the substrate, e.g. histone H2A variant H2A.X. The method also includes determining the phosphoserine phosphatase activity, phosphothreonine phosphatase activity and/or the phosphotyrosine phosphatase activity of EYA1 relative to a control or relative to a predetermined threshold value.

Serine/threonine phosphatase and tyrosine phosphatase activity may be determined using a colorimetric technique, for example based on p-nitrophenyl phosphate or malachite green. Serine/threonine phosphatase and tyrosine phosphatase activity may also be determined using a $^{32}$P-labeled protein substrate. Details on a typical procedure can for instance be found in McAvoy T., and Nairn, A. C., Curr Protoc Mol Biol. (2010) October, unit18.18. doi:10.1002/0471142727.mb1818s92. In order to determine the amount of phosphate released, a phosphate standard may be used as a reference, for example a solution of $KH_2PO_4$ of known concentration, which may be diluted to different final concentrations.

The control may again in some embodiments be the absence of the test compound. The control may also be the presence of a compound known not to have an effect on the phosphoserine phosphatase activity, phosphothreonine phosphatase activity and/or the phosphotyrosine phosphatase activity of EYA1.

If an increased phosphoserine phosphatase activity and/or a reduced phosphotyrosine phosphatase activity of EYA1 relative to the control or the predetermined threshold value is measured, the test compound is a candidate compound for treating fibrosis in a subject.

An example of a suitable compound for treating a disease involving aberrant fibroblast proliferation such as fibrosis identified by an in vitro screen is an inhibitor of the phosphotyrosine phosphatase activity of EYA1 of the following formula:

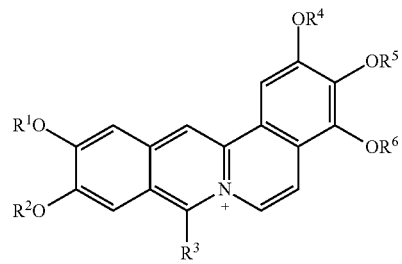

This compound is a cation, which is associated with a suitable anion. A suitable anion may be an organic acid such as acetic acid or propionic acid. A suitable anion is for example 2-sulfoacetic acid or a 3-sulfopropanoic acid. The respective salt is a sulfoacetate and a sulfopropanoate, respectively.

In the above formula $R^1$ and $R^2$ are independently selected $C_1$-$C_6$ alkyl moieties. $R^1$ and $R^2$ may for example be independently selected from ethyl and methyl. $R^3$ may be methyl or H. $R^4$, $R^5$ and $R^6$ are independently selected from H, methyl and ethyl. In some embodiments $R^6$ is H and $R^4$ and $R^5$ are independently selected from methyl and ethyl. In some embodiments both $R^4$ and $R^5$ are methyl. In one embodiment $R^1$ to $R^5$ are methyl and $R^6$ is H.

A further example of an inhibitor of the phosphotyrosine phosphatase activity of EYA1 suitable for treating a disease involving aberrant fibroblast proliferation such as fibrosis that has been identified by an in vitro screen is a polyoxomolybdate phosphate salt such as a $\{Mo_{12}\}$-type polyoxomolybdate. The phosphate may be a $[Mo_{12}O_{36}(PO_4)]$ salt, for example the disodium or the dipotassium salt ($HMo_{12}Na_2O_{40}P$ and $HMo_{12}K_2O_{40}P$).

A further example of an inhibitor of the phosphotyrosine phosphatase activity of EYA1 suitable for treating a disease involving aberrant fibroblast proliferation such as fibrosis that has been identified by an in vitro screen is a compound of the following formula:

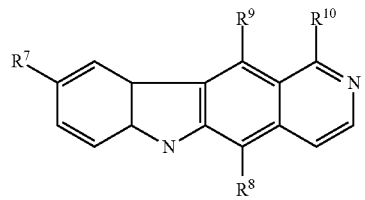

In this compound $R^7$ may be H, OH, $C_1$-$C_6$ alkoxy or phenoxy. In one embodiment $R^7$ is H. $R^8$ and $R^9$ are independently selected from H and methyl. In some embodiments both $R^8$ and $R^9$ are methyl. $R^{10}$ may be H, methyl, ethyl or (1-methyl-4-nitropyrazol-5-yl). In some embodiments both $R^7$ and $R^{10}$ are H. In one embodiment $R^7$ and $R^{10}$ are H, and $R^8$ and $R^9$ are methyl.

A further suitable compound is caffeine. Yet further suitable compounds are a vanadate ($VO_4^{3-}$) such as sodium orthovanadate and a pervanadate, i.e. a complex of vanadate with hydrogen peroxide. An overview on protein tyrosine phosphatase inhibitors, which discloses a number of further suitable compounds, has been provided by Barr, A. J., Future Med. Chem. (2010) 2(10), 1563-1576.

With regard to modulators of the phosphotyrosine phosphatase activity of EYA1, the inventors screened a small molecule library, namely the NCI "Mechanistic Set II library", obtained from the open chemical repository of the Developmental Therapeutics Program (DTP) of the National Cancer Institute, illustrated by FIG. 14.

Strong inhibitors identified were Dibenzo(a,g)quinolizinium, 2,3,10,11-tetramethoxy-8-methyl-sulfoacetate (Coralyne sulfoacetate, CAS No. 38989-37-6, NSC No. 154890), [$Mo_{12}O_{36}(PO_4)$] disodium salt (Polyoxomolybdate phosphate complex, disodium salt, NSC No. 622116), 5-Methyl-6H-pyrido(4,3-b)carbazole (11-Dimethylellipticine, CAS No. 4238-66-8, NSC 87206), and Hexapotassium hexatriaconta-p-oxooctadecaoxobis [μ9-[phosphato(3-)-κO:κO:κO: κO':κO':κO":κO":κO''':κO''']octadeca-molybdate(6-) (NSC No. 622124), as well as $C_{26}H_{17}ClN_2O_5$ (NSC No. 641253).

Strong inducers identified were 3-hydroxy-2-(2-quinoxalinyl)-1-indenone (NSC No. 634224), 2-(2-benzothiazolyl)-6-phenyl-3(2H)-pyridazinone (NSC No. 629659), alpha-(p-chlorophenyl)-4-oxo-2,5-cyclohexadiene-.delta.1, .alpha.-acetonitrile oxime (NSC No. 405158), and (Z)-3-[3-(dimethylamino)phenyl]-2-phenylprop-2-enenitrile (NSC No. 667251).

Therapeutic Applications

A compound for preventing, treating or delaying progression of a disease that involves aberrant fibroblast proliferation, e.g. fibrosis or cancer, in a subject as disclosed herein, which may for instance be a low molecular weight compound may be provided in a composition which further includes a suitable carrier, excipient or diluent. In typical embodiments a respective composition includes a compound described herein. Such a composition may, e.g., be a diagnostic, a cosmetic or a pharmaceutical composition. For therapeutic or cosmetic purposes, the composition is a pharmaceutical composition including a pharmaceutical carrier, excipient or diluent, i.e. not being toxic at the dosages and a concentration employed.

A compound for preventing, treating or delaying progression of a disease that involves aberrant fibroblast proliferation as disclosed herein is useful as a medicament. Typically, such a medicament includes a therapeutically effective amount of a molecule as disclosed above. Accordingly, a respective molecule can be used for the production of a medicament useful in the treatment of fibrosis.

In one aspect, a method of treating fibrosis is provided. The method includes the steps of administering a pharmaceutically effective amount of a molecule as described herein, such as a low molecular weight compound, to a subject in need thereof. In one embodiment, the pharmaceutical composition described above, which includes such pharmaceutically effective amount of the compound is administered to the subject. The medicament referred to above may be administered to a subject.

The subject in need of a treatment can be a human or a non-human animal. Typically the subject is a mammal, e.g., a mouse, a rat, rabbit, a hamster, a dog, a cat, a monkey, an ape, a goat, a sheep, a horse, a chicken, a guinea pig or a pig. In typical embodiments, the subject is diagnosed with a fibrosis or may acquire such a disorder.

The compound for treating fibrosis as disclosed herein may be included in a pharmaceutical composition as indicated above. The pharmaceutical composition may be applied by one or more of various suitable routes of administration. Administration can for instance be conducted parenterally. In some embodiments administration is carried out intramuscularly. In some embodiments administration is carried out intravenously as a bolus or by continuous infusion. Administration is in some embodiments conducted intraarticularly. In some embodiments administration is done intrasynovially. Administration may in some embodiments be subcutaneously. In some embodiments administration is carried out topically, e.g., to the skin or the eye. Administration is in some embodiments carried out rectally. In some embodiments administration is done dermally such as intradermally, subcutaneously or transdermally. Administration can in some embodiments be performed locally. Further suitable modes of administration include, but are not limited to intracerebrally, intracerebrospinally, intrathecally, epidurally, or intraperitoneally; orally; urogenitally; intravitreally; systemically; intravenously; intraocularly; oticly; intranasally; by inhalation; sublingually; buccally, for example. Typical routes of administration are the topical, rectal, local, intranasal, intravenous and/or intradermal routes of administration.

Article of Manufacture

In a further aspect, an article of manufacture such as a kit is provided. The article of manufacture includes matter, e.g. material, useful for (i) the treatment, prevention of delay of progression of fibrosis; (ii) diagnostic or (iii) cosmetic purposes. The article of manufacture may include instructions for use and one or more containers. Suitable containers include, for example, bottles, vials, syringes, cartridges, plates and test tubes and may be made from a variety of materials such as glass or plastic. At least one container holds a composition that includes a compound for treating fibrosis as disclosed herein. The container may have a sterile access port. A respective container is typically labelled.

The reagents may for example provided in predetermined amounts of dry powders, usually lyophilized, including excipients which after dissolution will provide a reagent solution having the appropriate concentration. Other additives such as stabilizers and/or buffers may also be included. If the binding member is labelled with an enzyme, the kit will typically include the according substrates and cofactors.

The instructions for use may provide indications that the composition is used for the treatment, prevention and/or delay of progression of a disorder of choice; or instructions for performing a detection or diagnostic assay. The instructions may be provided on a label and/or on a package insert.

The listing or discussion of a previously published document in this specification should not necessarily be taken as an acknowledgement that the document is part of the state of the art or is common general knowledge.

While embodiments of the invention have been illustratively described, it is to be understood that the invention is not limited thereto but may be otherwise variously embodied and practiced within the scope of the appending claims. The invention may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following are examples, illustrating the methods, uses and agents disclosed herein. It is understood that various other embodiments may be practiced, given the general description provided above.

EXAMPLES

The examples illustrate techniques that can be used in a method and a use disclosed herein. The examples are presented in the form of an overview, with details of the methods and reagents following thereafter.

Figure 2L:
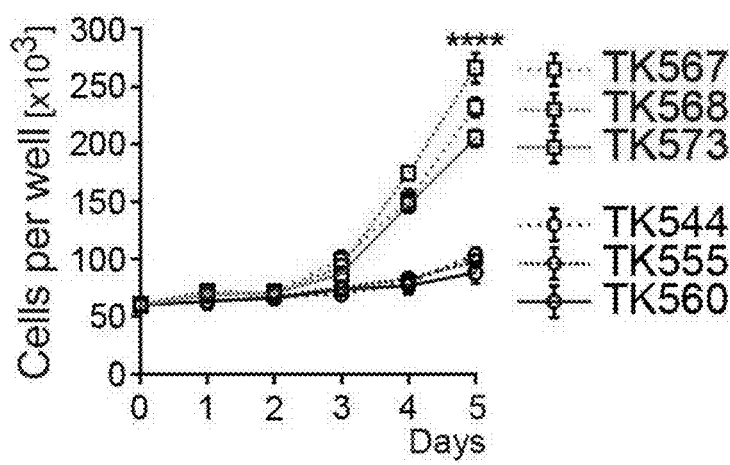
FIG. 2L depicts the accumulation of human fibroblasts isolated from fibrotic kidney biopsies (TK567, TK568, and TK573) in comparison to primary fibroblasts from non-fibrotic kidneys (TK544, TK555, and TK560) in culture. Primary human kidney fibroblast cultures were seeded at a density of 60,000 per well and proliferative activity was determined at indicated time points (n=3 independent replicates, data are presented as means±s.d., **p<0.0001, values of p were calculated using Student's t test comparing non-fibrotic and fibrotic fibroblast cultures).
Figure 2M:
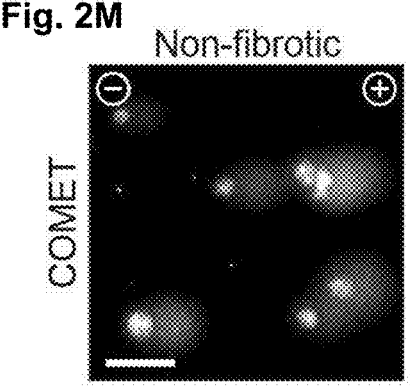
FIG. 2M shows fibroblasts isolated from non-fibrotic and fibrotic kidneys analyzed by neutral COMET assay (scale bars: 10 µm).
Figure 2N:
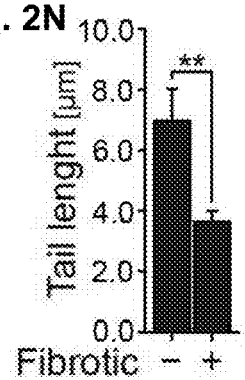
FIG. 2N is a graph summarizing average tail lengths of fibroblasts analyzed by neutral COMET assay (cf.

Example 1—Fibrotic Fibroblasts Resist Genotoxic Stress by Accelerated Recruitment of High-Fidelity NHEJ DDR The extent of DNA damage is commonly assessed by immunolabeling with antibodies directed at histone γH2A.X. Histone H2A.X contains a conserved $S^{139}QEY^{142}$-COOH motif which is subject to post-translational modifications upon DNA damage involving serine 139 (S139) and tyrosine 142 (Y142) residues: While H2A.X S139 is phosphorylated upon double strand breaks ($\gamma H2A.X^{pS139}$, then commonly referred to as γH2A.X), the phorphorylation status of the γH2A.X Y142 residue ($\gamma H2A.X^{pY142}$) is considered to serve as a modifier for ensuing DDR. γH2A.X immunolabeling and G2/M DNA damage checkpoint activation are highly abundant in fibrotic fibroblasts of chronically injured parenchymal organs including kidney, heart, lung and liver (FIG. 2A-K, FIG. 3A-E). Based on the observation of H2A.X enrichment within renal fibroblasts (FIG. 4A-G, 5A-H) and a previous established hereditary link of impaired DDR and fibrosis in nephropathies (Zhou, W., et al., Nat Genet (2012) 44, 910-915), the inventors decided to focus on the kidney. Human fibroblasts isolated from fibrotic kidney biopsies (TK567, TK568, TK573) accumulated more rapidly than primary fibroblasts from non-fibrotic kidneys in culture (TK544, TK555, TK560, FIG. 2L) as had been reported in numerous previous studies proliferation (Tampe & Zeisberg, 2014, supra; Bechtel et al., 2010, supra; LeBleu et al., 2013, supra; Rodemann & Muller, 1990, supra), seemingly contradicting observed DNA damage checkpoint activation.

Figure 2O:
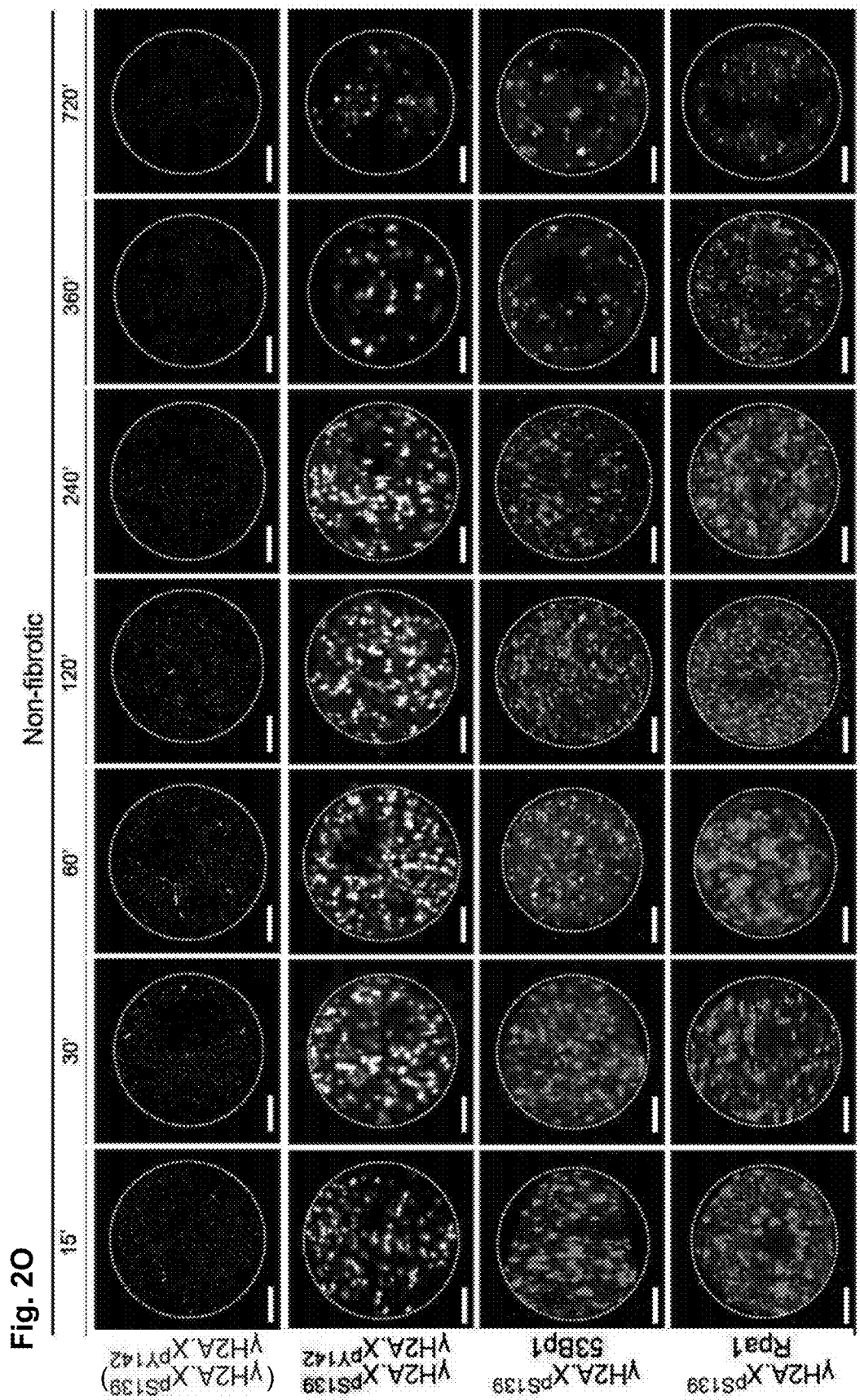
FIGS. 2O and 2P show representative photomicrographs of primary human fibroblast cultures isolated from non-fibrotic kidneys (FIG. 2O) and fibrotic kidneys (FIG. 2P) at indicated time points after NCS exposure. The respective upper two panels show photomicrographs of fibroblast cultures labelled for $\gamma H2A.X^{pS139}/\gamma H2A.X^{pY142}$ (scale bars: 4 µm). The top panel shows the same photomicrographs as the panel below, with any other colour signals than green colour reduced to 0. The lower two panels show photomicrographs of fibroblast cultures labelled for $\gamma H2A.X^{pS139}/$ 53Bp1 (penultimate panel, scale bars: 4 µm) and $\gamma H2A.X^{pS139}/Rpa1$ (bottom panel, scale bars: 4 µm).
Figure 2P:
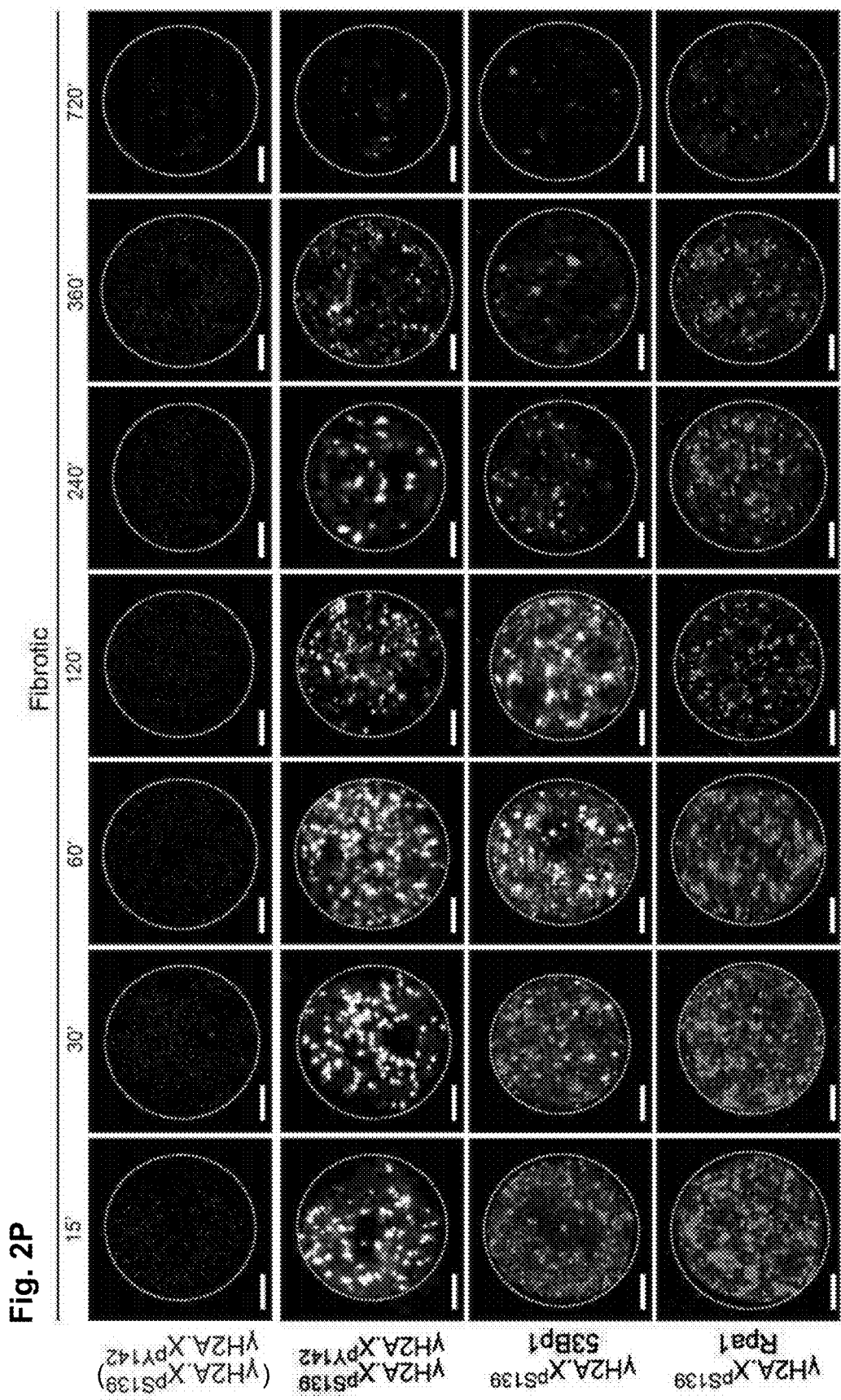
Figure 3A:
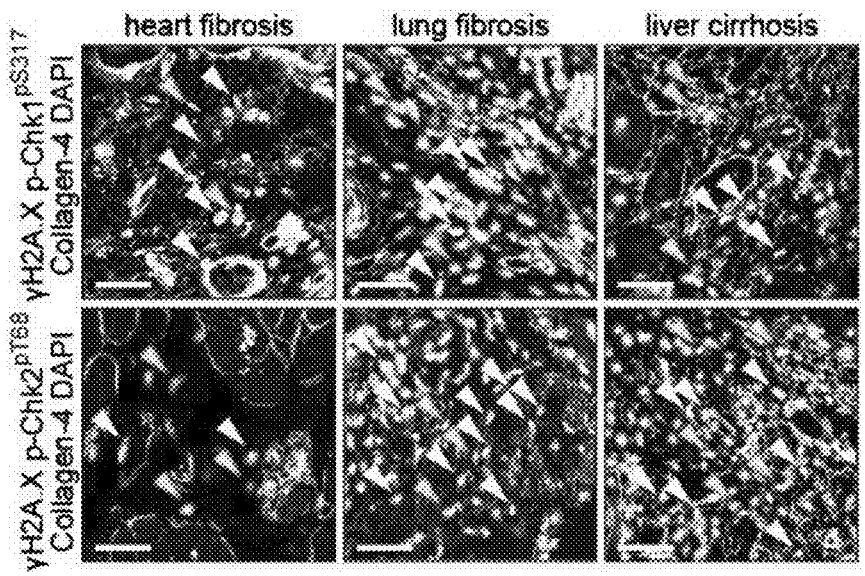
FIG. 3A shows representative photomicrographs of heart and liver sections labelled for $\gamma H2A.X/p$-Chk1$^{pS317}$/Collagen-4 (scale bars: 25 µm) and $\gamma H2A.X/p$-Chk2$^{pT68}$/Collagen-4 (scale bars: 25 µm).
Figure 3B:
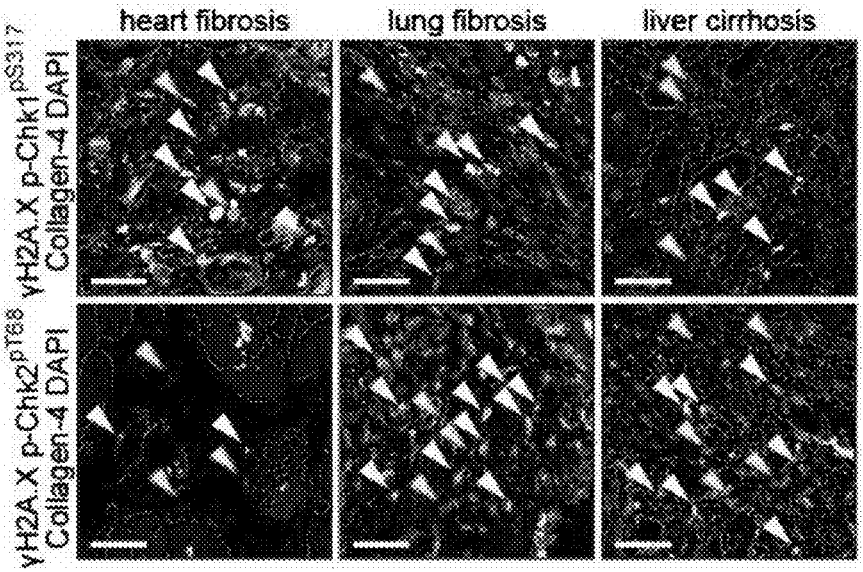
FIG. 3B shows the same photomicrographs as FIG. 3A with all colour signals reduced to 0, thereby effectively leaving signals not resulting from stain.
Figure 3C:
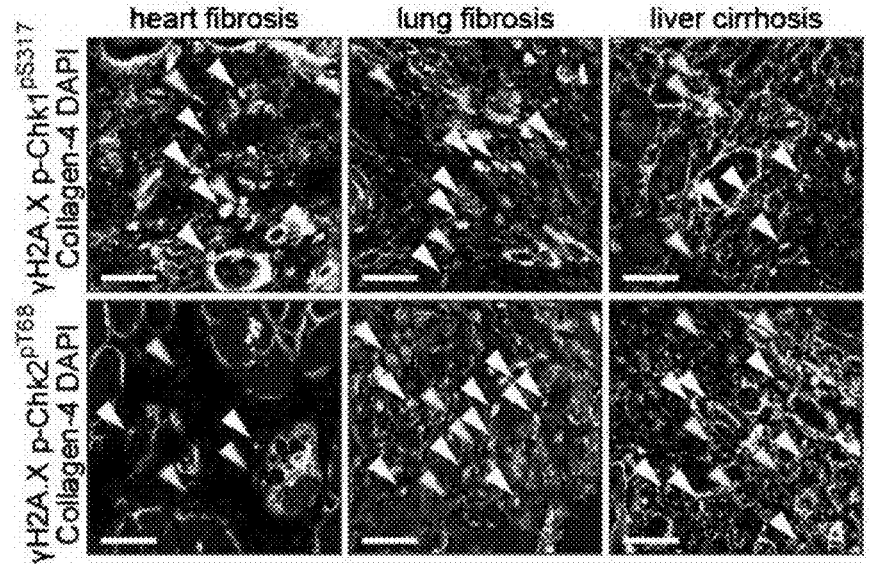
FIG. 3C shows the same photomicrographs as FIG. 3A with signals of all other colours than green reduced to 0.
Figure 3D:
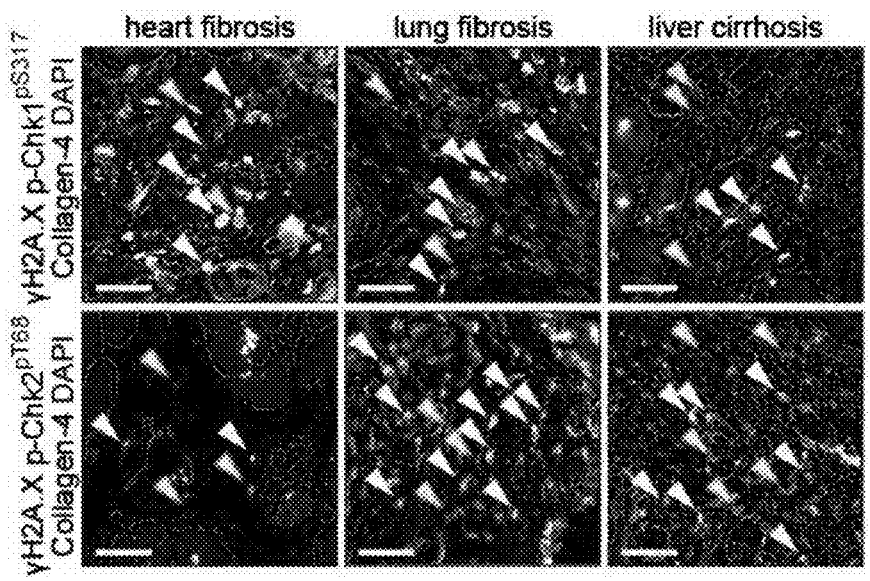
FIG. 3D shows the same photomicrographs as FIG. 3A with signals of all other colours than magenta reduced to 0.
Figure 3E:
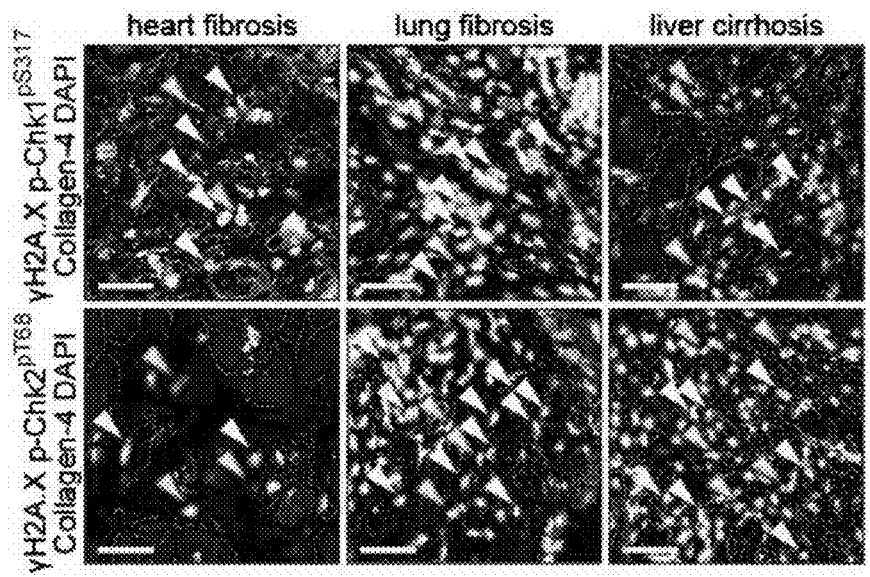
FIG. 3E shows the same photomicrographs as FIG. 3A with signals of all other colours than blue reduced to 0.
Figure 4A:
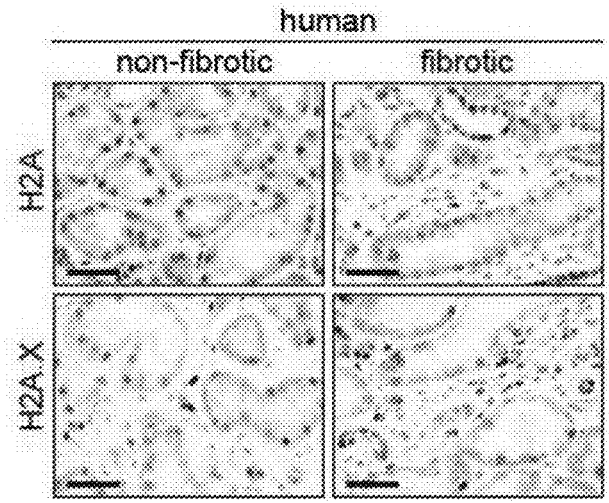
FIG. 4A shows representative photomicrographs of human kidney sections that were labelled for H2A (scale bars: 50 µm) or H2A.X (scale bars: 50 µm). The graphs in FIGS. 4B to 4G summarize the respectively labelled cells (n=3, measurements were done in 10 visual fields, data are presented as means±s.d., *p<0. p<0.01, p<0.0001, values of p were calculated using Student's t test comparing indicated groups).
Figure 5B:
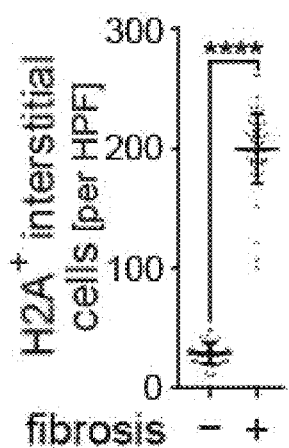
FIG. 5A shows representative photomicrographs of murine kidney sections, labelled for H2A (scale bars: 50 µm) or H2A.X (scale bars: 50 µm). The graphs in FIGS. 5B to 5G summarize the respectively labelled cells (n=3, measurements were done in 10 visual fields, data are presented as means±s.d., *p<0. p<0.01, p<0.0001, values of p were calculated using Student's t test comparing indicated groups).
FIG. 5H shows SDS-PAGE and subsequent immunoblotting of H2A.X levels in human fibroblast cultures (TK173) as compared to renal epithelial cells (HK2).
Figure 5C:
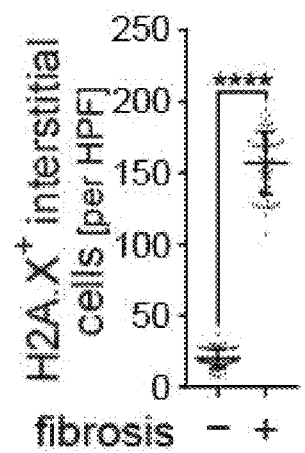
Figure 5D:
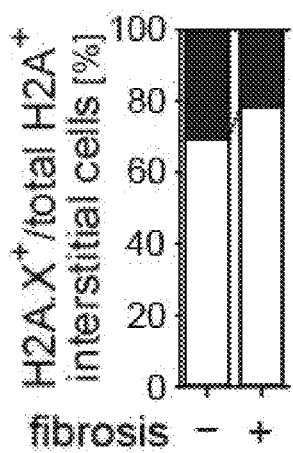
Figure 5E:
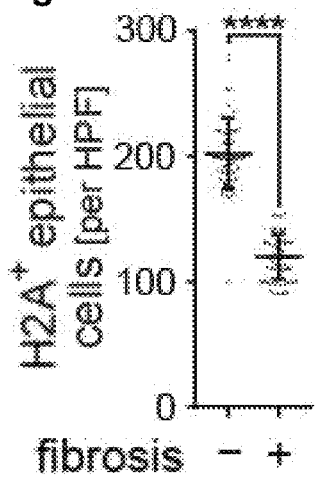
Figure 5F:
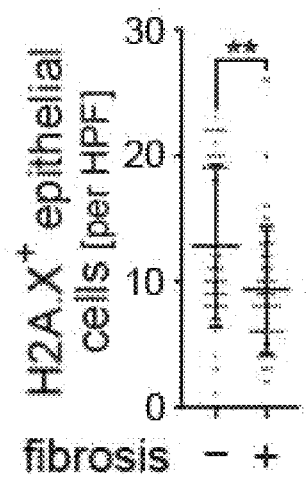
Figure 5G:
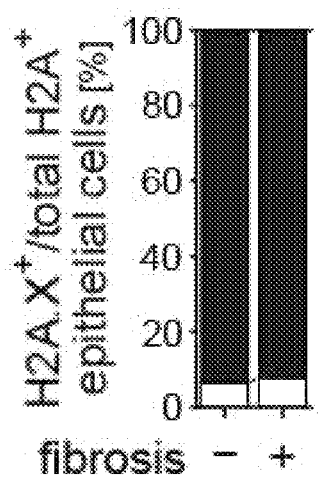
Figure 5H:
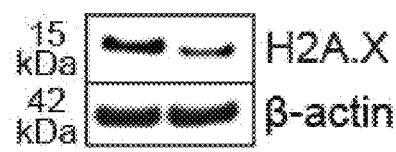
Figure 6A:
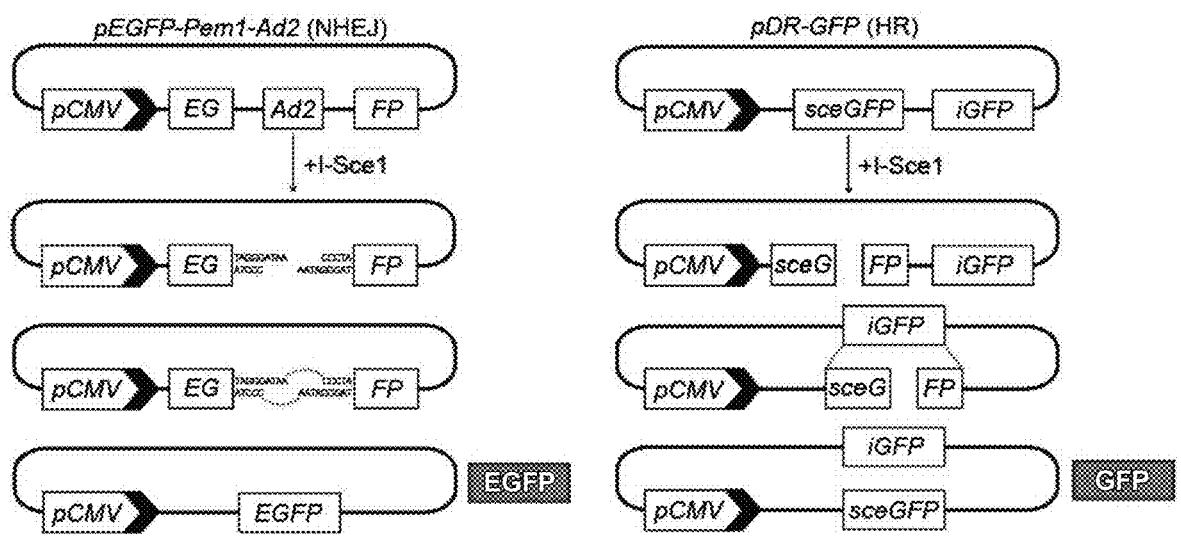
FIG. 6A depicts schematic illustrations of reporter plasmids for NHEJ in which the EGFP gene is inactivated by the presence of the Pem1 intron and an Ad2 exon flanked by I-Sce1 recognition sites (pEGFP-Pem1-Ad2) or HR harbouring I-Sce1 recognition sites within the GFP gene and inactive iGFP matrices for HR (pDR-GFP).
Figure 6B:
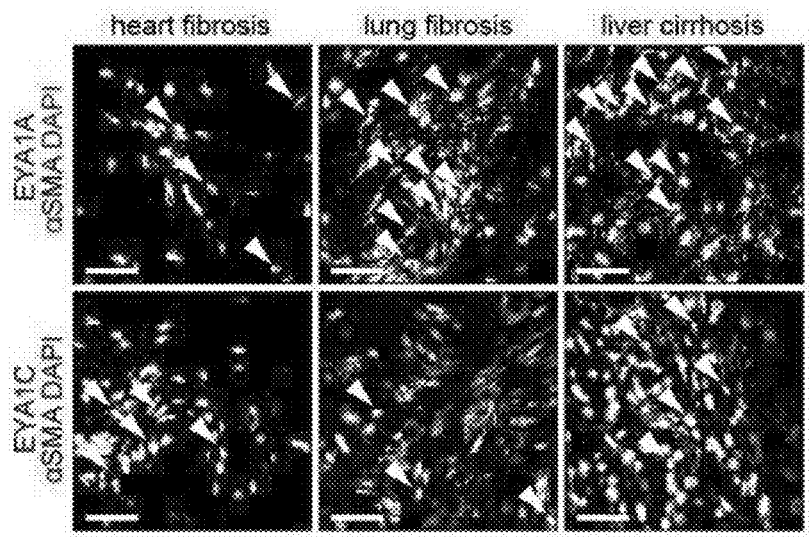
FIG. 6B shows representative immunostainings of EYA1A/αSMA (red/green scale bars: 25 µm) and EYA1C/αSMA (green/red, scale bars: 25 µm), both including DAPI nucleic acid stain (blue), within fibrotic hearts, lungs and cirrhotic livers.
Figure 6C:
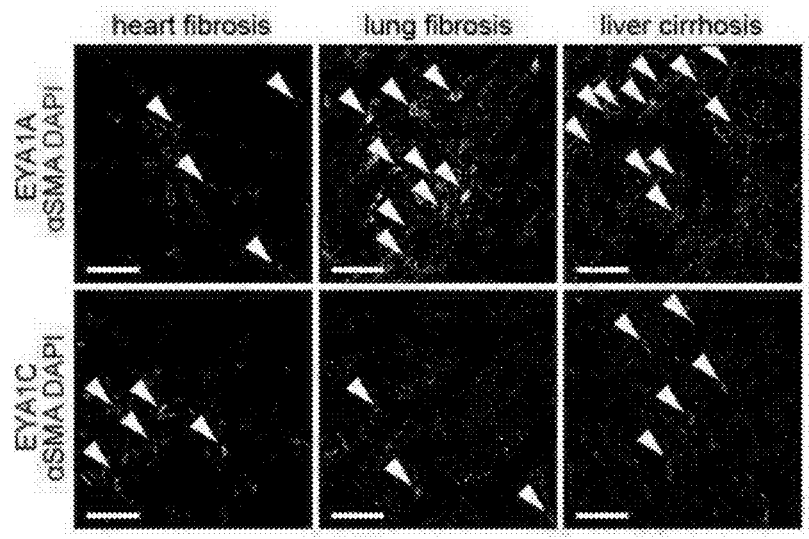
FIG. 6C shows the same photomicrographs as FIG. 6B with all colour signals reduced to 0, thereby effectively leaving signals not resulting from stain.
Figure 6D:
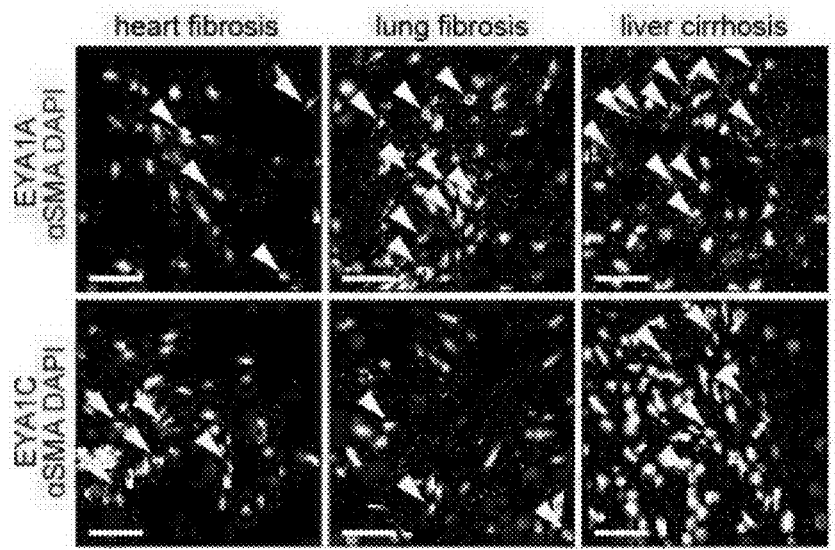
FIG. 6D shows the same photomicrographs as FIG. 6B with all other signals than signals in blue colour reduced to 0.
Figure 6E:
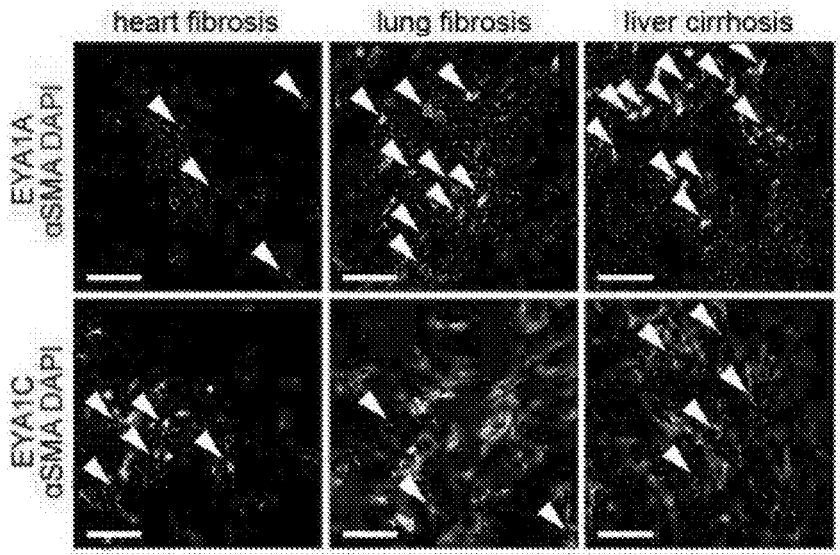
FIG. 6E shows the same photomicrographs as FIG. 6B with all other signals than signals in red colour reduced to 0.
Figure 6F:
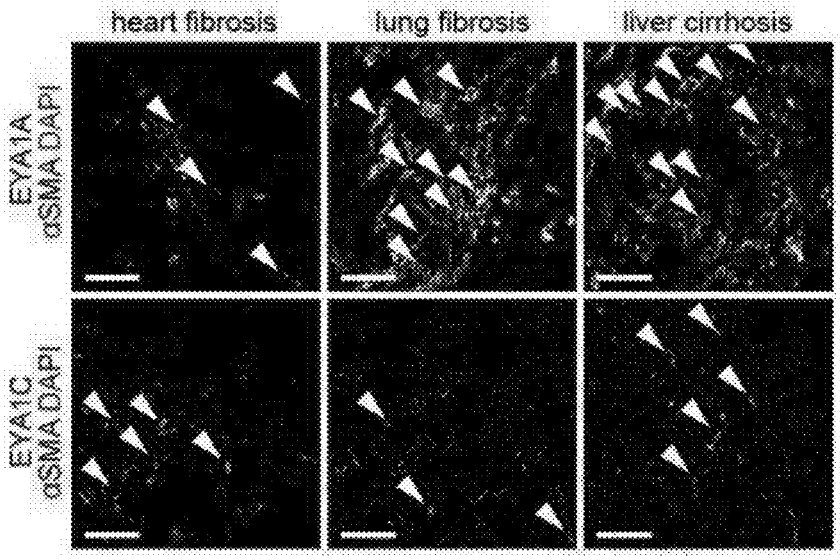
FIG. 6F shows the same photomicrographs as FIG. 6B with all other signals than signals in green colour reduced to 0.

To gain insights into distinct DDR pathways, double strand brake repair and γH2A.X dephosphorylation dynamics were compared in early passage fibroblasts under neocarcinostatin (NCS)-induced genotoxic stress (Krishnan, N, et al., J Biol Chem (2009) 284, 16066-16070). In fibroblasts isolated from fibrotic kidneys, accelerated repair of double strand brakes and γH2A.X clearance correlated with premature $\gamma H2A.X^{142}$ dephosphorylation (FIG. 2M-R), indicating utilization of modified DDR mechanisms. The two major repair mechanisms of double strand brakes in actively dividing cells are non-homologous end joining (NHEJ) and homologous recombination (HR). NHEJ repairs DSBs by direct ligation of broken ends without requiring prolonged cell cycle arrest, and NHEJ occurs during all phases of actively cycling cells. In contrast, checkpoint activation and G2/M cell cycle arrest are prequisites for HR to occur, enabling alignment of sister chromatids and strand invasion. Hence, high-fidelity NHEJ is prolific by enabling rapid repair of double strand brakes and continued cell cycle progression (Mao, Z, et al., DNA Repair (Amst) (2008) 7, 1765-1771). Fibrotic fibroblasts displayed accelerated formation of 53Bp1/γH2A.X foci (NHEJ) instead of Rpa1/γH2A.X foci (HR) (FIG. 2O, P, S, T), confirmed by substantially increased NHEJ pEGFP-Pem1-Ad2 and reduced HR pDR-GFP reporter activities (FIG. 2 U, V, and FIG. 6A) (Seluanov, A, et al., Proc Natl Acad Sci U.S.A. (2004) 101, 7624-7629; Pierce, A J, et al., Genes Dev (1999) 13, 2633-2638). Based on these observations, the inventors hypothesized that accelerated recruitment of NHEJ core proteins is a feature of rapidly dividing fibroblasts as a prerequisite of fibrotic fibroblast accumulation to occur.

Example 2—EYA1 Isoforms Determine DDR Cell Fate Decisions and CKD Progression Previous studies identified $\gamma H2A.X^{p12}$ as substrate of members of the evolutionary conserved family of eyes absent proteins. Because EYA1 was linked to renal disease progression and fibrosis in patients in two independent genome-wide screening studies (Bechtel, W. et al., Nat Med (2010) 16, 544-550; Kottgen, A. et al., BMC Med Genet (2008) 9, 49, doi:10.1186/1471-2350-9-49), the inventors explored a possible role of EYA1 in observed modified DDR mechanisms. While total EYA1 mRNA expression levels did not differ significantly between fibrotic and non-fibrotic kidneys (FIG. 7A), it was observed that fibrosis was associated with significantly increased expression of transcript variant EYA1A, whereas EYA1C levels were substantially decreased within fibrotic fibroblasts (FIGS. 7B to D, FIGS. 6B to F]). Ratio of EYA1A over EYA1C abundance within renal biopsies was associated with accelerated decline of renal function towards dialysis-dependent end-stage renal disease (ESRD, FIG. 7E), implicating that EYA1 impacts fibroblast accumulation and renal disease progression.

The inventors next aimed to elucidate whether observed EYA1 isoform switching was causally relevant for fibroblast accumulation and progression of kidney fibrosis. Because distinct EYA1 transcript variants are not present in mice (Abdelhak, S. et al., Nat Genet (1997) 15, 157-164), doxycycline (DOX)-inducible transgenic mice were generated, overexpressing human splice variants EYA1A (rtTACMV; hEYA1A-pTreTight, referred to as EYA1A$^{tg}$) or EYA1C (rtTACMV;hEYA1C-pTreTight, referred to as EYA1C) allowing assimilable overexpression of distinct EYA1 isoforms in experimental models of kidney fibrosis not affected by spontaneous phenotypes upon transgene induction (FIG. 7F).

Figure 8A:
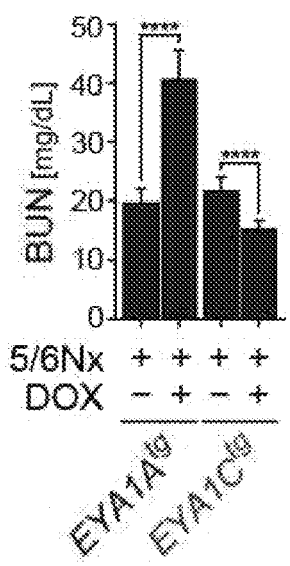
FIGS. 8A and 8B summarize average blood urea nitrogen (BUN) and plasma creatinine measurements in mice harbouring DOX-inducible transgenes for EYA1A (EYA1A$^{tg}$) or EYA1C (EYA1C$^{tg}$) 4 weeks after nephrectomy (n=10 in each group, data are presented as means±s.d., p<0.01, **p<0.0001, # no significance, values of p were calculated using Student's t test comparing indicated groups).
Figure 8B:
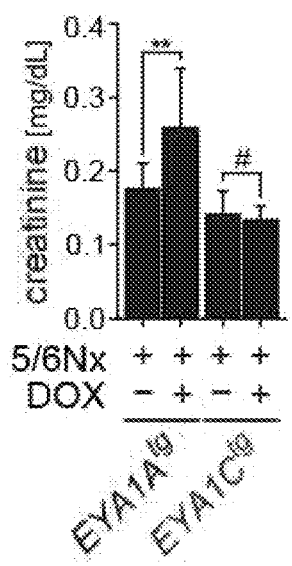
Figure 9A:
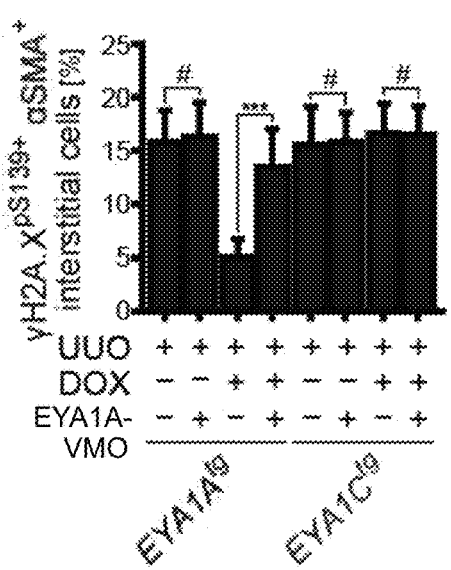
FIG. 9A depicts relative αSMA$^+$ cells positive for $\gamma H2A.X^{pY142}$ in kidney sections of wildtype mice and EYA1A^tg or EYA1C^tg mice 10 days after ureteral obstruction, treated with control or in vivo morpholinos specifically inhibiting EYA1A translation (EYA1A-VMO) (n=6 in each group, data are presented as means±s.d., p<0.01, *p<0.001, # no significance, values of p were calculated using Student's t test comparing indicated groups).
Figure 9B:
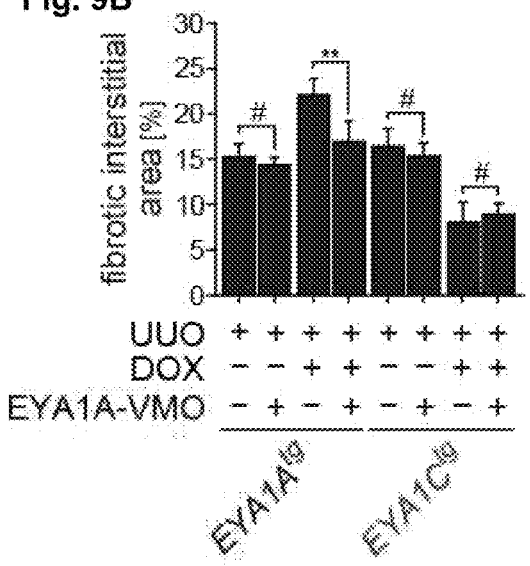
FIG. 9B depicts the relative fibrotic interstitial area.
Figure 9C:
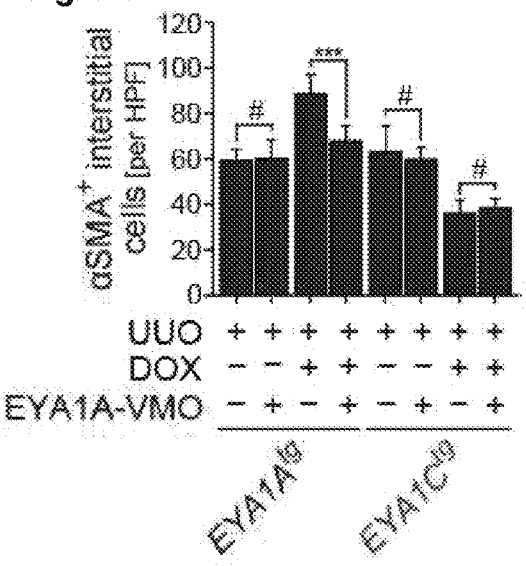
FIG. 9C depicts the average interstitial cells positive for αSMA, and FIG. 9D the relative area positive for Collagen-1 of the same cells as in FIG. 9A. Data are obtained on the basis of labelling the kidney sections for EYA1A, EYA1C, γH2A.X$^{pY142}$, αSMA, MTS, αSMA or Collagen-1.
Figure 9D:
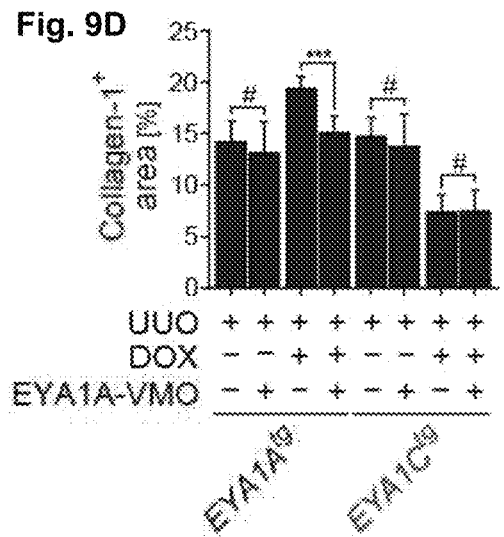

Transcriptional profiling and gene set enrichment revealed that enhanced fibrosis in EYA1A overexpressing mice was mostly related to pathways involved in DNA damage response and cell cycle checkpoint regulation (GSE92934), correlated with enhanced $\gamma$H2A.X$^{pY142}$ clearance and accumulation of NHEJ constituent 53Bp1 as compared to either uninduced transgenic mice or DOX-treated wildtype littermates (data not shown). Accelerated $\gamma$H2A.X$^{pY142}$ clearance was associated with increased fibroblast proliferation and fibrosis in kidneys of EYA1A overexpressing mice upon challenge with unilateral ureteral obstruction (UUO, FIGS. 7F to H) or 5/6 nephrectomy (5/6Nx). Increased EYA1A levels and enhanced $\gamma$H2A.X$^{pY142}$ clearance as a prerequisite of fibrotic fibroblast accumulation that we had observed within fibroblasts of human renal biopsies was associated with accelerated decline of renal excretory function (FIG. 8). Dephosphorylation assays using phosphorylated peptides for the EYA1 phosphotyrosine (ENDpYINASL) and phosphoserine phosphatase activity (RRApSVA) confirmed increased tyrosine phosphatase activity of EYA1A, correlating with enhanced interaction with $\gamma$H2A.X$^{pY142}$ (data not shown).

In control studies, administration of in vivo morpholinos to specifically inhibit transgenic EYA1A translation (EYA1A-VMO) reversed pro-fibrotic effects specifically in EYA1A overexpressing mice (FIGS. 9A to D). Transcriptional profiling and gene set enrichment revealed that enhanced fibrosis in EYA1A overexpressing mice was mostly related to pathways involved in DNA damage response and cell cycle checkpoint regulation (GSE92934, data not shown), correlated with enhanced $\gamma$H2A.X$^{pY142}$ clearance and attenuation of DNA damage checkpoint activation within fibrotic fibroblasts of chronically injured kidneys (data not shown).

Figure 10A:
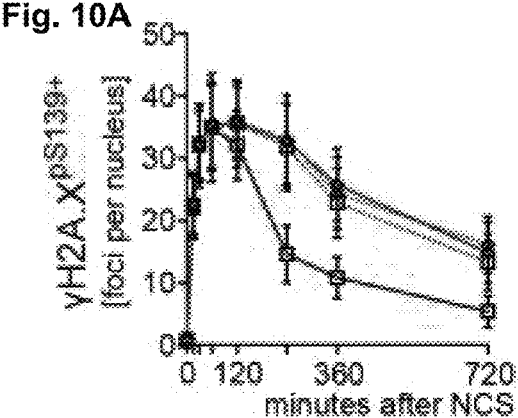
Figure 10B:
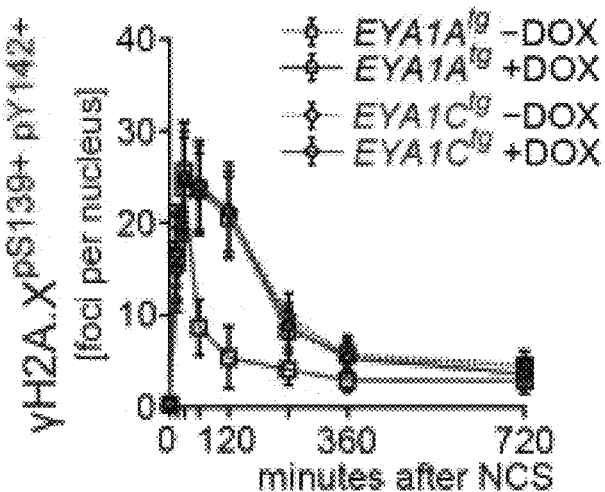
FIG. 10B depicts average foci per nucleus (n=100 nuclei, data are presented as means±s.d.) of primary murine EYA1A^tg or EYA1C^tg fibroblast cultures labelled for γH2A.X$^{pY142}$ at indicated time points after NCS exposure.
Figure 10D:
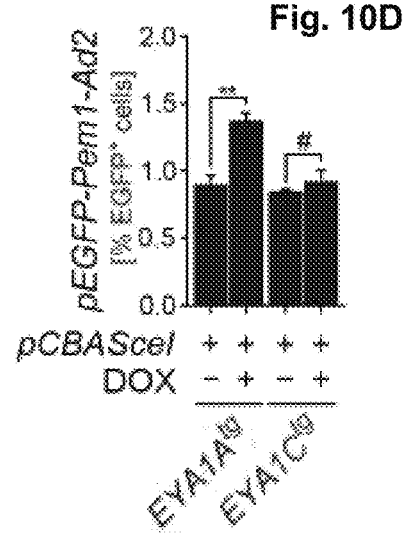
FIGS. 10D and 10E show an analysis of NHEJ and HR events upon DNA damage using pEGFP-Pem1-Ad2 (NHEJ, FIG. 10D) and pDR-GFP (HR, FIG. 10E) reporter plasmids (n=3 independent replicates, data are presented as means±s.d., p<0.01, # no significance, values of p were calculated using Student's t test comparing indicated groups).
Figure 10C:
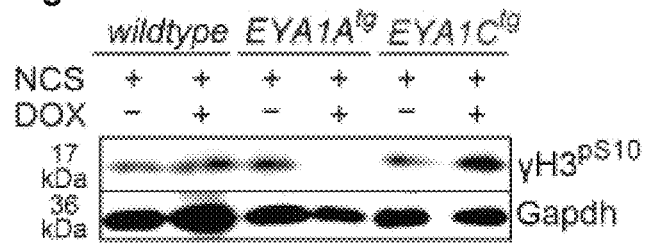
FIG. 10C depicts results of gelectrophoretic analysis, where γH3pS10 was analyzed by SDS-PAGE and subsequent immunoblotting 24 hours after NCS exposure.
Figure 10E:
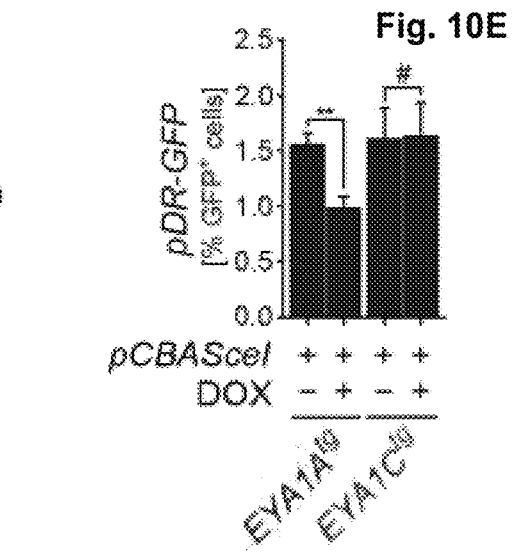
Figure 10F:
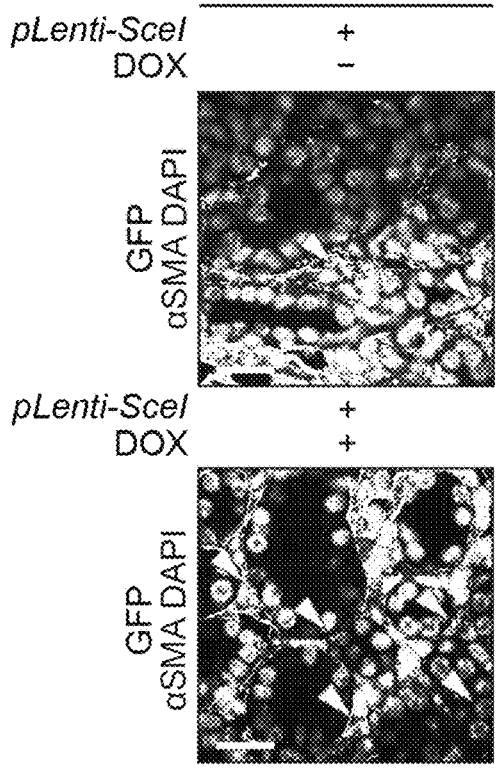
FIG. 10F shows representative photomicrographs of kidney sections labelled for GFP/αSMA (scale bars: 25 µm), as well as stained with DAPI, of transgenic EYA1A^tg mice harbouring NHEJ reporter transgenes (EYA1A^tg;R26NHEJ) were challenged with UUO and locally injected with intraparenchymal pLenti-Sce.
Figure 10G:
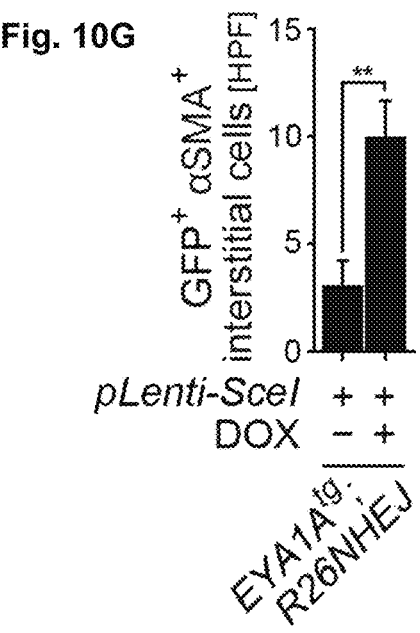
FIG. 10G summarizes average αSMA+ cells of the kidney sections described for FIG. 10F, positive for GFP, indicating NHEJ events (n=3 in each group, data are presented as means±s.d., p<0.01, values of p were calculated using Student's t test comparing indicated groups).
Figure 10H:
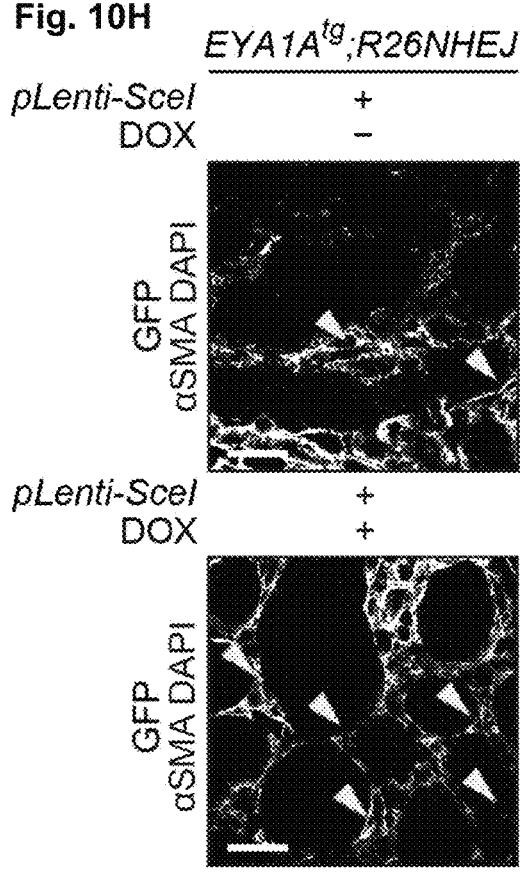
FIG. 10H shows the same photomicrographs as FIG. 10F with all colour signals reduced to 0, thereby effectively leaving signals not resulting from stain.
Figure 10I:
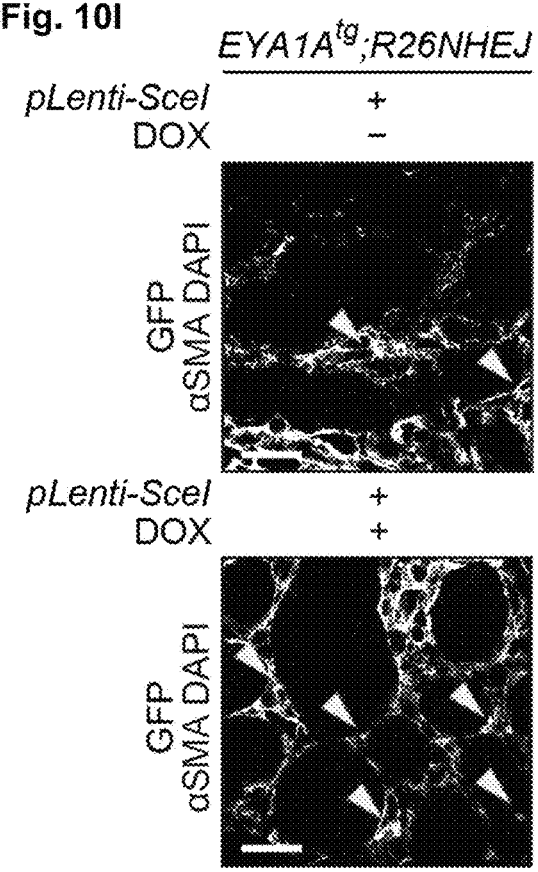
FIG. 10I shows the same photomicrographs as FIG. 10F with colour signals in blue colour reduced to 0, thus removing signals of DAPI stain.
Figure 10J:
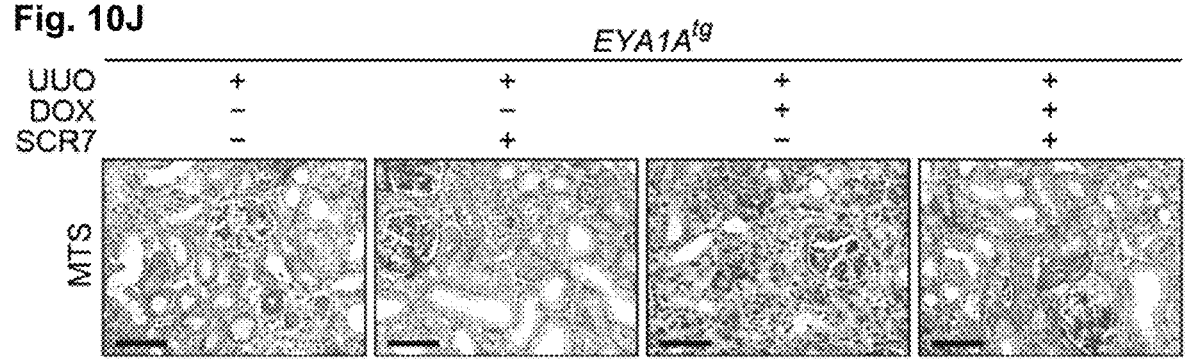
FIG. 10J shows representative photomicrographs of kidney sections of transgenic EYA1A mice challenged with UUO and treated with DNA ligase IV inhibitor SCR7 (20 mg/kg i.p. every alternate day), labelled for MTS (scale bars: 50 µm) 10 days after ureteral obstruction.
Figure 10K:
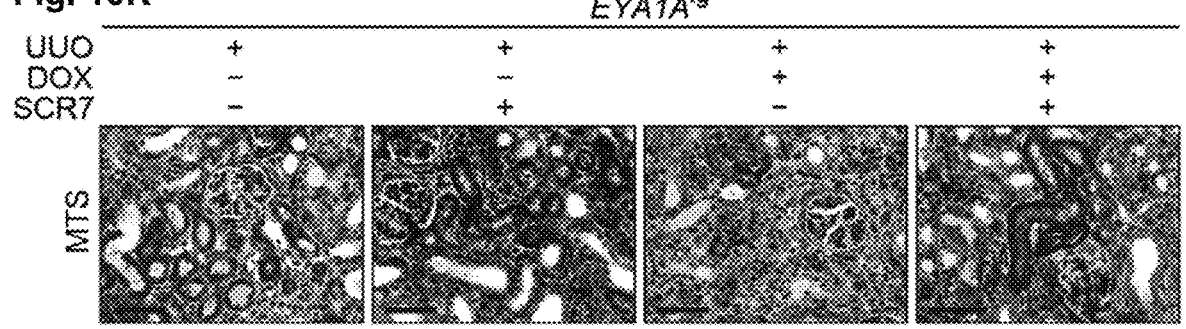
FIG. 10K shows the same photomicrographs as FIG. 10J with all colour signals reduced to 0, thereby effectively leaving signals not resulting from stain.
Figure 10L:
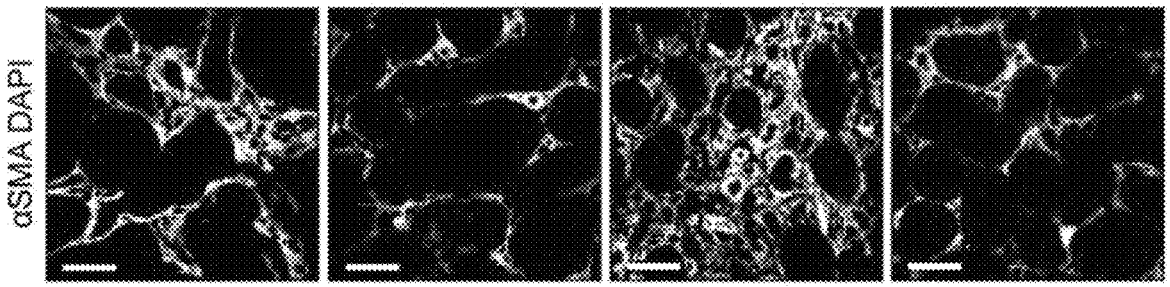
FIG. 10L shows representative photomicrographs of kidney sections of transgenic EYA1A^tg mice challenged with UUO and treated with DNA ligase IV inhibitor SCR7 (20 mg/kg i.p. every alternate day), labelled for αSMA (scale bars: 50 µm) 10 days after ureteral obstruction.
Figure 10M:
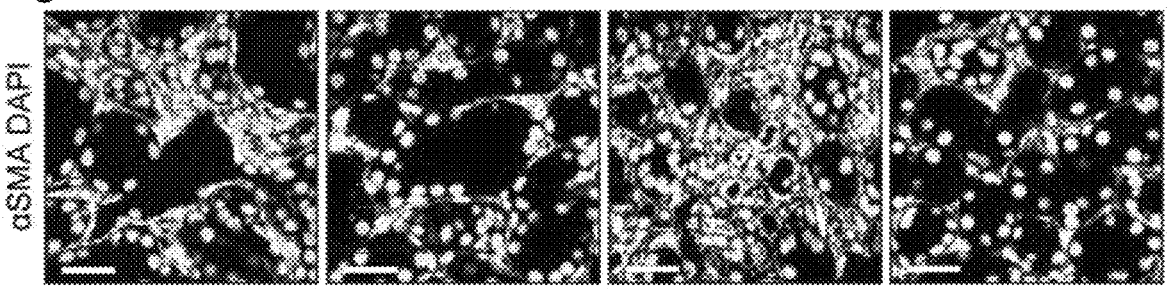
FIG. 10M shows the same photomicrographs as FIG. 10L with DAPI signals, which were removed in FIG. 10L by reducing blue colour signals to 0.
Figure 10N:
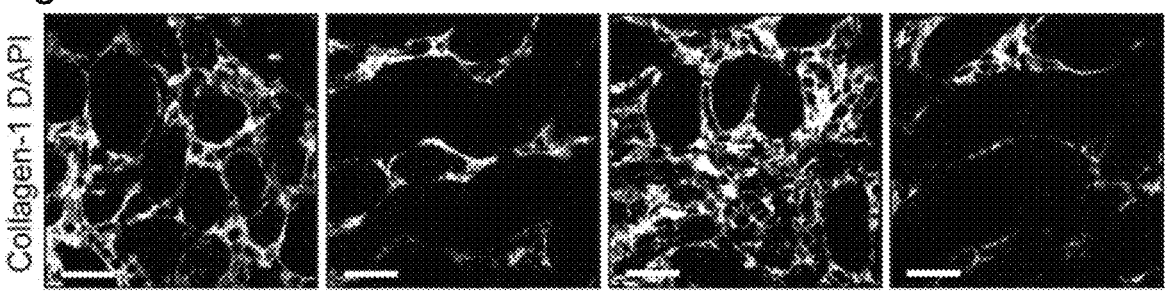
FIG. 10N shows representative photomicrographs of kidney sections of transgenic EYA1A^tg mice challenged with UUO and treated with DNA ligase IV inhibitor SCR7 (20 mg/kg i.p. every alternate day), labelled for Collagen-1 (scale bars: 50 µm) 10 days after ureteral obstruction.
Figure 10O:
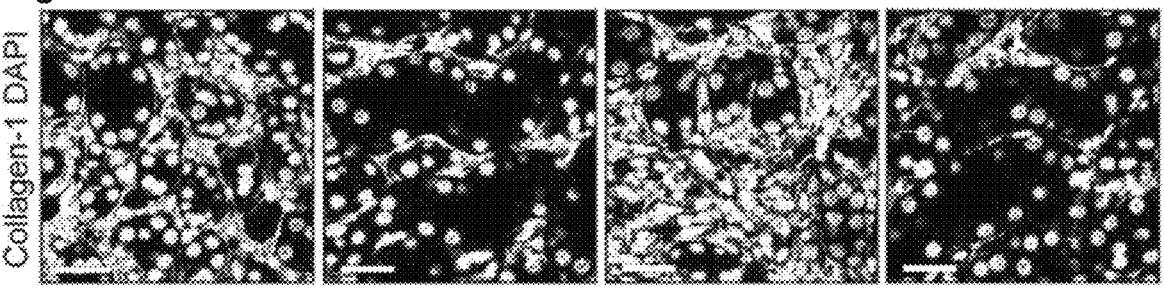
FIG. 10O shows the same photomicrographs as FIG. 10L with DAPI signals, which were removed in FIG. 10L by reducing blue colour signals to 0.
Figure 10P:
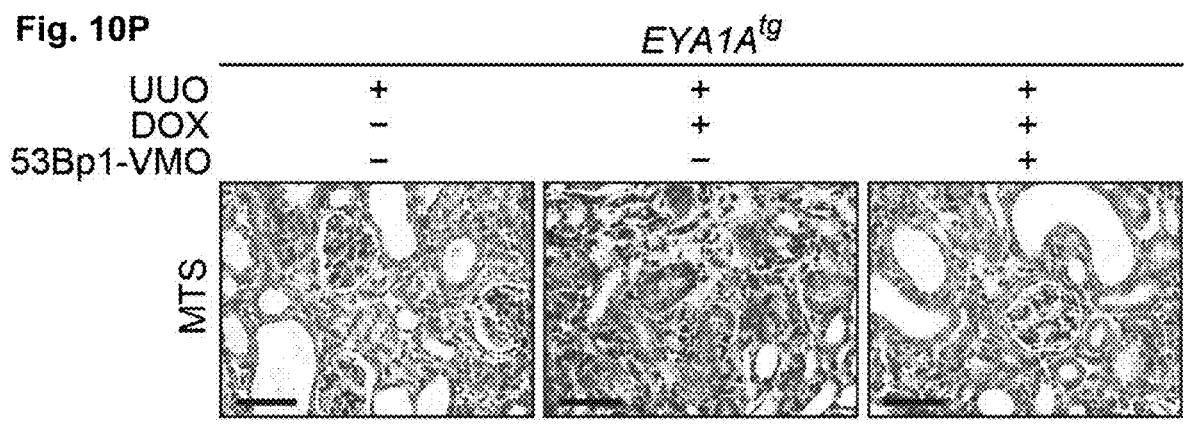
FIG. 10P shows representative photomicrographs of kidney sections of transgenic EYA1A mice challenged with UUO and treated with in vivo morpholinos blocking 53Bp1 translation (53Bp1-VMO), labelled for MTS (scale bars: 50 µm) 10 days after ureteral obstruction.
Figure 10Q:
FIG. 10Q shows the same photomicrographs as FIG. 10L with all colour signals reduced to 0, thereby effectively leaving signals not resulting from stain.
Figure 10R:
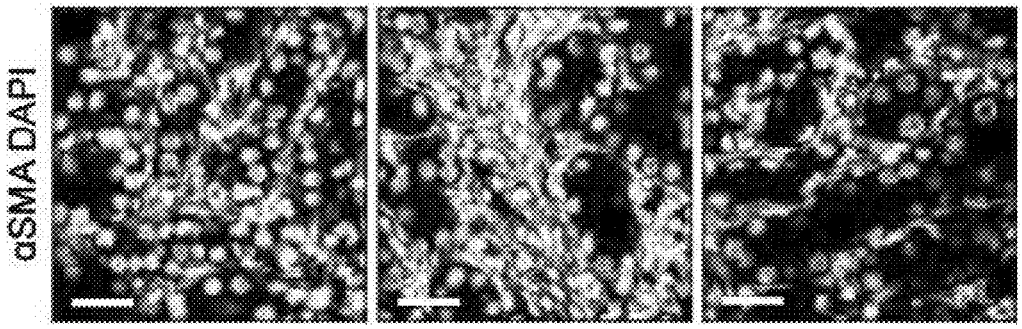
FIG. 10R shows representative photomicrographs of kidney sections of transgenic EYA1A mice challenged with UUO and treated with in vivo morpholinos blocking 53Bp1 translation (53Bp1-VMO), labelled for alpha-smooth muscle actin (αSMA) (scale bars: 50 µm) 10 days after ureteral obstruction, and stained with DAPI.
Figure 10S:
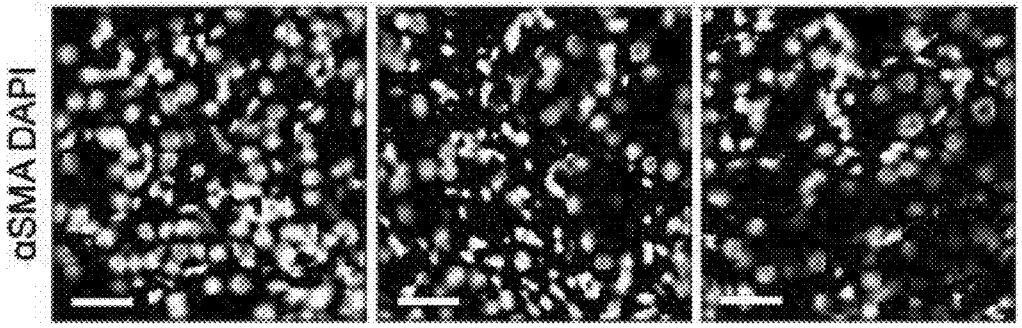
FIG. 10S shows the same photomicrographs as FIG. 10R with red colour signals reduced to 0, thereby effectively leaving signals not resulting from stain and DAPI stain.
Figure 10T:
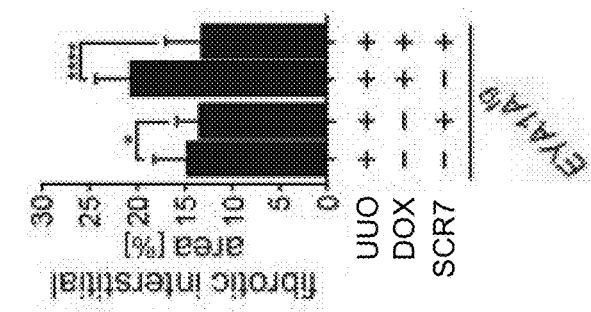

Reduced checkpoint activation within renal fibroblasts correlated with accumulation of 53Bp1 and Xrcc4 (NHEJ constituents) instead of Rpa1 and Rad51 recombinase (HR constituents), phenocopying the association of increased EYA1A levels, enhanced $\gamma$H2A.X$^{pY142}$ clearance, attenuated DNA damage checkpoint activation and predominant recruitment of NHEJ core proteins that the inventors had observed within fibroblasts of human renal biopsies. In synchronized renal transgenic fibroblasts, EYA1A overexpression induced premature $\gamma$H2A.X$^{pY142}$ dephosphorylation and clearance of DSBs (FIGS. 10A and B) and increased re-entry into cell cycle (as indicated by attenuated $\gamma$H3$^{pS10}$, FIG. 10C). In line with the inventors' previous findings, premature $\gamma$H2A.X$^{pY142}$ dephosphorylation was found to be associated with accelerated recruitment of high-fidelity NHEJ core proteins and NHEJ pEGFP-Pem1-Ad2 reporter activity (FIGS. 10D and E). These observations were confirmed in kidneys of EYA1A overexpressing mice harbouring NHEJ reporter transgenes (EYA1A$^{tg}$; R26NHEJ, FIGS. 10 G to I) (Vaidya A., et al., PLoS Genet (2014) 10, e1004511), providing further evidence that high-fidelity NHEJ becomes the predominant repair pathway when EYA1A was increased.

To elucidate causality between the observed EYA1A-induced shift towards NHEJ, enhanced fibroblast accumulation and fibrosis, the inventors next administered the small molecule NHEJ inhibitor SCR7 to EYA1A$^{tg}$ mice challenged with UUO (Srivastava M., et al., Cell (2012) 151, 1474-1487). SCR7 (20 mg/kg i.p. every alternate day) significantly reduced fibrosis and fibroblast accumulation in EYA1A overexpressing mice (FIGS. 10 J to O, T, V and W), further supporting that high-fidelity NHEJ becomes the predominant repair pathway specifically in EYA1A overexpressing mice.

Because the inventors had observed robust 53Bp1/$\gamma$H2A.X foci formation and 53Bp1 accumulation upon EYA1A overexpression in fibroblast cultures and chronically injured kidneys, we next administered in vivo morpholinos blocking 53Bp1 translation (53Bp1-VMO) to EYA1Atg mice challenged with UUO. Rationale for this approach was that previous studies had established 53Bp1 as direct suppressor of HR, that depletion of 53Bp1 is capable to shift the cell fate decision from NHEJ to HR (Zimmermann M., et al., Science (2013) 339, 700-704; Bunting S.F., et al., Cell (2010) 141, 243-254). Depletion of 53Bp1 within chronically injured kidneys upon 53Bp1-VMO administration correlated with increased presence of Rpa1 in EYA1A-overexpressing mice (indicative of increased HR, FIGS. 10 R, S, X and Y). Reversal of EYA1A-induced NHEJ cell fate decision attenuated fibroblast accumulation and renal fibrosis (FIGS. 10 P to S, Z, and Z1), reversing the effect of EYA1A overexpression and suggesting that NHEJ causally contributes to fibrosis and fibroblast accumulation.

In contrast to established mechanistic link between EYA1A and high-fidelity NHEJ, overexpression of EYA1C in EYA1C$^{tg}$ mice attenuated fibrosis in both models and reduced fibroblast accumulation independent of DNA damage checkpoint activation or DDR cell fate decisions (FIGS. 7F and G, 8A and B, 10A and B), suggesting that EYA1A and EYA1C possess distinct biological activities and prompting us to further explore underlying mechanisms.

Figure 11B:
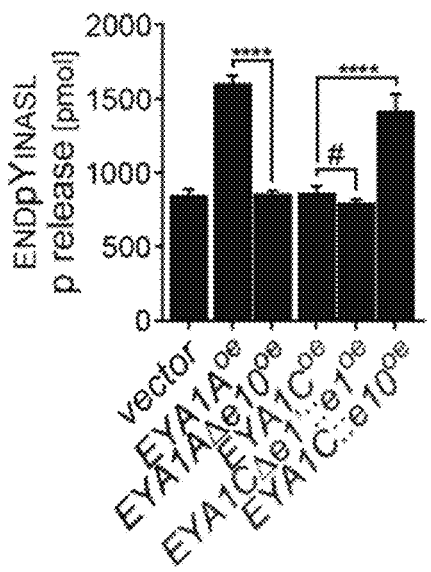
FIG. 11B depicts data on the dephosphorylation activity using phosphotyrosine substrate ENDpYINASL (n=3 independent replicates, data are presented as means±s.d., **p<0.0001, # no significance, values of p were calculated using one-way ANOVA with Bonferroni post-hoc analysis comparing indicated groups).

Example 3—Inclusion of Critical Exon 10 Determines EYA1 Tyrosine Phosphatase Activity Based on their findings, the inventors hypothesized that EYA1 splicing in humans could serve as means to realize distinct phosphatase substrate specificities. Because the two major differences between EYA1 isoforms EYA1A and EYA1C are the use of alternate exons 11' and distinct inclusion/skipping of exon 10 (FIG. 11A) (Abdelhak et al. 1997, supra), they asked if alternative splicing of either of the two regions could alter EYA1 substrate specificities. To explore the causal contribution of alternate exon 11' and exon 10 for the observed distinct serine and tyrosine phosphatase activities, they overexpressed mutant EYA1A in which exon 10 had been removed (EYA1$\Delta$e10), mutant EYA1C where exon 1' was replaced with exon 1 (EYA1C$\Delta$1'::e1) or EYA1C to which exon 10 had been added (EYA1C::e10) (FIG. 11A).

Figure 11C:
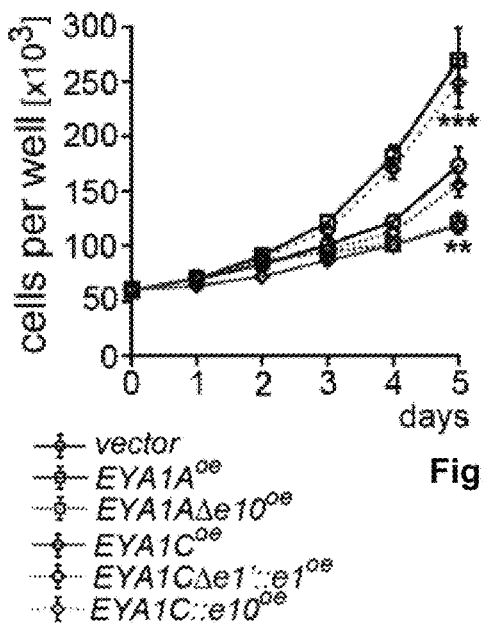
FIG. 11C depicts data on the effect on fibroblast proliferation activity. Primary murine fibroblasts transfected with indicated constructs were seeded at a density of 60,000 per well and proliferative activity was determined at indicated time points (n=3 independent replicates, data are presented as means±s.d., p<0.01, ***p<0.001, values of p were calculated using one-way ANOVA with Bonferroni post-hoc analysis comparing EYA1A and EYA1AΔe10 or EYA1C and EYA1C::e10). Noteworthy, data correlate with data shown in FIG. 11B.
Figure 11D:
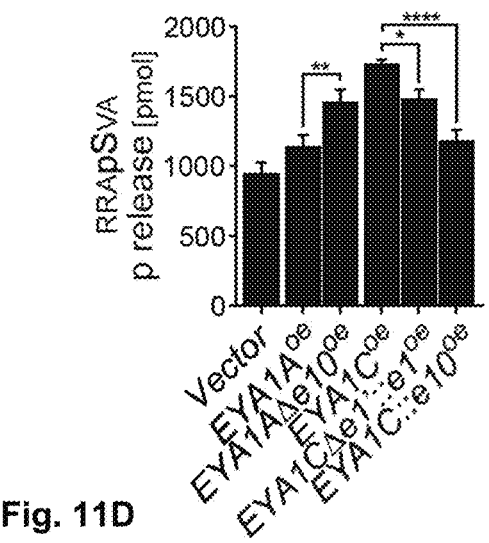
FIG. 11D depicts data on the dephosphorylation activity using phosphoserine substrate RRApSVA (n=3 independent replicates, data are presented as means±s.d., *p<0.05, p<0.01, **p<0.0001, values of p were calculated using one-way ANOVA with Bonferroni post-hoc analysis comparing indicated groups).
Figure 11E:
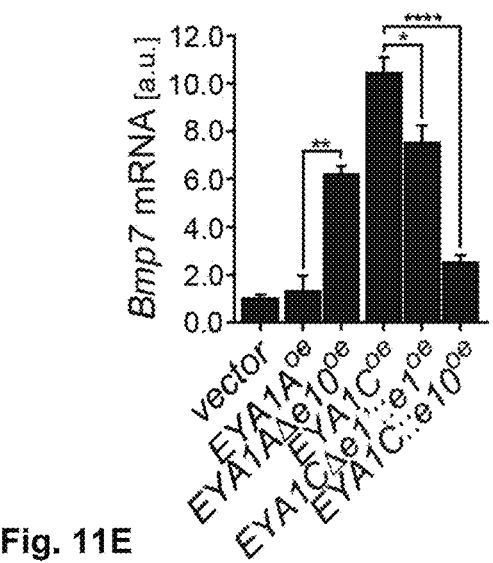
FIG. 11A is a schematic illustration of EYA1A and EYA1C mutant constructs with EYA1A in which exon 10 has been removed (EYA1AΔe10), mutant EYA1C where exon 1' has been replaced with exon 1 (EYA1CΔ1'::e1) or EYA1C to which exon 10 has been added (EYA1C::e10).
FIGS. 11F to 11I show results of an analysis of photomicrographs of primary murine fibroblast cultures transfected with control plasmids (vector) or plasmids overexpressing EYA1 mutant mice harbouring DOX-inducible transgenes. The legend depicted next to FIG. 11F applies to all figures of FIGS. 11F to 11I. Cells were labelled for $\gamma H2A.X^{pS139}$ (FIG. 11F), $\gamma H2A.X^{pY142}$ (FIG. 11G), $\gamma H2A.X^{pS139}$/53Bp1 (FIG. 11H) and $\gamma H2A.X^{pS139}$/Rpa1 (FIG. 11) at indicated time points after NCS exposure. Average foci per nucleus are shown (n=100 each, data are presented as means±s.d.).
FIGS. 11J and 11K depict results of an analysis of NHEJ and HR events upon DNA damage using pEGFP-Pem1-Ad2 (NHEJ, FIG. 11J) and pDR-GFP (HR, FIG. 11K) reporter plasmids. Data are presented as means±s.d. (*p<0.05, **p<0.01, # no significance, values of p were calculated using Student's t test comparing indicated groups).
Figure 11F:
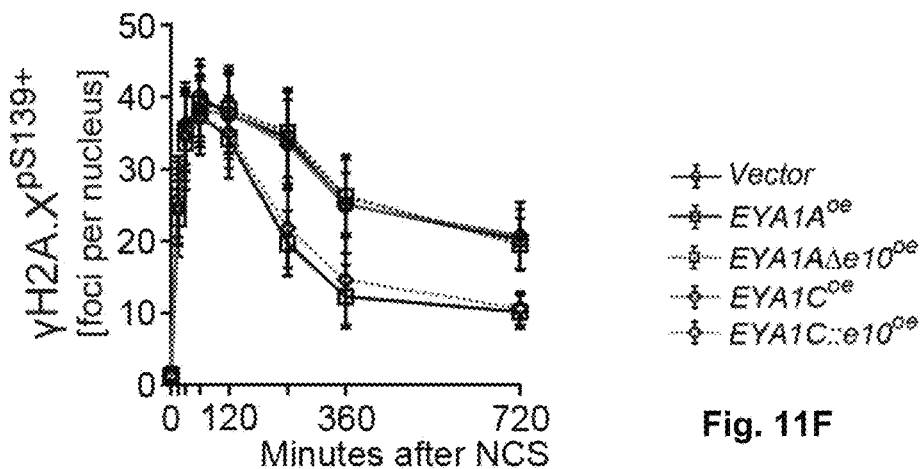
Figure 11G:
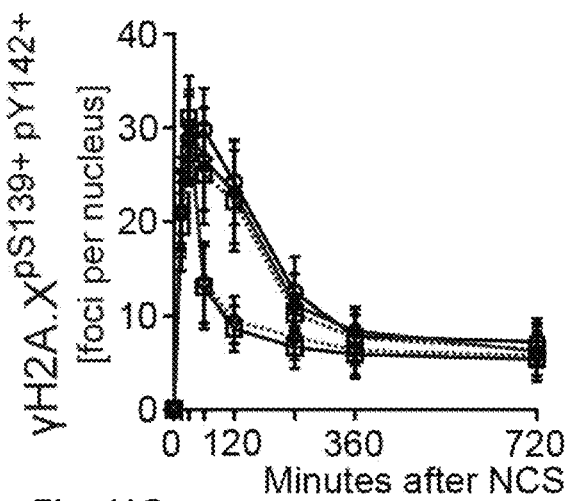
Figure 11H:
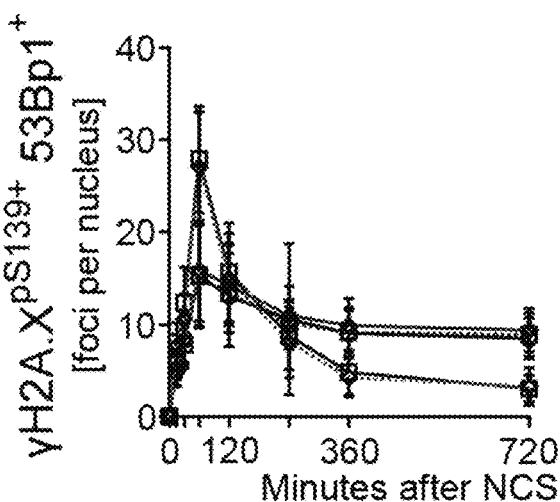
Figure 11I:
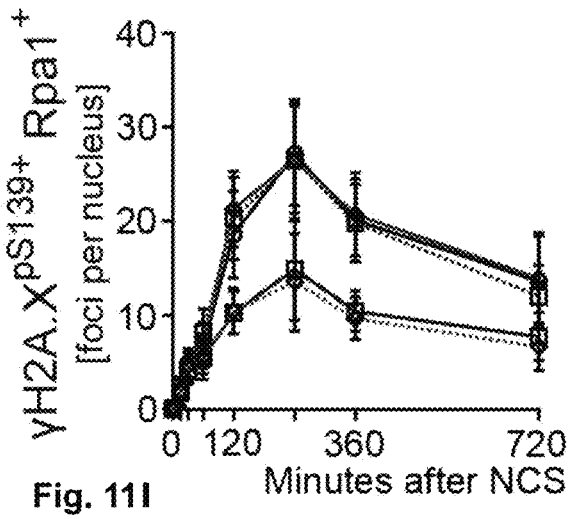
Figure 11J:
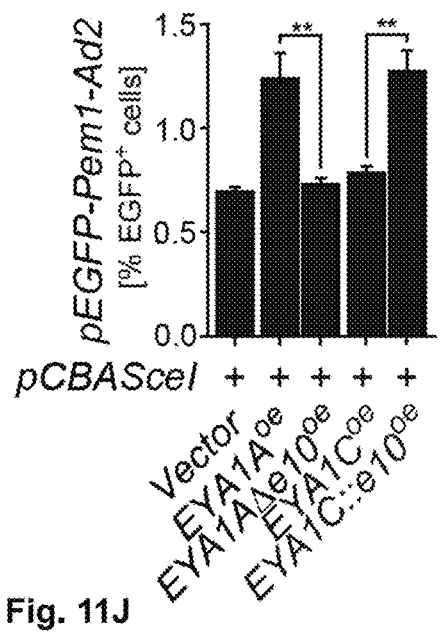
Figure 11K:
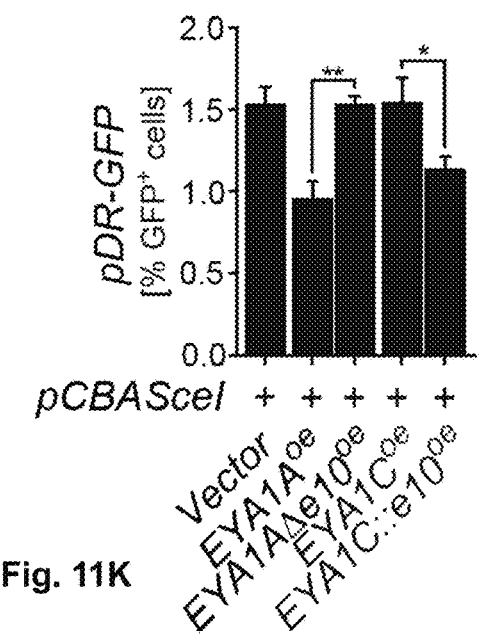

When exon 10 was absent (EYA1C and EYA1$\Delta$e10), activity to dephosphorylate peptides encoding for the EYA1 phosphatase histone substrate motif ENDpYINASL were reduced (FIG. 11B), correlating with failure to accelerate fibroblast proliferation (FIG. 11C). Instead, dephosphorylation assays using the synthetic serine phosphatase substrate RRApSVA demonstrated superior serine phosphatase activity (FIG. 11D). In contrast, overexpression of EYA1C::e10 phenocopied dephosphorylating efficacy and fibroblast accumulation of EYA1A (FIG. 11B,C), suggesting that EYA1 tyrosine phosphatase activity depends on the absence/presence of alternative spliced exon 10. EYA1C containing exon 10 (EYA1C::e10) phenocopied EYA1A with regard to premature $\gamma$H2A.X$^{pY142}$ dephosphorylation, $\gamma$H2A.X clearance and accelerated recruitment of NHEJ (FIGS. 11F to 11I). In contrast, deletion of EYA1A critical exon 10 (EYA1$\Delta$e1) normalized premature $\gamma$H2A.X$^{pY142}$ dephosphorylation and γH2A.X clearance, associated with accelerated HR (FIGS. 11F to 11I). Inclusion of exon 10 to EYA1C enhanced NHEJ, whereas deletion of exon 10 from EYA1A increased HR responses in previous established reporters (FIGS. 11J and K) (Seluanov A., et al., Proc Natl Acad Sci USA (2004) 101, 7624-7629; Pierce A. J., Genes Dev (1999) 13, 2633-2638).

To elucidate if pro-fibrotic activity of EYA1A (exon 10 included) was specifically due to its increased tyrosine phosphatase activity, we next utilized established EYA1 γH2A.X$^{pY142}$ tyrosine phosphatase inhibitors Na$_3$VO$_4$ (blocking tyrosine phosphatase activity) and caffeine (blocking ATM-dependent recruitment of EYA1 towards γH2A.X) (Cook P. J., et al., Nature (2009) 458, 591-596; Rayapureddi, J. P., et al., Nature (2003) 426, 295-298). Either Na$_3$VO$_4$ or caffeine reversed EYA1A-induced premature γH2A.X$^{pY142}$ dephosphorylation and fibroblast accumulation, whereas neither Na$_3$VO$_4$ nor caffeine affected γH2A.X$^{pY142}$ in EYA1C overexpressing cells (FIGS. 12A and B).

Figure 13:
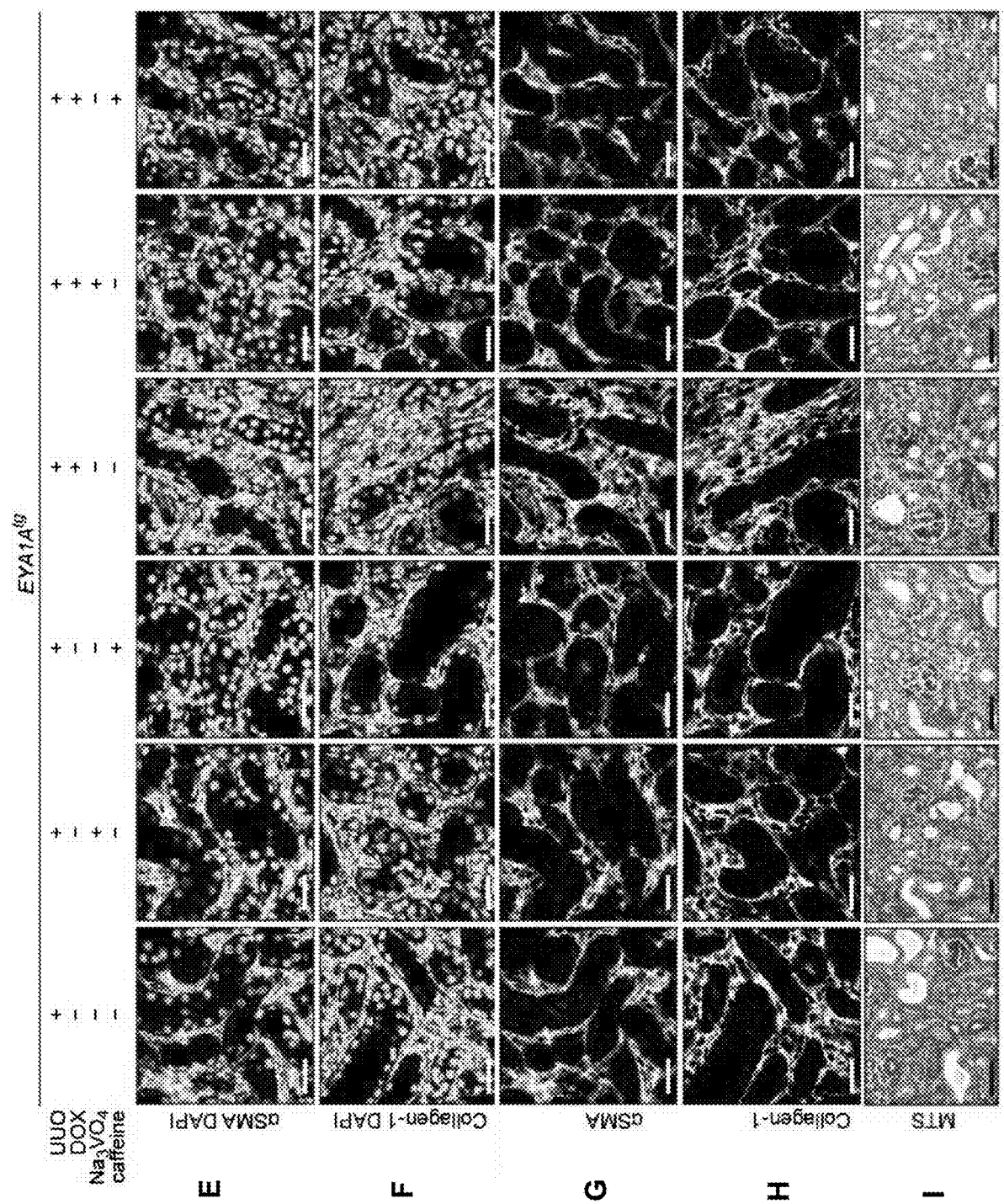
FIGS. 13A-13I illustrate a modulation of the impact of EYA1A overexpression on renal fibrogenesis using $Na_3VO_4$ and caffeine, which effectively blocked $\gamma H2A.X^{pY142}$ dephosphorylation. Transgenic EYA1A$^{tg}$ mice were challenged with UUO and treated with either $Na_3VO_4$ (8 mg/kg i.p. once per day) or caffeine (12.5 mg/kg i.p. once per day). The graphs in FIGS. 13A to 13D summarize an analysis of photomicrographs of kidney sections labelled for $\gamma H2A.X^{pY142}$ and αSMA, αSMA, or collagen-1.

To gain insights into a possible mechanistic connection between previously observed γH2A.X clearance and γH2A.X$^{pY142}$ dephosphorylation in EYA1A overexpressing mice, we next administered predetermined doses of Na$_3$VO$_4$ (8 mg/kg i.p. once per day) or caffeine (12.5 mg/kg i.p. once per day) to EYA1Atg mice challenged with UUO (Rayapureddi et al., 2003, supra; Ostrowski J., et al., J Hepatol (2000) 32, 965-974; Barone L. M., et al., J Cell Biochem (1993) 52, 171-182). Na$_3$VO$_4$ and caffeine effectively blocked γH2A.X$^{pY142}$ dephosphorylation and reversed the enhancing impact of EYA1A overexpression on renal fibrogenesis (FIGS. 13 A to D), further supporting that the pro-fibrotic effect of EYA1A is dependent on its tyrosine phosphatase activity, and demonstrating that this effect can be pharmacologically targeted by inhibition of its tyrosine phosphatase activity.

Because inhibition of tyrosine phosphatase activity by Na$_3$VO$_4$ or caffeine is not limited to EYA1, the inventors next screened for additional compounds for selective modulation of EYA1A phosphatase activity. Among 736 compounds contained in the NCI mechanistic set, they identified 228 inhibitors of EYA1A phosphatase activity (FIG. 14).

Figure 15F:
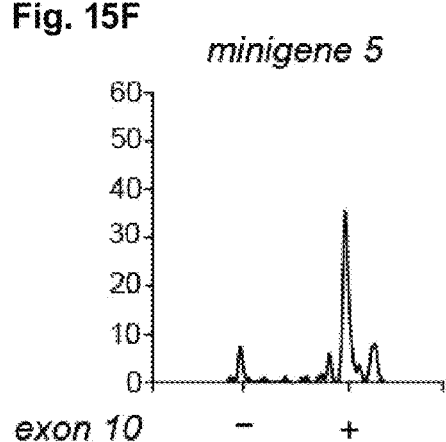
FIG. 15F depicts Bioanalyzer fluorescent units for an analysis of PCR products using minigene 3-specific oligonucleotides.
Figure 15G:
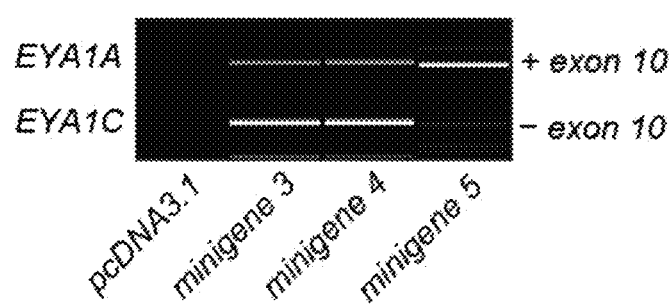
FIG. 15G depicts a virtual gel image of PCR products using the minigene-specific oligonucleotides corresponding to FIGS. 15D to 15F.
Figure 15H:
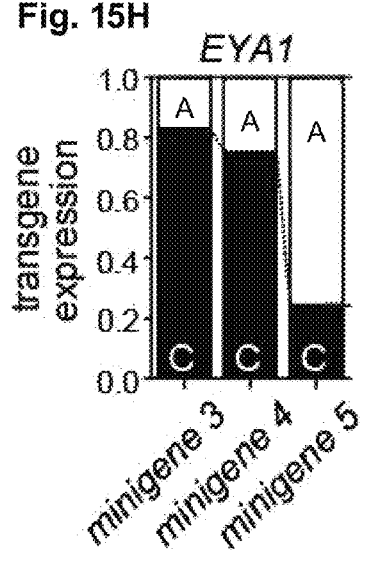
FIG. 15H shows the transient expression of EYA1 isoforms using minigenes 3, 4 and 5.

Example 4—Intronic SNP rs13259388 Affects EYA1 Exon 10 Splicing and Disease Progression in Humans The inventors next aimed to gain insights into the mechanisms underlying unfavourable EYA1 isoform by generating minigenes harbouring exons 1-10 and intronic fragments flanking exon 10 containing cis regulatory elements (-1165 relative to intron 9-10/exon 10 junction, FIG. 15C). Using intron 9-10 deletion mutants, we identified a critical role of intronic region -920 bp to -634 bp (FIGS. 15D to H).

Figure 16B:
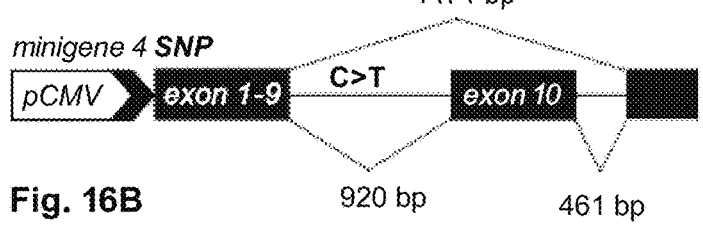
FIG. 16B is a schematic illustration of minigene 4 SNP, containing a C>T point mutation at −893 bp (mirroring SNP rs3259388).
Figure 16C:
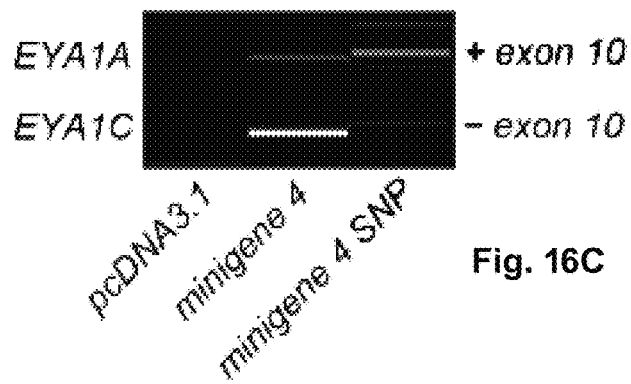
FIG. 16C depicts a virtual Bioanalyzer gel image of PCR products obtained from renal fibroblasts transfected with minigene 4 harbouring the wildtype "C" allele and minigene 4 SNP.
Figure 16A:
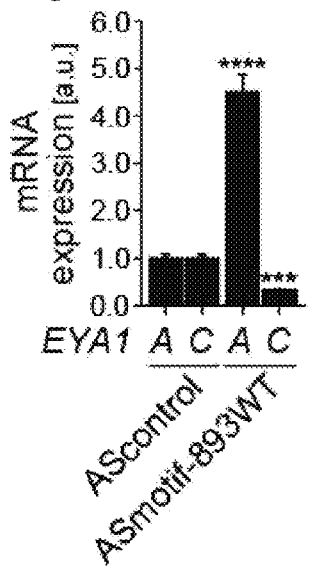
FIG. 16A shows the analysis by qRT-PCR of the effect of administering morpholinos to block splicing cis regulatory motif (ASmotif-893WT) in TK173 fibroblast cultures. EYA1A mRNA expression was enhanced, while EYA1C mRNA expression was reduced (n=3 independent replicates, data are presented as means±s.d., *p<0.001, **p<0.0001, values of p were calculated using Student's t test comparing ASmotif-893WT with AScontrol cultures)
Figure 16D:
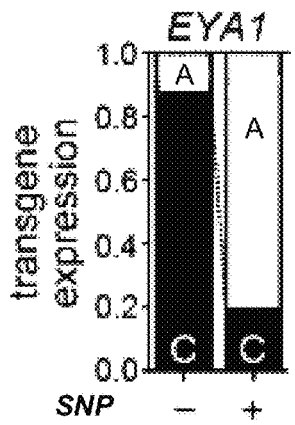
FIG. 16D depicts the transient expression of EYA1 isoforms from renal fibroblasts transfected with minigene 4 and minigene 4 SNP, corresponding to FIG. 16C. Fibroblasts transfected with minigene 4 displayed exon 10 skipping, whereas exon 10 was retained when the mutated minigene 4 SNP containing the "T" allele was used.

Because the intronic region upstream EYA1 exon 10 contains a predicted splicing cis regulatory motif (FIG. 15C) (Akerman M., et al., Genome Biol (2009) 10, R30; Paz I., et al., Nucleic Acids Res (2010) 38, W281-285), we administered morpholinos to block aforementioned splicing cis regulatory motif (ASmotif-893WT) and observed enhanced EYA1 exon 10 inclusion (FIG. 16A), indicating that identified motif plays an important role in EYA1 exon 10 splicing. Because this motif is disrupted by a common single nucleotide polymorphism at -893 bp (SNP rs3259388 C>T: ccggtgtgC/Tattttatg, FIGS. 15A and B) with minor allelic frequency for "T" of 0.2242 in the 1000Genome phase 1 population with possibly broad clinical implication (C. Genomes Project et al., Nature (2012) 491, 56-65), we hypothesized that this polymorphism could affect EYA1 exon 10 splicing. To test this hypothesis, we next analyzed impact of a C>T point mutation at -893 bp (minigene 4 SNP, mirroring SNP rs3259388, FIG. 16B) on EYA1 exon 10 skipping and inclusion in renal fibroblasts. While renal fibroblasts transfected with minigene 4 harboring the wild-type "C" allele displayed exon 10 skipping, exon 10 was retained when the mutated minigene 4 SNP containing the "T" allele was used (FIGS. 16C and D).

Figure 16E:
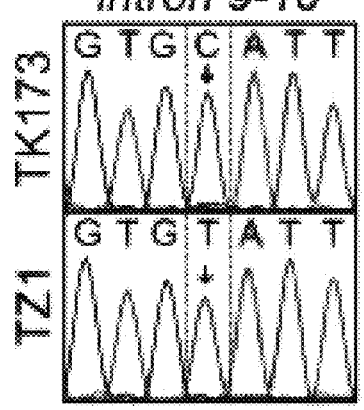
FIG. 16E depicts a sequencing chromatogram of fibroblast cultures established from patients homozygous for the wildtype "C" allele (TK173) or SNP rs13259388 "T"
Figure 16F:
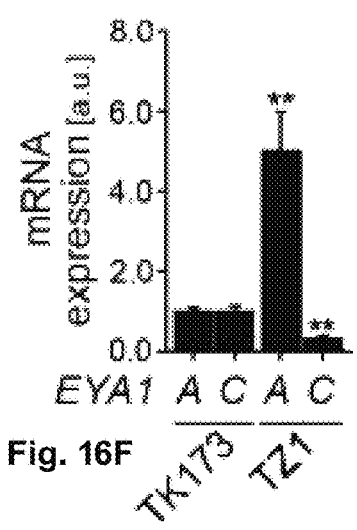
FIG. 16F depicts relative mRNA expression levels of isoforms EY1A and EYA1C, analyzed by qRT-PCR (n=3 independent replicates, data are presented as means±s.d., p<0.01, values of p were calculated using Student's t test comparing TZ1$^{SNP+/+}$ with TK173$^{SNP-/-}$ cultures).
Figure 16G:
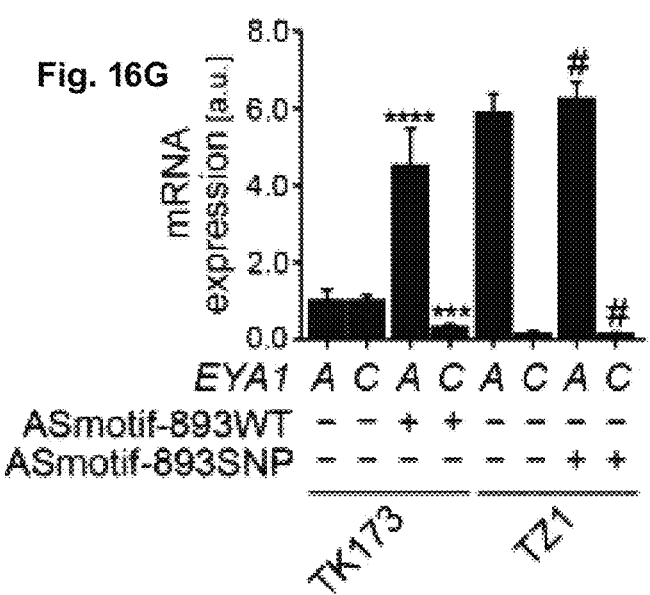
FIG. 16G shows a graph reflecting relative mRNA expression levels of isoforms EYA1A and EYA1C after administration of morpholinos to block the wildtype (ASmotif-893WT) or SNP rs13259388 (ASmotif-893SNP) motif, analyzed by qRT-PCR (n=3 independent replicates, data are presented as means±s.d., *p<0.001, **p<0.0001, # no significance, values of p were calculated using Student's t test comparing ASmotif-893WT/SNP with control cultures).
Figure 16H:
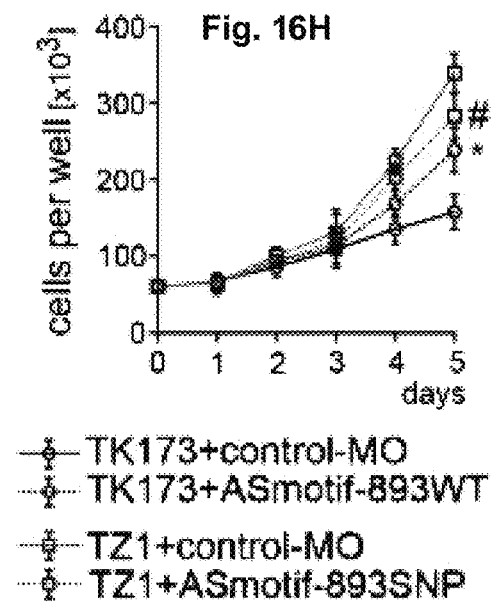
FIG. 16H** depicts the proliferative activity of human kidney fibroblasts seeded at a density of 60,000 per well, determined at indicated time points after ASmotif-893WT administration to TK173$^{SNP-/-}$ and ASmotif-893SNP administration to TZ1$^{SNP+/+}$ fibroblast cultures (n=3 independent replicates, data are presented as means±s.d., *p<0.01, # no significance, values of p were calculated using Student's t test comparing morpholino-treated TK173$^{SNP-/-}$ or TZ1$^{SNP+/+}$ with control cultures).

The inventors next screened and compared renal fibroblasts that had been established from patients homozygous for the wildtype "C" allele (TK173) or homozygous for the SNP rs3259388 "T" allele (TZ1, FIG. 16E). Homozygous SNP rs13259388 TZ1 cultures mirrored enhanced exon 10 inclusion (FIG. 16F), resulting in accelerated NHEJ DDR (FIGS. 20A to 20F). Morpholinos to block SNP rs13259388 (ASmotif-893SNP) motif in TZ1 did not further enhance EYA1 exon 10 inclusion (FIG. 16G), indicating that identified splicing cis regulatory motif plays an important role in EYA1 exon 10 splicing and SNP rs13259388 is associated with disruption of such motif. Increased EYA1 exon 10 inclusion in TZ fibroblasts and TK173 transfected with ASmotif-893WT correlated with accelerated accumulation as compared to control TK173 fibroblast cultures (FIG. 16H).

Figures 17A, 17B:
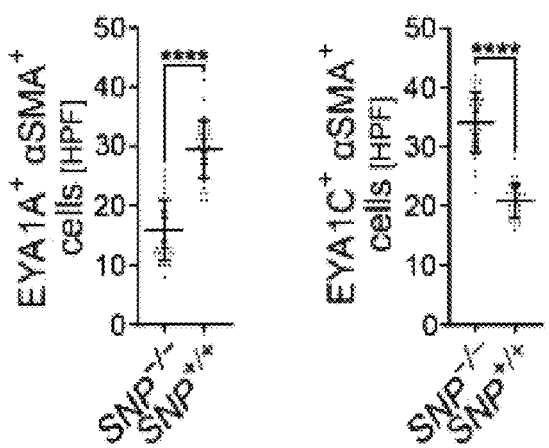
Figures 17C, 17D:
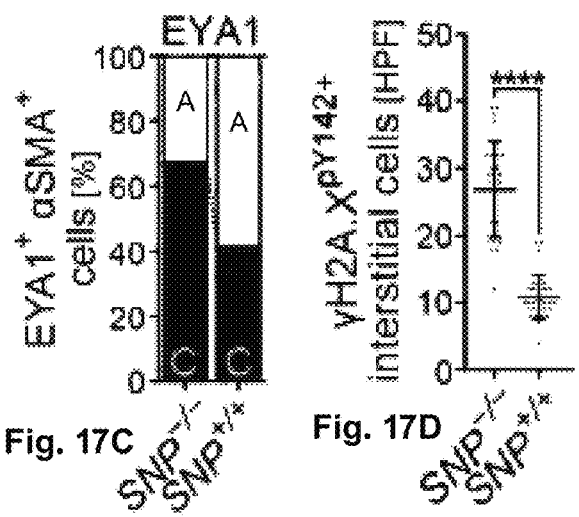
Figures 17E, 17F:
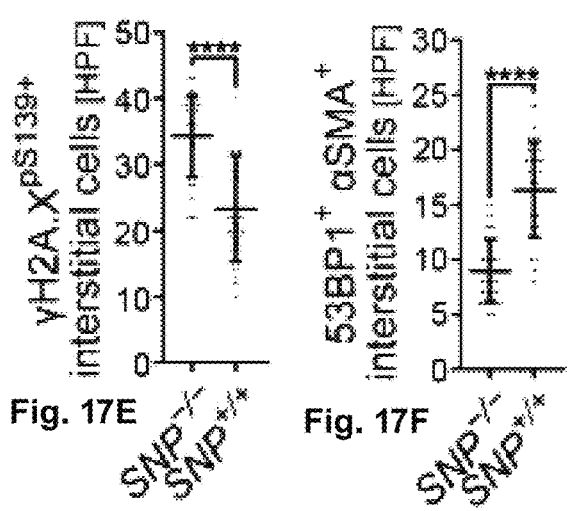
Figure 17G:
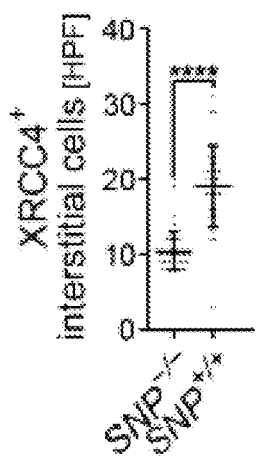
Figure 17H:
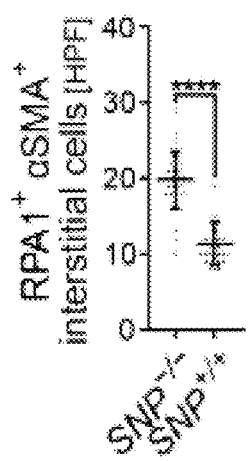
Figure 17I:
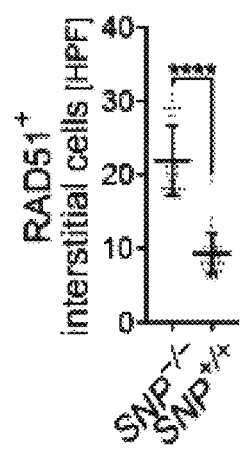
Figure 18C:
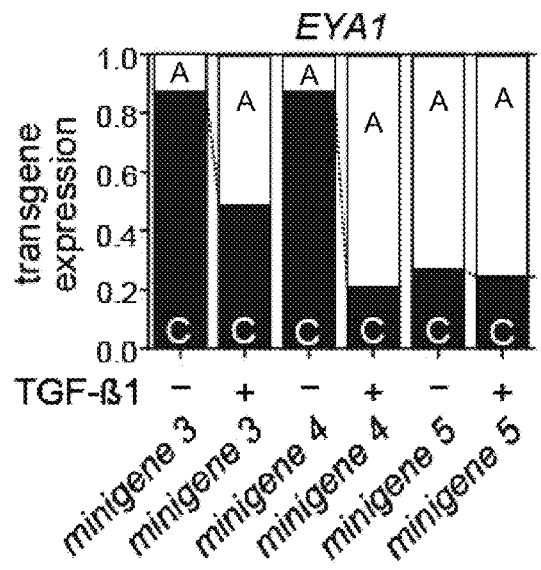
FIG. 18C** is a graphic representation, both reflecting relative mRNA levels of EYA1A and EYA1C in response to TGF-β1, analyzed by qRT-PCR (n=3 independent replicates, data are presented as means±s.d., *p<0.05, *p<0.001, values of p were calculated using Student's t test comparing control and TGF-β1-treated fibroblasts).
Figure 18D:
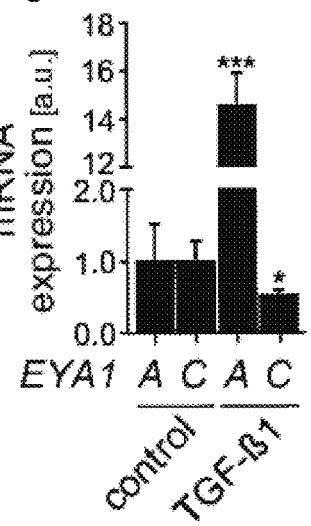
FIG. 18D** depicts relative mRNA levels of EYA1A and EYA1C in response to TGF-β1, analyzed by qRT-PCR (n=3 independent replicates, data are presented as means±s.d., *p<0.05, *p<0.001, values of p were calculated using Student's t test comparing control and TGF-1-treated fibroblasts).
Figure 18E:
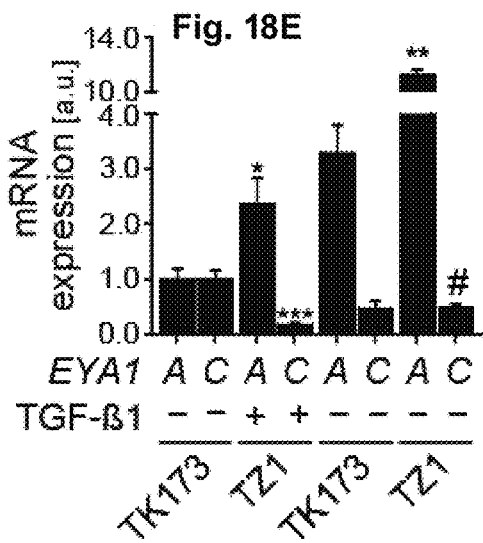
FIG. 18E** depicts relative mRNA expression levels of isoforms EY1A and EYA1C upon TGF-β1 exposure in TK173 and TZ1 fibroblast cultures, analyzed by qRT-PCR (n=3 independent replicates, data are presented as means±s.d., *p<0.05, p<0.01, *p<0.001, # no significance, values of p were calculated using Student's t test comparing TZ1 with TK173 cultures).
Figure 19A:
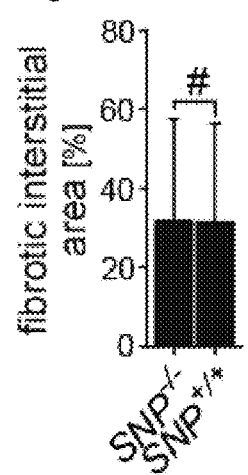
FIGS. 19A-19D summarize average means of fibrotic interstitial area (FIG. 19A), plasma creatinine (FIG. 19B), eGFR (FIG. 19C) and BUN (FIG. 19D) measurements comparing wildtype "C" allele (SNP$^{-/-}$) and homozygous SNP rs13259388 "T" allele (SNP$^{+/+}$) carriers (n=39, data are presented as means±s.d., # no significance, values of p were calculated using Student's t test comparing indicated groups).
Figure 19B:
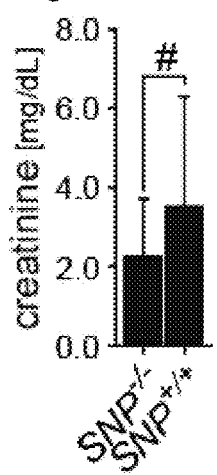
Figure 19C:
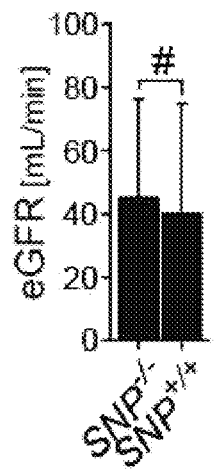
Figure 19D:
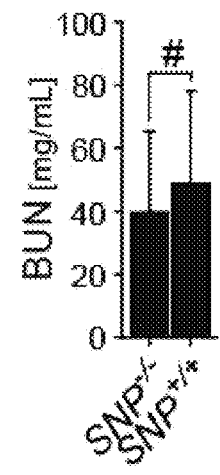
Figure 20A:
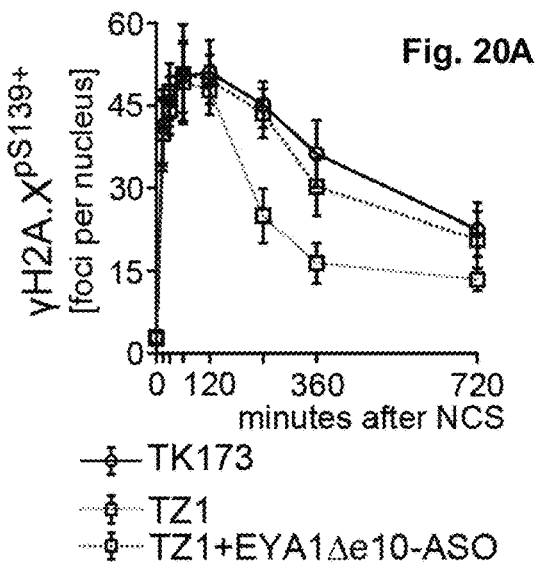
Figure 33D:
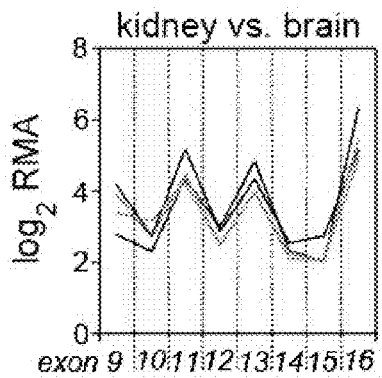
FIGS. 33D to H depict Log 2 robust multi-array average (RMA) values of EYA1 exons 9-16 encoding the EYA1 domain, extracted from publicly available exon array datasets (GEO accession number GSE41409), where EYA1 exon 10 splicing is equally detectable in brain (FIG. 33D), colon (FIG. 33E), liver (FIG. 33F), lung (FIG. 33G), and heart (FIG. 33H).
Figure 33E:
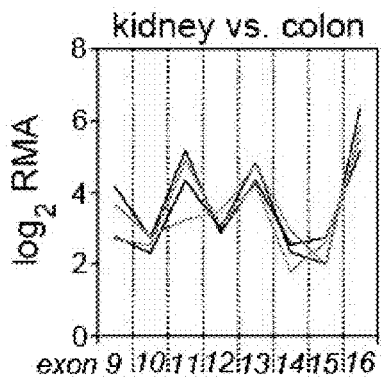
Figure 33F:
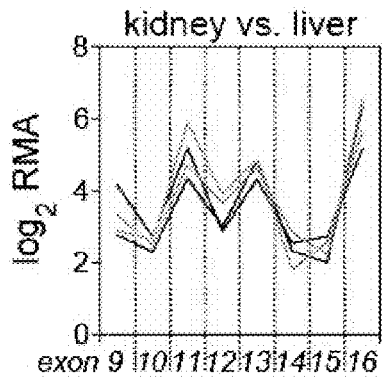
Figure 33G:
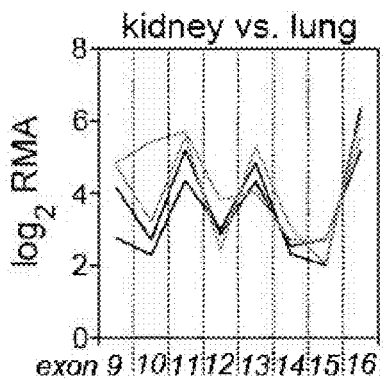
Figure 33H:
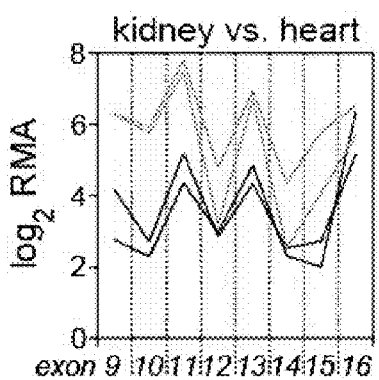
Figure 34:
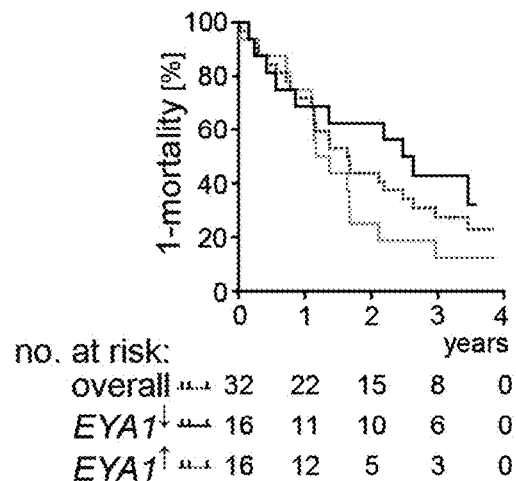
FIG. 34 depicts data on the correlation between expression of EYA1 and death in patients suffering from pancreas carcinoma. They axis depicts survivors (1-mortality). Data of 32 patients suffering from pancreas carcinoma at University hospital Goettingen were analysed. 16 patients had a low expression of EYA1 (black line), 16 patients had a high expression of EYA1 (grey line). Life expectancy compared to the entire group (dotted line) was significantly reduced in patients having a high expression of EYA1 (p=0.0033).

The inventors hypothesized that SNP rs13259388 was a risk factor for accelerated renal fibrosis. Within samples matched for fibrosis, fibroblast accumulation and renal excretory function, they observed increased EYA1 isoform switching towards EYA1A, lower abundance of γH2A.X$^{pS139}$, γH2A.X$^{pY142}$ and enhanced NHEJ DDR among biallelic SNP rs13259388 carriers (SNP+/+, FIGS. 17A to I). Because corresponding fibroblast cultures isolated from kidneys of biallelic SNP rs13259388 carriers accumulated more rapidly (FIG. 17J), ratio of EYA1A over EYA1C abundance within renal biopsies was previously associated with accelerated decline of renal function, and EYA1A overexpression had causally accelerated fibroblast accumulation and renal fibrogenesis in rodent models, we next analyzed disease progression towards ESRD in biallelic SNP rs13259388 carriers. Independent of kidney fibrosis extent or renal excretory function (FIGS. 19A to D), an overall 5.8-fold increase in relative risk to progress towards ESRD within 5 years among homozygous SNP rs13259388 carriers resulted in ESRD within a mean of 14.3 months as compared to 30.5 months in patients negative for SNP rs13259388 (FIG. 17K).

Because isoform EYA1A is not limited to SNP rs13259388 carriers but is the predominant isoform in any fibrotic human kidney, the inventors also aimed to gain insights into additional mechanisms underlying EYA1 exon 10 splicing. Transforming Growth Factor-beta1 (TGF-□1) is a principal mediator of fibrosis and fibroblast proliferation (Tampe & Zeisberg, 2014, supra), and identified splicing cis regulatory motif is a known binding site of TGF-□1-responsive splicing factors SRp40, SRp55 and SF2/ASF (Li X., & Manley J. L., Cell (2005) 122, 365-378). Accelerated fibroblast accumulation upon TGF-□1 exposure corresponded with increased mRNA expression of isoform EYA1A and decreased levels of isoform EYA1C and accelerated observed EYA1 isoform switch in TZ1 fibroblasts cultures (FIGS. 18A to E), further corroborating relevance of TGF-□1 in alternative splicing regulation and suggesting that SNP rs13259388 in humans accelerates EYA1 exon 10 inclusion.

After it had been observed that forced EYA1 exon 10 inclusion through oligonucleotides blocking identified splicing enhancer motif could induce the pro-fibrotic proliferative fibroblast phenotype, the inventors next asked if modulation of EYA1A exon 10 alternative splicing (disrupting EYA1 tyrosine phosphatase activity) could restore physiological HR/NHEJ balance and susceptibility to checkpoint activation. By generating oligonucleotides targeting intron 9-10/exon 10 and exon 10/intron 10-11 splice junctions (EYA1Δe10-ASO), exon 10 inclusion was effectively blocked (FIG. 21), correlating with normalization of premature $\gamma H2A.X^{pY14}$ dephosphorylation, increased HR DDR, attenuated proliferative activity and normalized DNA damage checkpoint activation (FIGS. 20A to H), confirming the causal link between SNP rs13259388, enhanced EYA1A generation and accelerated fibroblast proliferation and suggesting that SNP rs13259388-associated fibrosis risk can be therapeutically targeted in principle.

Discussion

Sustained fibroblast proliferation is a hallmark of tissue fibrosis. In light of abundant DNA damage within fibrotic tissues that prompts epithelial cells to enter cell cycle arrest and senescence, fibroblast require distinct DDR pathways to enable sustenance of proliferation. Here, we demonstrate that accelerated recruitment of NHEJ core proteins enables proliferating fibroblasts to escape DNA damage checkpoint activation, and that this switch in humans is caused by premature dephosphorylation of the Y142 residue of γH2A.X through eyes absent homolog EYA1A as a critical exon 10 is retained. The present data also show that the common intronic SNP rs13259388 causally worsens clinical outcome of chronic kidney disease patients through accelerated EYA1 exon 10 retention. Of note, this mechanism not only depends on presence of EYA1 tyrosine phosphatase activity, but also on recruitment of its substrate γH2A.X.

In this regard, relative abundance of H2A.X within nucleosomes differs substantially among cell types (Bonner W. M., et al., Nat Rev Cancer (2008) 8, 957-967, doi:10.1038/nrc2523; Rogakou, E. P., et al., J Biol Chem (1998) 139 273, 5858-5868). Within the kidney, H2A.X is far more abundant in fibroblasts than in tubular epithelial cells, and we did not observe an impact of EYA1A overexpression on tubular epithelial cell proliferation. The inventors' findings that EYA1A-induced premature $\gamma H2A.X^{pY142}$ dephosphorylation is associated with γH2A.X clearance is in line with existing literature demonstrating that phosphorylation of the S139 residue of H2A.X is critical for checkpoint activation upon DNA damage and that γH2A.X clearance terminates checkpoint activation (Stewart G.S., et al., Nature (2003) 421, 961-966). The present data unifies studies from different fields which demonstrated that γH2A.X is abundantly present within fibrotic human kidneys (Zhou et al., 2012, supra), that $\gamma H2A.X^{pY142}$ is a substrate of EYA1 tyrosine phosphatase activity (Cook et al., 2009, supra; Rayapureddi et al., 2003, supra), that γH2A.X is involved in DDR cell fate decisions (13), and that HR is a prerequisite for checkpoint activation (Stewart et al., 2003, supra). The present findings are also supported by publicly available CKD expression profiling datasets (GSE69438) that demonstrate that accelerated fibrosis correlated with increased expression of NHEJ core proteins (and decreased expression of HR) (Ju W., et al., Sci Transl Med (2015) 7, 316ra193).

It is furthermore shown that aberrant EYA1 exon 10 inclusion is enhanced by intronic, non-coding SNP rs13259388, a common variant, in a disease relevant manner (Genomes Project et al., 2012, supra). Generally, EYA1 splicing does not occur in any other species but humans, not even in other primates (Aken, B. L., et al. The Ensembl gene annotation system. Database (Oxford) 2016 (2016), doi: 10.1093/database/baw093). The relevance of SNP rs13259388 for EYA1 exon 10 retention is supported by phylogenetic analysis which revealed presence of a conserved genomic region within EYA1 corresponding to identified intronic splicing cis regulatory motif among primate species in which EYA1 is not alternatively spliced and EYA1 exon 10 is retained (Aken et al., 2016, supra).

Plausibility of identified impact of SNP rs13259388 as critical splicing cis regulatory motif of EYA1 exon 10 splicing is supported by Mfold pre-mRNA secondary structure analysis, predicting loop formation through RNA bridges connecting identified distal splicing cis regulatory motif to proximity of EYA1 exon 10 (FIG. 29B), in effect recapitulating the classical example of alternative splicing regulation proximal to alternative exons (Lovci, M. T., et al. Nat Struct Mol Biol (2013) 20, 1434-1442).

It can furthermore be taken from FIG. 29 that EYA1 exon 10 spicing is not limited to the kidney, but also present in chronically injured heart, lung and liver. This is in line with mining of publicly available human exon array datasets (GSE41409): compared to normal kidney, EYA1 exon 10 splicing is equally detectable in brain, colon, lung, and heart (FIGS. 29C to G; Ling, M. H., et al., BMC Genomics (2013) 14, 243). In light of the absence of clinically approved drugs to target progressive kidney fibrosis, the present findings point to several new targets for possible therapeutic intervention such as modulation of EYA1 splicing, inhibition of EYA1 tyrosine phosphatase activity and/or specific targeting of the NHEJ pathway or DNA damage checkpoint activation. Hence, the present inventors have identified a unique mechanism of alternative splicing, allowing dynamic realization of serine phosphatase/transcription factor and tyrosine/histone $\gamma H2A.X^{pY142}$ phosphatase activity of EYA1, and providing several novel therapeutic targets to inhibit fibrogenesis of the kidney.

Materials and Methods

Human Kidney Specimens

The use of parts of human kidney biopsies for research purposes was approved by the Ethics Committee of the University Medicine Goettingen, and written consent was obtained from all subjects before kidney biopsy.

Animals

All studies and inclusion/exclusion of animals were performed according to the German animal care and ethics legislation and had been carried out with the approval of the local government authorities (LAVES) and the University Medicine Goettingen. Experimental protocols are detailed below.

Generation of Doxycycline (DOX)-Inducible Transgenic Mice

German All transgenic mouse strains were obtained by the same founders and did not obtain spontaneous phenotypes. From 3 days before surgery, C57BL/6 (referred as wildtype) or transgenic mice overexpressing human splice variants EYA1A (rtTACMV;hEYA1A-pTreTight, referred to as EYA1A$^{tg}$) and EYA1C (rtTACMV;hEYA1C-pTreTight, referred to as EYA1C$^{tg}$) were treated with either vehicle buffer (glucose 5%) or DOX (2 mg/ml, Sigma, St. Louis, USA) within drinking water ad libidum and renewal every 2 days.

Unilateral Ureteral Obstruction (UUO)

Mice were anesthetized with isoflurane inhalation (2-3%), analgesia was performed by subcutaneous injection of 0.1 mg/kg body weight per day Buprenorphine. The ureter was separated from the surrounding tissues and two ligatures were placed about 5 mm apart in upper two-thirds of the left ureter to obtain reliable obstruction. Mice were sacrificed 3, 7 or 10 days after ureteral obstruction for further analyses.

⅚ Nephrectomy (⅚Nx)

The left kidney was exposed via a mid-line incision and the renal capsule was removed. The renal pedicle was temporarily clamped and approximately ⅞ of cortex was resected. The remnant kidney was wrapped with part of the mesentery and the clamp on the renal pedicle was removed, bleeding from the cut surfaces being prevented by 5 minutes of digital pressure. The abdominal incision was then closed and mice were allowed to recover.

$Na_3VO_4$ and Caffeine Treatment

Mice were injected intraperitoneally with $Na_3VO_4$ (8 mg/kg i.p. once per day, Sigma, St. Louis, USA) or caffeine (12.5 mg/kg i.p. once per day, Sigma, St. Louis, USA) starting one day prior of surgery, control mice received equivalent volume of PBS or DMSO.

Lentivirus Packaging

Lentiviral pLenti-Sce1 was produced in 293T virus packaging cells after transfection using a Packaging System Mix (Abmgood, Richmond, Canada) according to the manufacture's protocol. Lentiviral supernatant was collected 3 days after transfection, filtered through a 0.45 µm filter and concentrated with ultracentrifugation at 28,000 g at 4° C. using a 4% sucrose/PBS cushion for 3 hours. After supernatant removal viral particles were resuspended in PBS and stored at −80° C. Lentivirus titration was determined by Lenti-X qRTPCR Titration Kit (Clonetech, Heidelberg, Germany) and 8 µg/mL Polybrene (Sigma, St. Louis, USA) was used for in vivo application.

EYA1A$^{tg}$;R26NHEJ Transgenic Reporter Mice

R26NHEJ mice were crossed with EYA1A$^{tg}$ to generate EYA1Atg;R26NHEJ reporter mice. Mice were challenged with UUO and locally injected with intracortical pLenti-Sce1 (5×108 TU/100 µL) at 5 injection sites each.

SCR7 Treatment

Mice were injected intraperitoneally with SCR7 (20 mg/kg i.p. every alternate day, Sigma, St. Louis, USA) starting one day prior of surgery, control mice received equivalent volume of DMSO.

In Vivo Morpholino (VMO) Treatment

The inventors obtained 25 nucleotide antisense morpholino sequences (Gene Tools, Philomath, USA). The in vivo morpholinos contain a covalently linked octaguanidine dendrimer as a delivery moiety to facilitate entry into cells in vivo. Mice were injected intraperitoneally with 12.5 mg/kg body weight in vivo morpholinos in saline at a final volume of 100 µL every other day starting two days prior of surgery. A control in vivo Lentivirus Packaging Lentiviral pLenti-Sce1 was produced in 293T virus packaging cells after transfection using morpholino that targets a human β-globin intron mutation was used as standard control. In vivo morpholino sequences are those of SEQ ID NOs: 9 (EYA1A-VMO), 10 (53Bp1-VMO) and 16 (control).

Histology

Formalin-fixed, paraffin-embedded kidneys and hearts from mice, and HOPE-fixed, paraffin-embedded human specimens were sectioned at 3 µm, Masson's Trichrome Stain (MTS) was performed at the University Medicine Göttingen. For morphometric analysis of interstitial fibrosis in mice and human biopsies, we assessed the fibrotic area using cellSens (Olympus, Tokyo, Japan) software. Ten visual fields were selected randomly for each MTS stained section at 200× magnification and the relative interstitial fibrotic area was evaluated by using a 10 mm² graticule.

Immunohistochemistry

Formalin-fixed, paraffin-embedded kidneys and hearts from mice, and HOPE-fixed, Formalin-fixed, paraffin-embedded kidney sections from mice as well as from HOPE-fixed, paraffin-embedded human specimens were deparaffinized in xylene and rehydrated in ethanol containing distilled water. Tissue sections were stained using antibodies against p-Chk1$^{pS317}$ (12302P, Cell Signaling, Danvers, USA), Rad51 (sc-8349, Santa Cruz Biotechnology, Dallas, USA), Xrcc4 (sc-8285, Santa Cruz Biotechnology, Dallas, USA), H2A (ab13923, Abcam Biochemicals, Cambridge, UK), H2A.X (ab11175, Abcam Biochemicals, Cambridge, UK), γH2A.X$^{pS139}$ (ab2893, Abcam Biochemicals, Cambridge, UK) and γH2A.X$^{pY142}$ (ab94602, Abcam Biochemicals, Cambridge, UK), peroxidase labeling was performed using Vectastain Universal Elite ABC Kit (Vector Laboratories, Burlingame, USA) according to the manufacturer's protocol.

AEC Substrate-Chromogen (Dako, Glostrup, Denmark) was applied for peroxidase visualization according to the manufacturer's protocol. Nuclear counterstain was performed by using Mayer's Hematoxylin Solution (Sigma, St. Louis, USA).

Immunofluorescence Staining of Tissue Sections

Formalin-fixed, paraffin-embedded kidney sections from mice as well as from HOPE-fixed, paraffin-embedded human specimens were deparaffinized in xylene and rehydrated in ethanol containing distilled water. For immunofluorescent staining, EYA1 isoform antisera or primary antibodies against αSMA (A5228, Sigma, St. Louis, USA), Collagen-1 (ab34710, Abcam Biochemicals, Cambridge, UK), γH2A.X$^{pS139}$ (ab2893, Abcam Biochemicals, Cambridge, UK), γH2A.X$^{pS139}$ (05-636, Merck Millipore, Billerica, UK), γH2A.X$^{pY142}$ (ab94602, Abcam Biochemicals, Cambridge, UK), p-Chk1$^{pS317}$ (12302P, Cell Signaling, Danvers, USA), p-Chk2$^{pT68}$ (2197S, Cell Signaling, Danvers, USA), Rpa1 (2267S, Cell Signaling, Danvers, USA), Rad51 (sc-8349, Santa Cruz Biotechnology, Dallas, USA), 53Bp1 (sc-22760, Santa Cruz Biotechnology, Dallas, USA), Xrcc4 (sc-8285, Santa Cruz Biotechnology, Dallas, USA) and GFP (MA5-15256, Thermo Fisher Scientific, Waltham, USA) were used, secondary antibodies were labeled with Alexa Fluor 488, 594 or 647 (Life Technologies, Carlsbad, USA). Renal basement membranes were stained with antibodies against Collagen-4 (1340-30, SouthernBiotech, Birmingham, USA). Nuclear staining was performed using 4',6-diamidino-2-phenylindole (DAPI, Vector Laboratories, Burlingame, USA). Quantifications were performed per high power field at 400× magnification, representative confocal pictures using an LSM 780 confocal laser scanning microscope (Zeiss, Oberkochen, Germany) are shown.

Primary Mouse Fibroblasts

For isolation of primary mouse fibroblasts, freshly isolated kidneys were cut into small pieces (1-2 mm$^3$) and transferred into sterile filtered Collagenase Type 11 (100 U/mL) dissolved in serum free Dulbecco's modified Eagle medium (Gibco, Carlsbad, USA). After 45 minutes of digestion at 37° C. with mild agitation, cells were spun down and transferred into Dulbecco's modified Eagle medium (Gibco, Carlsbad, USA) supplemented with 2 mmol/L L-glutamine, 100 g/ml penicillin, 100 g/ml streptomycin, and 20% heat-inactivated fetal bovine serum (Cellgro, Manassas, USA) at 37° C. in 5% $CO_2$. Primary kidney fibroblasts emerged within a few days as adherent cells on the monolayer and were maintained in Dulbecco's modified Eagle medium (Gibco, Carlsbad, USA) supplemented with 2 mmol/L L-glutamine, 100 g/mL penicillin, 100 g/mL streptomycin, and 10% heat-inactivated fetal bovine serum (Cellgro, Manassas, Va.) at 37° C. in 5% $CO_2$. For all experiments, fibroblasts from passages 1 to 3 were used.

Primary Human Fibroblasts

The use of parts of nephrectomy specimens or kidney biopsies for research purposes was approved by the ethics committee of the Medical University of Goettingen, and written consent was obtained from all patients prior to kidney biopsy. For isolation of primary human kidney fibroblasts, renal biopsy cylinders were cut and immersed in Dulbecco's modified Eagle medium (Gibco, Carlsbad, USA) supplemented with 2 mmol/L L-glutamine, 100 g/ml penicillin, 100 g/ml streptomycin, and 20% heat-inactivated fetal bovine serum (Cellgro, Manassas, USA) at 37° C. in 5% $CO_2$ until fibroblasts had grown out to confluency. Primary human fibroblasts were used at passages 2 and 3. The use of parts of nephrectomy specimens or kidney biopsies for research purposes was approved by the ethics committee of the Medical University of Goettingen, and written consent was obtained from all patients prior to kidney biopsy. For isolation of primary human kidney fibroblasts, renal biopsy cylinders were cut and immersed in Dulbecco's modified Eagle medium (Gibco, Carlsbad, USA) supplemented with 2 mmol/L L-glutamine, 100 g/ml penicillin, 100 g/ml streptomycin, and 20% heat-inactivated fetal bovine serum (Cellgro, Manassas, USA) at 37° C. in 5% $CO_2$ until fibroblasts had grown out to confluency. Primary human fibroblasts were used at passages 2 and 3.

Cell Culture

Human SV40/large T antigen-immortalized monoclonal kidney fibroblasts (TK173 and TZ1) were cultured in Dulbecco's modified Eagle medium (Gibco, Carlsbad, USA) supplemented with 2 mmol/L L-glutamine, 100 g/mL penicillin, 100 g/mL streptomycin, and 10% heat-inactivated fetal bovine serum (Cellgro, Manassas, Va.) at 37° C. in 5% $CO_2$. HK-2 (ATTC, Manassas, USA) are immortalized proximal tubule epithelial cells derived from normal adult human kidney. All cells were routinely tested negative for the presence of *mycoplasma* contamination. None of the cell lines used in this manuscript is listed in the ICLAC and NCBI Biosample database of misidentified cell lines. Cells were cultured in Dulbecco's modified Eagle's (DMEM, Gibco, Carlsbad, USA) medium supplemented with 100 g/mL penicillin, 100 g/mL streptomycin and 10% heat-inactivated fetal bovine serum (FBS, Sigma, St. Louis, USA) at 37° C. in 5% $CO_2$.

G2 Cell Synchronization and Neocarzinostatin (NCS) Treatment

Transgenic EYA1A$^{tg}$ and EYA1C$^{tg}$ primary fibroblast cultures were seeded in 8 well chamber slides (Thermo Fisher Scientific, Waltham, USA) at a concentration of 2×10$^3$ cells per well in antibiotic-free DMEM (Gibco, Carlsbad, USA) supplemented with 10% heat-inactivated fetal bovine serum (FBS, Sigma, St. Louis, USA). After 12 hours, thymidine (2 mM, Sigma, St. Louis, USA) and DOX (1 µg/mL, Sigma, St. Louis, USA) were added to culture media for 20 hours and replaced by antibiotic-free DMEM (Gibco, Carlsbad, USA) supplemented with 10% heat-inactivated FBS (Sigma, St. Louis, USA) and DOX (1 µg/mL, Sigma, St. Louis, USA). After 4 hours, nocodazole (25 ng/mL, Sigma, St. Louis, USA) and DOX (1 µg/mL, Sigma, St. Louis, USA) were added to culture media for additional 12 hours. Culture media was replaced by antibiotic-free DMEM (Gibco, Carlsbad, USA) supplemented with 10% heat-inactivated FBS (Sigma, St. Louis, USA) and NCS (10 ng/mL, Sigma, St. Louis, USA), cells were collected at indicated time points. For overexpression experiments, murine and human fibroblast cultures were seeded in 8 well chamber slides (Thermo Fisher Scientific, Waltham, USA) at a concentration of 2×10$^3$ cells per well in antibiotic-free DMEM (Gibco, Carlsbad, USA) supplemented with 10% heat-inactivated fetal bovine serum (FBS, Sigma, St. Louis, USA).

After 24 hours, 2 µg plasmid DNA was transfected using Lipofectamine 2000 reagent (Invitrogen, Carlsbad, USA) for 4 hours and culture media was replaced by antibiotic-free DMEM (Gibco, Carlsbad, USA) supplemented with 10% heat-inactivated FBS (Sigma, St. Louis, USA). After additional 20 hours, thymidine (2 mM, Sigma, St. Louis, USA) was added to culture media for 20 hours and replaced by antibiotic-free DMEM (Gibco, Carlsbad, USA) supplemented with 10% heat-inactivated FBS (Sigma, St. Louis, USA). After 4 hours, nocodazole (25 ng/mL, Sigma, St. Louis, USA) was added to culture media for additional 12 hours. Culture media was replaced by antibiotic-free DMEM (Gibco, Carlsbad, USA) supplemented with 10% heat-inactivated FBS (Sigma, St. Louis, USA) and NCS (10 ng/mL, Sigma, St. Louis, USA), cells were collected at indicated time points.

Immunofluorescence Staining of Fixed Cells

Cells were fixed in 4% paraformaldehyde (PFA) for 10 minutes at room temperature, permeabilized with 0.5% Triton-X 100 for 10 minutes and blocked with 3% bovine serum albumin (BSA) for 1 hour at 4° C. For immunofluorescent staining, primary antibodies against γH2A.X$^{pS139}$ (05-636, Merck Millipore, Billerica, UK), γH2A.X$^{pY142}$ (ab94602, Abcam Biochemicals, Cambridge, UK), Rpa1 (2267S, Cell Signaling, Danvers, USA), Rad51 (sc-8349, Santa Cruz Biotechnology, Dallas, USA), 53Bp1 (sc-22760, Santa Cruz Biotechnology, Dallas, USA), Xrcc4 (sc-8285, Santa Cruz Biotechnology, Dallas, USA), DDK (TA50011-100, OriGene, Rockville, USA) were used, secondary antibodies were labeled with Alexa Fluor 488, 594 or 647 (Life Technologies, Carlsbad, USA). Nuclear staining was performed using DAPI (Vector Laboratories, Burlingame, USA). An LSM 780 confocal laser scanning microscope (Zeiss, Oberkochen, Germany) was used, representative confocal pictures are shown.

COMET Assay

Neutral COMET assay was performed as recommended by the manufacturer (Trevigen, Gaithersburg, USA). Briefly, a suspension of 500 cells were included in low-melting agarose and run on a pre-coated agarose-covered slide. After the agarose gelled, slides were run at 21 V for 30 minutes at 4° C. and subsequently stained with SYBR Green diluted 1:10,000 in TE buffer (pH 7.5).

NHEJ/HR Reporter Plasmids

Primary murine fibroblast cultures were stably transfected using Lipofectamine 2000 reagent as recommended by the manufacturer (Invitrogen, Carlsbad, USA). Briefly, 2 µg of circular pEGFP-Pem1-Ad2 or pDR-GFP (AddGene, Cambridge, USA), resistant colonies were selected with 6 µg/mL puromycin (Thermo Fisher Scientific, Waltham, USA). After transfection of an I-SceI rare-cutting endonuclease from Saccharomyces cerevisiae expression vector (pCBAS-ceI, AddGene, Cambridge, USA) to introduce a DSB at genomic I-SceI sites, NHEJ/HR repair events were visualized by presence of cells positive for EGFP/GFP

Morpholino Treatment In Vitro

For in vitro experiments, a final concentration of 10 µM morpholinos (without a covalently linked octaguanidine dendrimer) blocking the intronic splicing cis regulatory wildtype (ASmotif-893WT) or SNP rs13259388 motif (AS-motif-893SNP) were scrape delivered to TK173 or TZ1, respectively. A control morpholino that targets a human β-globin intron mutation was used as standard control (control-VMO: SEQ ID NO: 16; EYA1A-VMO: SEQ ID NO: 9; 53BP1-VMO: SEQ ID NO: 10).

Antisense Oligonucleotides

Oligonucleotides targeting intron 9-10/exon 10 (EYA1Δe10-5'ASO, SEQ ID NO: 5) and exon 10/intron 10-11 (EYA1Δe10-3'ASO, SEQ ID NO: 4) splice junctions (referred to as EYA1Δe10-ASO) were transfected using Lipofectamine 2000 reagent (Invitrogen, Carlsbad, USA) for 4 hours and culture media was replaced by antibiotic-free DMEM (Gibco, Carlsbad, USA) supplemented with 10% heat-inactivated FBS (Sigma, St. Louis, USA).

Peptide Synthesis and Antibody Generation

The antigenic peptides were selected from the protein sequence using the Lasergene software (DNASTAR, Madison, USA) and additionally for non-homologous sequence pattern: The peptides were synthesized with an additional N-terminal cysteine using standard Fmoc/tBu chemistry on a multiple peptide synthesizer, Syro II (MultiSynTech, Witten, Germany) as recently described. The single peptides were purified using reversed phase-HPLC and their identity was confirmed using ESI-MS and MALDI-TOF-MS. Peptide purities were >95% as determined by analytical reversed phase-HPLC. Four peptides as antigens were used: CEEMIFNLADTHLF FNDLE [330-347, SEQ ID NO: 38] (EYA1 isoform A), CGSSESPSGPKLGNSHINS [15-32, SEQ ID NO: 17] (EYA1 isoform C), CMEMQDLT-SPHSRLSGSSES [1-19, SEQ ID NO: 18] (EYA1 isoform C), GISSYGIKTEGGLS [135-148, SEQ ID NO: 19] (EYA1 isoform C). The peptides were specifically coupled via their N-terminal cysteine to maleimidobenzoyl-functionalized-keyhole hole hemocyanin (MBS-KLH) and the antisera were obtained after repeated immunization of rabbits with a 1:1-mixture of the peptide-KLH conjugate.

Mutant Constructs

Mutant EYA1A in which exon 10 had been removed (EYA1Δe10) was generated by amplification from EYA1A overexpression vector (OriGene, Rockville, USA) with specific restriction enzyme sites for exons 1-9 (EcoRI and KpnI) and exons 11-16 (KpnI and Xho). Mutant EYA1C where exon 1' was replaced with exon 1 (EYA1CΔ1'::e1) was generated by amplification from EYA1A and EYA1C overexpression vectors (OriGene, Rockville, USA) with specific restriction enzyme sites for exons 1-4 (EcoRI and NheI) and exons 5-16 (NheI and XhoI), respectively. Mutant EYA1C to which exon 10 had been added (EYA1C::e10) was generated by amplification from EYA1C and EYA1A overexpression vectors (OriGene, Rockville, USA) with specific restriction enzyme sites for exons 1'-9/11-16 (BglII and HindIII) and exon 10 (HindIII and BglII), respectively. Standard PCR reactions with high-fidelity taq-polymerase under condition of denaturing at 98° C. for 30 seconds, annealing at 72° C. for 30 seconds and elongation at 72° C. for 30 seconds to 45 seconds depending on the length of the fragment for 45 cycles were used. Generated fragments were cloned, constructs were validated by sequencing of the connected regions.

Minigene Constructs

Minigens harboring exons 1-10 and intronic fragments flanking exon 10 containing cis regulatory elements −1165 relative to intron 9-10/exon 10 junction (minigene 3), lacking −1165 bp to −920 bp relative to intron 9-10/exon 10 junction (minigene 4) or lacking −1164 bp to −634 bp relative to intron 9-10/exon 10 junction (minigene 5) were generated. EYA1 intron 9-10, exon 10 and intron 10-11 fragments were amplified from bacclone RP 11-11K9 (minigenes 3, 4 and 5) or genomice DNA extracted from human renal fibroblasts which had been established from patients homozygous for the SNP rs13259388 "T" allele (TZ1$^{SNP+/+}$) at −893 bp relative to intron 9-10/exon 10 junction (minigene 4 SNP) with specific restriction enzyme sites (KpnI and NotI) by standard PCR reactions with high-fidelity taq-polymerase under condition of denaturing at 98° C. for 30 seconds, annealing at 72° C. for 30 seconds and elongation at 72° C. for 30 seconds to 45 seconds depending on the length of the fragment for 45 cycles.

These fragments were cloned into pCMV6-Entry mammalian vector (OriGene, Rockville, USA), constructs were validated by sequencing of the connected regions. After detecting the right construct, DNA was isolated with MINI Prep Kit (Qiagen, Hilden, Germany). EYA1 exon 1-9 fragments were amplified from EYA1 Isoform A overexpression plasmid with specific restriction enzyme sites (NheI and KpnI). This fragment was cloned into the constructs containing one of the fragments with exon 10. Again, constructs were validated by sequencing of the connected regions.

RNA Isolation

Total RNA was extracted from cells using TRIzol Reagent (Life technologies, Carlsbad, USA), tissue was shredded using TissueLyser LT (Qiagen, Hilden, Germany). Subsequent RNA purification procedure was performed by PureLink RNA Mini Kit (Ambion, Carlsbad, USA) according to the manufacturer's protocol.

RNA Sequencing and Gene Set Enrichment

Total RNA extracted from UUO kidneys were submitted to Transcriptome Sequencing Service of Eurofins Genomics and provided in GEO (accession number GSE92934, reviewer link: https://www.ncbi.nlm.nih.gov/geo/query/acc.cgi?token=wnatgiqsrpytxcv&acc=GSE92934). Raw read counts were created using HTSeq. Only reads with unique mapping positions were considered for read counting. Only reads overlapping exon-features were counted. All reads mapping to features with the same identifier were summed, the "gene"-attribute was used as feature identifier. Reads mapping to multiple features with different identifier were ignored for read counting. Gene set enrichment and process analysis (values of p<0.001) were performed using Gene Ontology enRIchment anaLysis and visuaLizAtion tool (GORILLA).

Quantitative Real-Time PCR Quantification (qRT-PCR)

qRT-PCR analyses were performed using the ABI One Step Plus instrument and software (PE Applied Biosystems, Inc., Foster City, Calif.). Using predesigned primers for total EYA1 (Hs00166804_m1, Applied Biosystems, Carlsbad, USA), EYA1A (Hs01011616_m1, Applied Biosystems, Carlsbad, USA) and EYA1C (Hs01004900_g1, Applied Biosystems, Carlsbad, USA), qRT-PCR was performed with the TaqMan® Universal PCR Master Mix (Applied Biosystems, Carlsbad, USA) using 10 µL of diluted total RNA, 10 µmol/L of the probe, and 10 µmol/L primers in a 50 µl final reaction mixture. Reverse transcription of input RNA to cDNA was performed at 48° C. for 30 minutes. After 10 minutes incubation at 95° C., 40 PCR cycles were performed consisting of 15 seconds of denaturation at 95° C. and hybridization of probe and primers for 1 minute at 60° C. each. Reactions were done in triplicates.

Relative expression levels were determined using standard methods. The gene expression value for the gene of interest was normalized to the value determined from rRNA 18S to adjust variances in the quality of RNA and the amount of input RNA. For SYBR-based real-time PCR, cDNA synthesis was performed by using DNase I digestion (Invitrogen, Carlsbad, USA) and SuperScript II Reverse Transcriptase (Invitrogen, Carlsbad, USA) according to the manufacturer's protocol. Briefly, 1 µL of reverse-transcribed cDNA was added to the reaction mixture containing the primer pair (200 nmol/L each) and diluted 2× Fast SYBR Green Master Mix (Applied Biosystems, Carlsbad, USA) in a final volume of 20 µL for each PCR reaction. The real-time PCR reactions were performed in a 96-well reaction plate using the StepOne Plus Real-Time System (Applied Biosystems, Carlsbad, USA) and were done in triplicates. An initiation step at 95° C. for 20 seconds was followed by 40 cycles at 95° C. for 3 seconds and 60° C. for 30 seconds, with one cycle of dissociation at 95° C. for 15 seconds, 60° C. for 60 seconds, and 95° C. for 15 seconds.

The intercalation of SYBR Green dye and its fluorescent signal is directly proportional to the amount of amplified DNA and was transformed into the cycle threshold (Ct). For normalization, the Ct values of the housekeeping genes Gapdh/GAPDH were subtracted from the Ct values of the gene of interest to generate the dCt values. The relative expression levels were analyzed in technical triplicates and calculated using the equation $2^{-ddCt}$. Sources and sequences of the oligonucleotides are listed in FIG. 35.

Electrophoresis of PCR products was done on a Bioanalyzer 2100 (Agilent Technologies, Santa Clara, USA) according to the manufacturer's protocol. Electrophoresis results are shown as virtual gel images and DNA concentrations relative to corresponding input DNA as described in our previous publications.

Western Blot Analyses

Tissue and cells were homogenized in NP40 lysis buffer (Life technologies, Carlsbad, USA) supplemented with protease inhibitor cocktail (Roche, Basel, Switzerland). After sonication, protein samples were resolved by a 4-12% Bis-Tris polyacrylamide gel electrophoresis system (Novex, Carlsbad, USA) and transferred onto a nitrocellulose membrane (GE Healthcare, Freiburg, Germany), followed by a blocking step with 5% dry milk or 5% BSA in TBST (TBS pH 7.2, 0.1% Tween-20) to prevent unspecific bindings.

After incubation with EYA1 isoform antisera or respective primary antibodies against H2A.X (ab11175, Abcam Biochemicals, Cambridge, UK), $\gamma H3^{pS10}$ (ab47297, Abcam Biochemicals, Cambridge, UK), p-Chk1$^{pS317}$ (12302P, Cell Signaling, Danvers, USA), p-Chk2$^{pT68}$ (2197S, Cell Signaling, Danvers, USA), β-actin (A5316, Sigma, St. Louis, USA) and Gapdh (5G4, HyTest, Turku, Finland), secondary HRP-conjugated antibodies were used (Dako, Glostrup, Denmark). Luminescence was detected by using chemiluminescent substrate (Cell Signaling, Danvers, USA) on a ChemiDoc XRS system (Bio-Rad, Hercules, USA).

pNPP Assay p-Nitrophenyl Phosphate (PNPP) is a non-proteinaceous, non-specific substrate used in the art to assay protein, alkaline and acid phosphatases. The PNPP phosphatase activity is measured using a continuous or single-point spectrophotometric assay based on the ability of phosphatases to catalyze the hydrolysis of PNPP to p-nitrophenol, a chromogenic product with absorbance at 405 nm. Any available protocol can be followed to determine phosphatase activity using pNPP.

Phosphatase Assay

Tyrosine and serine phosphatase activities in total cell lysates were determined using phosphotyrosine (V2471, Promega, Fitchburg, USA) and phosphoserine (17-128, Merck Millipore, Darmstadt, Germany) phosphatase assay systems according to the manufacturer's protocol.

Analyses of Publicly Available Array Datasets

Human transcriptome array data are shown as log 2 median centered intensities extracted from Nephroseq database (accession number GSE69438). To predict differential splicing events for EYA1, exon array CEL files (GEO accession number GSE41409) were taken into account and analyzed using AltAnalyze software and default parameters referenced to normal kidney exon array datasets. Splicing index algorithm were taken into account to assess splicing events, splicing index scores were obtained by subtracting normalized intensities of reference from experimental groups. Splicing index of 0 indicates equal inclusion rates between the two groups, positive values indicate enrichment of exons in experimental groups and negative values indicate enrichment of exons in the control groups as compared to experimental groups.

Identification of Candidate Cis Regulatory Elements

Candidate cis regulatory elements in alternative and constitutive splicing of mammalian exons was performed using SFmap with the SNP rs13259388 flanking region.

RNA Secondary Structure Prediction

Prediction of RNA bridge formation upstream EYA1 exon 10 was performed using Mfold.

Statistical Analysis

The numbers of biological replicates are indicated in the corresponding figure legends. For single group comparison, Student's t test was used to determine statistical significance. One-way ANOVA with Bonferroni post-hoc analysis was used for multiple comparisons of samples to determine statistical significance. Linear regression was performed comparing indicated pairs of parameters, $r^2$ and values of p are indicated in the corresponding graphs. Statistical significance was defined as values of $p<0.05$, indicated as $*p<0.05$, $p<0.01$, $*p<0.001$ or $****p<0.0001$. Prism 5 software (GraphPad, La Jolla, USA) was used for statistical analysis.

---

What is claimed is:

1. A method of preventing, treating or delaying progression of at least one of desmoplasia and fibrosis in a subject, wherein the method comprises administering a compound that reduces the level of tyrosine phosphatase activity effected by the protein EYA1,
wherein the compound is (i) an antisense oligonucleotide complementary to at least one of a portion of at least 11 consecutive bases within the sequence of SEQ ID NO: 34, or a complement of the portion within the sequence of SEQ ID NO: 34, (ii) an antisense oligonucleotide complementary to at least one of a portion of at least 11 consecutive bases within the sequence of SEQ ID NO: 35 and a complement of the portion within the sequence of SEQ ID NO: 35, or (iii) an antisense oligonucleotide complementary to at least one of a portion of at least 11 consecutive bases within the sequence of SEQ ID NO: 36 and a complement of the portion of the sequence of SEQ ID NO: 36.

2. The method of claim 1, wherein the antisense oligonucleotide complementary to a portion of at least 11 consecutive bases within the sequence of SEQ ID NO: 34 is an antisense oligonucleotide complementary to the sequence of SEQ ID NO: 39.

3. The method of claim 1, wherein the antisense oligonucleotide complementary to a portion of at least 11 consecutive bases within the sequence of SEQ ID NO: 34 is an antisense oligonucleotide complementary to the sequence of SEQ ID NO: 5.

4. The method of claim 1, wherein the antisense oligonucleotide complementary to a portion of at least 11 consecutive bases of the sequence of SEQ ID NO: 35 comprises the sequence of SEQ ID NO: 37.

5. The method of claim 1, wherein the antisense oligonucleotide complementary to a portion of at least 11 consecutive bases within the sequence of SEQ ID NO: 35 is an antisense oligonucleotide complementary to the sequence of SEQ ID NO: 40.

6. The method of claim 5, wherein the antisense oligonucleotide has the sequence of SEQ ID NO: 4.

7. The method of claim 1, wherein the antisense oligonucleotide complementary to a portion of at least 11 consecutive bases of the sequence of SEQ ID NO: 36 is an antisense oligonucleotide complementary to the sequence of SEQ ID NO: 9, or a complement thereof.

8. The method of claim 1, wherein the subject expresses a naturally occurring EYA1 protein comprising the sequence of SEQ ID NO: 2.

9. The method of claim 8, wherein the nucleic acid sequence encoding the protein EYA1 comprises the nucleic acid sequence of SEQ ID NO: 7 or the nucleic acid sequence of SEQ ID NO: 8.

10. The method of claim 1, wherein the antisense oligonucleotide is a phosphorodiamidate morpholino oligonucleotide.

* * * * *

SEQUENCE LISTING

<160> NUMBER OF SEQ ID NOS: 51

<210> SEQ ID NO 1
<211> LENGTH: 559
<212> TYPE: PRT
<213> ORGANISM: Homo sapiens

<400> SEQUENCE: 1

```
Met Leu Leu Phe Pro Gln Val Ala Val Lys Thr Glu Pro Met Ser Ser
1               5                   10                  15

Ser Glu Thr Ala Ser Thr Thr Ala Asp Gly Ser Leu Asn Asn Phe Ser
            20                  25                  30

Gly Ser Ala Ile Gly Ser Ser Ser Phe Ser Pro Arg Pro Thr His Gln
        35                  40                  45

Phe Ser Pro Pro Gln Ile Tyr Pro Ser Asn Arg Pro Tyr Pro His Ile
    50                  55                  60

Leu Pro Thr Pro Ser Ser Gln Thr Met Ala Ala Tyr Gly Gln Thr Gln
65                  70                  75                  80

Phe Thr Thr Gly Met Gln Gln Ala Thr Ala Tyr Ala Thr Tyr Pro Gln
                85                  90                  95

Pro Gly Gln Pro Tyr Gly Ile Ser Ser Tyr Gly Ala Leu Trp Ala Gly
            100                 105                 110

Ile Lys Thr Glu Gly Gly Leu Ser Gln Ser Gln Ser Pro Gly Gln Thr
        115                 120                 125

Gly Phe Leu Ser Tyr Gly Thr Ser Phe Ser Thr Pro Gln Pro Gly Gln
    130                 135                 140

Ala Pro Tyr Ser Tyr Gln Met Gln Gly Ser Ser Phe Thr Thr Ser Ser
145                 150                 155                 160

Gly Ile Tyr Thr Gly Asn Asn Ser Leu Thr Asn Ser Ser Gly Phe Asn
                165                 170                 175

Ser Ser Gln Gln Asp Tyr Pro Ser Tyr Pro Ser Phe Gly Gln Gly Gln
            180                 185                 190

Tyr Ala Gln Tyr Tyr Asn Ser Ser Pro Tyr Pro Ala His Tyr Met Thr
        195                 200                 205

Ser Ser Asn Thr Ser Pro Thr Thr Pro Ser Thr Asn Ala Thr Tyr Gln
    210                 215                 220

Leu Gln Glu Pro Pro Ser Gly Ile Thr Ser Gln Ala Val Thr Asp Pro
225                 230                 235                 240
```

-continued

```
Thr Ala Glu Tyr Ser Thr Ile His Ser Pro Ser Thr Pro Ile Lys Asp
                245                 250                 255

Ser Asp Ser Asp Arg Leu Arg Arg Gly Ser Asp Gly Lys Ser Arg Gly
            260                 265                 270

Arg Gly Arg Arg Asn Asn Asn Pro Ser Pro Pro Asp Ser Asp Leu
        275                 280                 285

Glu Arg Val Phe Ile Trp Asp Leu Asp Glu Thr Ile Ile Val Phe His
290                 295                 300

Ser Leu Leu Thr Gly Ser Tyr Ala Asn Arg Tyr Gly Arg Asp Pro Pro
305                 310                 315                 320

Thr Ser Val Ser Leu Gly Leu Arg Met Glu Glu Met Ile Phe Asn Leu
                325                 330                 335

Ala Asp Thr His Leu Phe Phe Asn Asp Leu Glu Glu Cys Asp Gln Val
            340                 345                 350

His Ile Asp Asp Val Ser Ser Asp Asp Asn Gly Gln Asp Leu Ser Thr
        355                 360                 365

Tyr Asn Phe Gly Thr Asp Gly Phe Pro Ala Ala Ala Thr Ser Ala Asn
    370                 375                 380

Leu Cys Leu Ala Thr Gly Val Arg Gly Gly Val Asp Trp Met Arg Lys
385                 390                 395                 400

Leu Ala Phe Arg Tyr Arg Arg Val Lys Glu Ile Tyr Asn Thr Tyr Lys
                405                 410                 415

Asn Asn Val Gly Gly Leu Leu Gly Pro Ala Lys Arg Glu Ala Trp Leu
            420                 425                 430

Gln Leu Arg Ala Glu Ile Glu Ala Leu Thr Asp Ser Trp Leu Thr Leu
        435                 440                 445

Ala Leu Lys Ala Leu Ser Leu Ile His Ser Arg Thr Asn Cys Val Asn
450                 455                 460

Ile Leu Val Thr Thr Thr Gln Leu Ile Pro Ala Leu Ala Lys Val Leu
465                 470                 475                 480

Leu Tyr Gly Leu Gly Ile Val Phe Pro Ile Glu Asn Ile Tyr Ser Ala
                485                 490                 495

Thr Lys Ile Gly Lys Glu Ser Cys Phe Glu Arg Ile Ile Gln Arg Phe
            500                 505                 510

Gly Arg Lys Val Val Tyr Val Val Ile Gly Asp Gly Val Glu Glu Glu
        515                 520                 525

Gln Gly Ala Lys Lys His Ala Met Pro Phe Trp Arg Ile Ser Ser His
530                 535                 540

Ser Asp Leu Met Ala Leu His His Ala Leu Glu Leu Glu Tyr Leu
545                 550                 555
```

```
<210> SEQ ID NO 2
<211> LENGTH: 18
<212> TYPE: PRT
<213> ORGANISM: artificial sequence
<220> FEATURE:
<223> OTHER INFORMATION: fragment of sequence of human EYA1A sequence

<400> SEQUENCE: 2

Ile Ile Val Phe His Ser Leu Leu Thr Gly Ser Tyr Ala Asn Arg Tyr
1               5                   10                  15

Gly Arg

<210> SEQ ID NO 3
<211> LENGTH: 25
```

```
<212> TYPE: PRT
<213> ORGANISM: artificial sequence
<220> FEATURE:
<223> OTHER INFORMATION: fragment of human EYA1A sequence

<400> SEQUENCE: 3

Ser Ser Phe Thr Thr Ser Ser Gly Ile Tyr Thr Gly Asn Asn Ser Leu
 1               5                  10                  15

Thr Asn Ser Ser Gly Phe Asn Ser Ser
             20                  25

<210> SEQ ID NO 4
<211> LENGTH: 16
<212> TYPE: DNA
<213> ORGANISM: artificial sequence
<220> FEATURE:
<223> OTHER INFORMATION: EYA1[delta]e10-3'-ASO

<400> SEQUENCE: 4
tttcaacttg gcagta                                                       16

<210> SEQ ID NO 5
<211> LENGTH: 16
<212> TYPE: DNA
<213> ORGANISM: artificial
<220> FEATURE:
<223> OTHER INFORMATION: EYA1[delta]e10-5'-ASO

<400> SEQUENCE: 5
ccttggactg cgaatg                                                       16

<210> SEQ ID NO 6
<211> LENGTH: 204
<212> TYPE: DNA
<213> ORGANISM: artificial
<220> FEATURE:
<223> OTHER INFORMATION: CpG island of human EYA1

<400> SEQUENCE: 6 ttttttttttt agtagtgaat ccggcccgcg tcaccgagta cggacattag ggtcgtgaaa      60
ccctccgact ccgtccgcct agtactccag tctagttctg gtaggaccgg ttgtaccact     120
ttgaggcaga gatgattttt atgttttttt taatcgacc agcacaacca cgcgcggaca     180
tcagggtcga tgagccctcc gact                                            204

<210> SEQ ID NO 7
<211> LENGTH: 17
<212> TYPE: DNA
<213> ORGANISM: artificial
<220> FEATURE:
<223> OTHER INFORMATION: fragment of sequence encoding human EYA1

<400> SEQUENCE: 7
ggccacacat aaaatac                                                      17

<210> SEQ ID NO 8
<211> LENGTH: 17
<212> TYPE: DNA
<213> ORGANISM: artificial sequence
<220> FEATURE:
<223> OTHER INFORMATION: complement to SEQ ID NO: 7

<400> SEQUENCE: 8
ccggtgtgta ttttatg                                                      17
```

<210> SEQ ID NO 9
<211> LENGTH: 25
<212> TYPE: DNA
<213> ORGANISM: artificial sequence
<220> FEATURE:
<223> OTHER INFORMATION: EYA1A-VMO

<400> SEQUENCE: 9
ctgcaacttg aggaaacagc aacat                                          25

<210> SEQ ID NO 10
<211> LENGTH: 22
<212> TYPE: DNA
<213> ORGANISM: artificial sequence
<220> FEATURE:
<223> OTHER INFORMATION: 53BP1-VMO

<400> SEQUENCE: 10
tccatctgct ccctggcat cc                                              22

<210> SEQ ID NO 11
<211> LENGTH: 205
<212> TYPE: PRT
<213> ORGANISM: artificial sequence
<220> FEATURE:
<223> OTHER INFORMATION: fragment of human EYA1A sequence

<400> SEQUENCE: 11

Ile Lys Thr Glu Gly Gly Leu Ser Gln Ser Gln Ser Pro Gly Gln Thr
1               5                   10                  15

Gly Phe Leu Ser Tyr Gly Thr Ser Phe Ser Thr Pro Gln Pro Gly Gln
            20                  25                  30

Ala Pro Tyr Ser Tyr Gln Met Gln Gly Ser Ser Phe Thr Thr Ser Ser
        35                  40                  45

Gly Ile Tyr Thr Gly Asn Asn Ser Leu Thr Asn Ser Ser Gly Phe Asn
    50                  55                  60

Ser Ser Gln Gln Asp Tyr Pro Ser Tyr Pro Ser Phe Gly Gln Gly Gln
65                  70                  75                  80

Tyr Ala Gln Tyr Tyr Asn Ser Ser Pro Tyr Pro Ala His Tyr Met Thr
                85                  90                  95

Ser Ser Asn Thr Ser Pro Thr Thr Pro Ser Thr Asn Ala Thr Tyr Gln
            100                 105                 110

Leu Gln Glu Pro Pro Ser Gly Ile Thr Ser Gln Ala Val Thr Asp Pro
        115                 120                 125

Thr Ala Glu Tyr Ser Thr Ile His Ser Pro Ser Thr Pro Ile Lys Asp
    130                 135                 140

Ser Asp Ser Asp Arg Leu Arg Arg Gly Ser Asp Gly Lys Ser Arg Gly
145                 150                 155                 160

Arg Gly Arg Arg Asn Asn Asn Pro Ser Pro Pro Asp Ser Asp Leu
                165                 170                 175

Glu Arg Val Phe Ile Trp Asp Leu Asp Glu Thr Ile Ile Val Phe His
            180                 185                 190

Ser Leu Leu Thr Gly Ser Tyr Ala Asn Arg Tyr Gly Arg
        195                 200                 205

<210> SEQ ID NO 12
<211> LENGTH: 140
<212> TYPE: PRT
<213> ORGANISM: artificial
<220> FEATURE:

```
<223> OTHER INFORMATION: fragment of human EYA1A sequence
<220> FEATURE:
<221> NAME/KEY: misc_feature
<222> LOCATION: (43)..(43)
<223> OTHER INFORMATION: Xaa can be Gly or Ser
<220> FEATURE:
<221> NAME/KEY: misc_feature
<222> LOCATION: (48)..(48)
<223> OTHER INFORMATION: Xaa can be Asp or Gly
<220> FEATURE:
<221> NAME/KEY: misc_feature
<222> LOCATION: (61)..(61)
<223> OTHER INFORMATION: Xaa can be Arg or Gln
<220> FEATURE:
<221> NAME/KEY: misc_feature
<222> LOCATION: (110)..(110)
<223> OTHER INFORMATION: Xaa can be Ser or Pro
<220> FEATURE:
<221> NAME/KEY: misc_feature
<222> LOCATION: (130)..(130)
<223> OTHER INFORMATION: Xaa can be Lys or Arg

<400> SEQUENCE: 12

Gln Val His Ile Asp Asp Val Ser Ser Asp Asp Asn Gly Gln Asp Leu
1               5                   10                  15

Ser Thr Tyr Asn Phe Gly Thr Asp Gly Phe Pro Ala Ala Ala Thr Ser
            20                  25                  30

Ala Asn Leu Cys Leu Ala Thr Gly Val Arg Xaa Ala Ala Gly Val Xaa
        35                  40                  45

Ala Ala Trp Met Arg Lys Leu Ala Phe Arg Tyr Arg Xaa Ala Ala Val
    50                  55                  60

Lys Glu Ile Tyr Asn Thr Tyr Lys Asn Val Gly Gly Leu Leu Gly
65                  70                  75                  80

Pro Ala Lys Arg Glu Ala Trp Leu Gln Leu Arg Ala Glu Ile Glu Ala
                85                  90                  95

Leu Thr Asp Ser Trp Leu Thr Leu Ala Leu Lys Ala Leu Xaa Ala Ala
            100                 105                 110

Leu Ile His Ser Arg Thr Asn Cys Val Asn Ile Leu Val Thr Thr Thr
        115                 120                 125

Gln Xaa Ala Ala Ile Pro Ala Leu Ala Lys Val Leu
    130                 135                 140

<210> SEQ ID NO 13
<211> LENGTH: 204
<212> TYPE: DNA
<213> ORGANISM: artificial sequence
<220> FEATURE:
<223> OTHER INFORMATION: reverse sequence of the CpG island

<400> SEQUENCE: 13
tcagcctccc gagtagctgg gactacaggc gcgcaccaac acgaccagct aattttttt      60 tgtattttta gtagagacgg agtttcacca tgttggccag gatggtcttg atctgacctc    120
atgatccgcc tgcctcagcc tcccaaagtg ctgggattac aggcatgagc cactgcgccc    180
ggcctaagtg atgattttt tttt                                            204

<210> SEQ ID NO 14
<211> LENGTH: 18
<212> TYPE: DNA
<213> ORGANISM: artificial sequence
<220> FEATURE:
<223> OTHER INFORMATION: EYA1[delta]e10-3'-ASO
<220> FEATURE:
<221> NAME/KEY: misc_feature
<222> LOCATION: (1)..(1)
```

```
<223> OTHER INFORMATION: n is 2'-O-methyluridine
<220> FEATURE:
<221> NAME/KEY: misc_feature
<222> LOCATION: (18)..(18)
<223> OTHER INFORMATION: n is 2'-O-Methyladenosine

<400> SEQUENCE: 14
ntttcaactt ggcagtan                                                    18

<210> SEQ ID NO 15
<211> LENGTH: 22
<212> TYPE: DNA
<213> ORGANISM: artificial sequence
<220> FEATURE:
<223> OTHER INFORMATION: inverse sequence to SEQ ID NO: 10

<400> SEQUENCE: 15
cctacggtcc cctcgtctac ct                                               22

<210> SEQ ID NO 16
<211> LENGTH: 25
<212> TYPE: DNA
<213> ORGANISM: artificial sequence
<220> FEATURE:
<223> OTHER INFORMATION: control VMO

<400> SEQUENCE: 16
cctcttacct cagttacaat ttata                                            25

<210> SEQ ID NO 17
<211> LENGTH: 19
<212> TYPE: PRT
<213> ORGANISM: artificial sequence
<220> FEATURE:
<223> OTHER INFORMATION: antigenic peptide

<400> SEQUENCE: 17

Cys Gly Ser Ser Glu Ser Pro Ser Gly Pro Lys Leu Gly Asn Ser His
1               5                   10                  15

Ile Asn Ser

<210> SEQ ID NO 18
<211> LENGTH: 20
<212> TYPE: PRT
<213> ORGANISM: artificial sequence
<220> FEATURE:
<223> OTHER INFORMATION: antigenic peptide

<400> SEQUENCE: 18

Cys Met Glu Met Gln Asp Leu Thr Ser Pro His Ser Arg Leu Ser Gly
1               5                   10                  15

Ser Ser Glu Ser
            20

<210> SEQ ID NO 19
<211> LENGTH: 14
<212> TYPE: PRT
<213> ORGANISM: artificial sequence
<220> FEATURE:
<223> OTHER INFORMATION: antigenic peptide

<400> SEQUENCE: 19

Gly Ile Ser Ser Tyr Gly Ile Lys Thr Glu Gly Gly Leu Ser
1               5                   10
```

```
<210> SEQ ID NO 20
<211> LENGTH: 90
<212> TYPE: DNA
<213> ORGANISM: artificial sequence
<220> FEATURE:
<223> OTHER INFORMATION: Exon 10 of human Eya1
<220> FEATURE:
<221> NAME/KEY: misc_feature
<222> LOCATION: (32)..(32)
<223> OTHER INFORMATION: n is a or g

<400> SEQUENCE: 20
gatccaccca cttcagtttc ccttggactg cnaatggaag aaatgatttt caacttggca      60
gacacacatt tatttttaa tgacttagaa                                        90

<210> SEQ ID NO 21
<211> LENGTH: 204
<212> TYPE: DNA
<213> ORGANISM: artificial sequence
<220> FEATURE:
<223> OTHER INFORMATION: CpG island in human EYA1

<400> SEQUENCE: 21
aaaaaaaaaa tcatcactta ggccgggcgc agtggctcat gcctgtaatc ccagcacttt      60
gggaggctga ggcaggcgga tcatgaggtc agatcaagac catcctggcc aacatggtga     120
aactccgtct ctactaaaaa tacaaaaaaa aattagctgg tcgtgttggt gcgcgcctgt     180
agtcccagct actcgggagg ctga                                            204

<210> SEQ ID NO 22
<211> LENGTH: 204
<212> TYPE: DNA
<213> ORGANISM: artificial sequence
<220> FEATURE:
<223> OTHER INFORMATION: reverse complement of the CpG island in human
      EYA1

<400> SEQUENCE: 22
tcagcctccc gagtagctgg gactacaggc gcgcaccaac acgaccagct aattttttt      60 tgtattttta gtagagacgg agtttcacca tgttggccag gatggtcttg atctgacctc     120
atgatccgcc tgcctcagcc tcccaaagtg ctgggattac aggcatgagc cactgcgccc     180
ggcctaagtg atgatttttt tttt                                            204

<210> SEQ ID NO 23
<211> LENGTH: 22
<212> TYPE: DNA
<213> ORGANISM: artificial sequence
<220> FEATURE:
<223> OTHER INFORMATION: mmActa2-F oligonucleotide

<400> SEQUENCE: 23
ctcttccagc catctttcat tg                                               22

<210> SEQ ID NO 24
<211> LENGTH: 25
<212> TYPE: DNA
<213> ORGANISM: artificial sequence
<220> FEATURE:
<223> OTHER INFORMATION: mmActa2-R oligonucleotide

<400> SEQUENCE: 24
gttgttagca tagagatcct ttcct                                            25
```

```
<210> SEQ ID NO 25
<211> LENGTH: 21
<212> TYPE: DNA
<213> ORGANISM: artificial sequence
<220> FEATURE:
<223> OTHER INFORMATION: mmCol1a1-F oligonucleotide

<400> SEQUENCE: 25
atggattccc gttcgagtac g                                        21

<210> SEQ ID NO 26
<211> LENGTH: 20
<212> TYPE: DNA
<213> ORGANISM: artificial sequence
<220> FEATURE:
<223> OTHER INFORMATION: mmCol1a1-R oligonucleotide

<400> SEQUENCE: 26
tcagctggat agcgacatcg                                          20

<210> SEQ ID NO 27
<211> LENGTH: 18
<212> TYPE: DNA
<213> ORGANISM: artificial sequence
<220> FEATURE:
<223> OTHER INFORMATION: EYA1[delta] e10-5'-ASO
<220> FEATURE:
<221> NAME/KEY: misc_feature
<222> LOCATION: (1)..(1)
<223> OTHER INFORMATION: n is 2'-O-methylcytidine
<220> FEATURE:
<221> NAME/KEY: misc_feature
<222> LOCATION: (18)..(18)
<223> OTHER INFORMATION: n is 2'-O-methylguanosine

<400> SEQUENCE: 27
nccttggact gcgaatgn                                            18

<210> SEQ ID NO 28
<211> LENGTH: 59
<212> TYPE: DNA
<213> ORGANISM: artificial
<220> FEATURE:
<223> OTHER INFORMATION: exon 11 of human EYA1

<400> SEQUENCE: 28
gaatgtgacc aagtccatat agatgatgtt tcttcagatg ataacggaca ggacctaag   59

<210> SEQ ID NO 29
<211> LENGTH: 84
<212> TYPE: DNA
<213> ORGANISM: artificial
<220> FEATURE:
<223> OTHER INFORMATION: exon 9 of human EYA1

<400> SEQUENCE: 29
agagtgttca tctgggactt ggatgagaca atcattgttt tccactcctt gcttactggg   60
tcctacgcca acagatatgg gagg                                          84

<210> SEQ ID NO 30
<211> LENGTH: 22
<212> TYPE: DNA
<213> ORGANISM: artificial
<220> FEATURE:
<223> OTHER INFORMATION: antisense oligonucleotide against p53bp1

<400> SEQUENCE: 30
```

```
tccatctgct ccccaggcat cc                                              22

<210> SEQ ID NO 31
<211> LENGTH: 51
<212> TYPE: DNA
<213> ORGANISM: artificial
<220> FEATURE:
<223> OTHER INFORMATION: target sequence of antisense oligonucleotide
      against p53Bp1

<400> SEQUENCE: 31
ggacctcccg ccgggatgcc tggggagcag atggaccta ctggaagtca g              51

<210> SEQ ID NO 32
<211> LENGTH: 51
<212> TYPE: DNA
<213> ORGANISM: artificial
<220> FEATURE:
<223> OTHER INFORMATION: target sequence of antisense oligonucleotide
      against p53Bp1

<400> SEQUENCE: 32
ggacctcccg ccgggatgcc aggggagcag atggaccta ctggaagtca g              51

<210> SEQ ID NO 33
<211> LENGTH: 25
<212> TYPE: DNA
<213> ORGANISM: artificial
<220> FEATURE:
<223> OTHER INFORMATION: ASmotif-893WT

<400> SEQUENCE: 33
ttttacgtgt ggcctcaaac aattc                                           25

<210> SEQ ID NO 34
<211> LENGTH: 29
<212> TYPE: DNA
<213> ORGANISM: artificial
<220> FEATURE:
<223> OTHER INFORMATION: target of antisense oligonucleotide

<400> SEQUENCE: 34
cagtttccct tggactgcga atggaagaa                                       29

<210> SEQ ID NO 35
<211> LENGTH: 23
<212> TYPE: DNA
<213> ORGANISM: artificial sequence
<220> FEATURE:
<223> OTHER INFORMATION: target of antisense oligonucleotide

<400> SEQUENCE: 35
tgattttcaa cttggcagac aca                                             23

<210> SEQ ID NO 36
<211> LENGTH: 40
<212> TYPE: DNA
<213> ORGANISM: artificial sequence
<220> FEATURE:
<223> OTHER INFORMATION: target of antisense oligonucleotide

<400> SEQUENCE: 36
gccagttcag atgttgctgt ttcctcaagt tgcaggtaag                           40

<210> SEQ ID NO 37
<211> LENGTH: 14
```

```
<212> TYPE: DNA
<213> ORGANISM: artificial sequence
<220> FEATURE:
<223> OTHER INFORMATION: target of antisense oligonucleotide

<400> SEQUENCE: 37
tttcaacttg gcag                                                      14

<210> SEQ ID NO 38
<211> LENGTH: 19
<212> TYPE: PRT
<213> ORGANISM: artificial sequence
<220> FEATURE:
<223> OTHER INFORMATION: antigenic peptide

<400> SEQUENCE: 38

Cys Glu Glu Met Ile Phe Asn Leu Ala Asp Thr His Leu Phe Phe Asn
1               5                   10                  15

Asp Leu Glu

<210> SEQ ID NO 39
<211> LENGTH: 24
<212> TYPE: DNA
<213> ORGANISM: artificial
<220> FEATURE:
<223> OTHER INFORMATION: target of antisense oligonucleotide

<400> SEQUENCE: 39
tttcccttgg actgcgaatg gaag                                           24

<210> SEQ ID NO 40
<211> LENGTH: 23
<212> TYPE: DNA
<213> ORGANISM: artificial
<220> FEATURE:
<223> OTHER INFORMATION: target of antisense oligonucleotide

<400> SEQUENCE: 40
gattttcaac ttggcagaca cac                                            23

<210> SEQ ID NO 41
<211> LENGTH: 35
<212> TYPE: DNA
<213> ORGANISM: artificial
<220> FEATURE:
<223> OTHER INFORMATION: sequence of human eya1 comprising a splicing
      cis regulatory motif

<400> SEQUENCE: 41
agtgttagtg tattttacgt gtggcctcaa acaat                               35

<210> SEQ ID NO 42
<211> LENGTH: 21
<212> TYPE: DNA
<213> ORGANISM: artificial sequence
<220> FEATURE:
<223> OTHER INFORMATION: splicing regulatory motif in human eya1

<400> SEQUENCE: 42
gtgtatttta cgtgtggcct c                                              21

<210> SEQ ID NO 43
<211> LENGTH: 21
<212> TYPE: DNA
<213> ORGANISM: artificial sequence
<220> FEATURE:
```

```
<223> OTHER INFORMATION: splicing regulatory motif in human eya1
      comprising rs13259388

<400> SEQUENCE: 43
gtgtatttta tgtgtggcct c                                          21

<210> SEQ ID NO 44
<211> LENGTH: 21
<212> TYPE: DNA
<213> ORGANISM: artificial sequence
<220> FEATURE:
<223> OTHER INFORMATION: sequence in Gorilla corresponding to the
      splicing regulatory motif in human eay1

<400> SEQUENCE: 44
gtgtacttta tgtgtggcct c                                          21

<210> SEQ ID NO 45
<211> LENGTH: 21
<212> TYPE: DNA
<213> ORGANISM: artificial sequence
<220> FEATURE:
<223> OTHER INFORMATION: sequence in Vervet corresponding to the
      splicing regulatory motif in human eya1

<400> SEQUENCE: 45
gtgtatttta tgtgttgcct c                                          21

<210> SEQ ID NO 46
<211> LENGTH: 31
<212> TYPE: DNA
<213> ORGANISM: artificial sequence
<220> FEATURE:
<223> OTHER INFORMATION: fragment of a CpG island of human Eya1

<400> SEQUENCE: 46
tcatcactta ggccgggcgc agtggctcat g                               31

<210> SEQ ID NO 47
<211> LENGTH: 32
<212> TYPE: DNA
<213> ORGANISM: artificial sequence
<220> FEATURE:
<223> OTHER INFORMATION: fragment of a CpG island of human Eya1

<400> SEQUENCE: 47
ggaggctgag gcaggcggat catgaggtca ga                              32

<210> SEQ ID NO 48
<211> LENGTH: 29
<212> TYPE: DNA
<213> ORGANISM: artificial sequence
<220> FEATURE:
<223> OTHER INFORMATION: fragment of a CpG island of human Eya1

<400> SEQUENCE: 48
aaaatacaaa aaaaaattag ctggtcgtg                                  29

<210> SEQ ID NO 49
<211> LENGTH: 17
<212> TYPE: DNA
<213> ORGANISM: artificial sequence
<220> FEATURE:
<223> OTHER INFORMATION: wild type counterpart of SEQ ID NO: 8

<400> SEQUENCE: 49
``` ccgtgtgtc ttttatg                                                 17

<210> SEQ ID NO 50
<211> LENGTH: 557
<212> TYPE: PRT
<213> ORGANISM: Homo sapiens

<400> SEQUENCE: 50

Met Glu Met Gln Asp Leu Thr Ser Pro His Ser Arg Leu Ser Gly Ser
1               5                   10                  15

Ser Glu Ser Pro Ser Gly Pro Lys Leu Gly Asn Ser His Ile Asn Ser
            20                  25                  30

Asn Ser Met Thr Pro Asn Gly Thr Glu Val Lys Thr Glu Pro Met Ser
        35                  40                  45

Ser Ser Glu Thr Ala Ser Thr Thr Ala Asp Gly Ser Leu Asn Asn Phe
    50                  55                  60

Ser Gly Ser Ala Ile Gly Ser Ser Phe Ser Pro Arg Pro Thr His
65                  70                  75                  80

Gln Phe Ser Pro Pro Gln Ile Tyr Pro Ser Asn Arg Pro Tyr Pro His
                85                  90                  95

Ile Leu Pro Thr Pro Ser Ser Gln Thr Met Ala Ala Tyr Gly Gln Thr
            100                 105                 110

Gln Phe Thr Thr Gly Met Gln Gln Ala Thr Ala Tyr Ala Thr Tyr Pro
        115                 120                 125

Gln Pro Gly Gln Pro Tyr Gly Ile Ser Ser Tyr Gly Ile Lys Thr Glu
    130                 135                 140

Gly Gly Leu Ser Gln Ser Gln Ser Pro Gly Gln Thr Gly Phe Leu Ser
145                 150                 155                 160

Tyr Gly Thr Ser Phe Ser Thr Pro Gln Pro Gly Gln Ala Pro Tyr Ser
                165                 170                 175

Tyr Gln Met Gln Gly Ser Ser Phe Thr Thr Ser Ser Gly Ile Tyr Thr
            180                 185                 190

Gly Asn Asn Ser Leu Thr Asn Ser Ser Gly Phe Asn Ser Ser Gln Gln
        195                 200                 205

Asp Tyr Pro Ser Tyr Pro Ser Phe Gly Gln Gly Gln Tyr Ala Gln Tyr
    210                 215                 220

Tyr Asn Ser Ser Pro Tyr Pro Ala His Tyr Met Thr Ser Ser Asn Thr
225                 230                 235                 240

Ser Pro Thr Thr Pro Ser Thr Asn Ala Thr Tyr Gln Leu Gln Glu Pro
                245                 250                 255

Pro Ser Gly Ile Thr Ser Gln Ala Val Thr Asp Pro Thr Ala Glu Tyr
            260                 265                 270

Ser Thr Ile His Ser Pro Ser Thr Pro Ile Lys Asp Ser Asp Ser Asp
        275                 280                 285

Arg Leu Arg Arg Gly Ser Asp Gly Lys Ser Arg Gly Arg Gly Arg Arg
    290                 295                 300

Asn Asn Asn Pro Ser Pro Pro Asp Ser Asp Leu Glu Arg Val Phe
305                 310                 315                 320

Ile Trp Asp Leu Asp Glu Thr Ile Ile Val Phe His Ser Leu Leu Thr
                325                 330                 335

Gly Ser Tyr Ala Asn Arg Tyr Gly Arg Glu Cys Asp Gln Val His Ile
            340                 345                 350

Asp Asp Val Ser Ser Asp Asp Asn Gly Gln Asp Leu Ser Thr Tyr Asn
        355                 360                 365

```
Phe Gly Thr Asp Gly Phe Pro Ala Ala Ala Thr Ser Ala Asn Leu Cys
    370                 375                 380

Leu Ala Thr Gly Val Arg Gly Gly Val Asp Trp Met Arg Lys Leu Ala
385                 390                 395                 400

Phe Arg Tyr Arg Arg Val Lys Glu Ile Tyr Asn Thr Tyr Lys Asn Asn
                405                 410                 415

Val Gly Gly Leu Leu Gly Pro Ala Lys Arg Glu Ala Trp Leu Gln Leu
            420                 425                 430

Arg Ala Glu Ile Glu Ala Leu Thr Asp Ser Trp Leu Thr Leu Ala Leu
            435                 440                 445

Lys Ala Leu Ser Leu Ile His Ser Arg Thr Asn Cys Val Asn Ile Leu
450                 455                 460

Val Thr Thr Thr Gln Leu Ile Pro Ala Leu Ala Lys Val Leu Leu Tyr
465                 470                 475                 480

Gly Leu Gly Ile Val Phe Pro Ile Glu Asn Ile Tyr Ser Ala Thr Lys
                485                 490                 495

Ile Gly Lys Glu Ser Cys Phe Gly Arg Ile Ile Gln Arg Phe Gly Arg
            500                 505                 510

Lys Val Val Tyr Val Val Ile Gly Asp Gly Val Glu Glu Glu Gln Gly
            515                 520                 525

Ala Lys Lys His Ala Met Pro Phe Trp Arg Ile Ser Ser His Ser Asp
            530                 535                 540

Leu Met Ala Leu His His Ala Leu Glu Leu Glu Tyr Leu
545                 550                 555

<210> SEQ ID NO 51
<211> LENGTH: 90
<212> TYPE: DNA
<213> ORGANISM: artificial sequence
<220> FEATURE:
<223> OTHER INFORMATION: exon 10 of human Eya1

<400> SEQUENCE: 51
gatccaccca cttcagtttc ccttggactg cgaatggaag aaatgatttt caacttggca      60
gacacacatt tattttttaa tgacttagaa                                       90
```